(12) United States Patent
Adachi et al.

(10) Patent No.: US 10,310,376 B2
(45) Date of Patent: Jun. 4, 2019

(54) RESIST COMPOSITION, PATTERN FORMING PROCESS, POLYMER, AND MONOMER

(71) Applicant: SHIN-ETSU CHEMICAL CO., LTD., Tokyo (JP)

(72) Inventors: Teppei Adachi, Joetsu (JP); Ryosuke Taniguchi, Joetsu (JP); Koji Hasegawa, Joetsu (JP); Kenji Yamada, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 6 days.

(21) Appl. No.: 15/372,622

(22) Filed: Dec. 8, 2016

(65) Prior Publication Data

US 2017/0184967 A1    Jun. 29, 2017

(30) Foreign Application Priority Data

Dec. 25, 2015    (JP) .................................. 2015-253067

(51) Int. Cl.
| | |
|---|---|
| *G03F 7/004* | (2006.01) |
| *G03F 7/38* | (2006.01) |
| *C08F 224/00* | (2006.01) |
| *G03F 7/038* | (2006.01) |
| *G03F 7/20* | (2006.01) |
| *G03F 7/11* | (2006.01) |
| *C07D 307/77* | (2006.01) |
| *C07D 307/93* | (2006.01) |
| *C07D 307/94* | (2006.01) |
| *C07D 493/18* | (2006.01) |
| *C07D 493/20* | (2006.01) |
| *C08F 220/18* | (2006.01) |
| *C08F 220/28* | (2006.01) |
| *G03F 7/16* | (2006.01) |
| *G03F 7/32* | (2006.01) |
| *G03F 7/039* | (2006.01) |

(52) U.S. Cl.
CPC ......... *G03F 7/0382* (2013.01); *C07D 307/77* (2013.01); *C07D 307/93* (2013.01); *C07D 307/94* (2013.01); *C07D 493/18* (2013.01); *C07D 493/20* (2013.01); *C08F 220/18* (2013.01); *C08F 220/28* (2013.01); *C08F 224/00* (2013.01); *G03F 7/0045* (2013.01); *G03F 7/0046* (2013.01); *G03F 7/0397* (2013.01); *G03F 7/11* (2013.01); *G03F 7/162* (2013.01); *G03F 7/168* (2013.01); *G03F 7/2002* (2013.01); *G03F 7/2041* (2013.01); *G03F 7/322* (2013.01); *G03F 7/325* (2013.01); *G03F 7/327* (2013.01); *G03F 7/38* (2013.01); *C08F 2220/283* (2013.01); *C08F 2800/20* (2013.01)

(58) Field of Classification Search
CPC ........ G03F 7/0397; G03F 7/2041; G03F 7/11; G03F 7/38; C08F 2220/283; C08F 224/00
USPC ...... 430/270.1, 910, 271.1, 273.1, 325, 326, 430/905; 526/287, 292.95; 556/35, 36
See application file for complete search history.

(56) References Cited

U.S. PATENT DOCUMENTS

| | | | |
|---|---|---|---|
| 6,746,818 B2 | 6/2004 | Kinsho et al. | |
| 7,041,838 B2 | 5/2006 | Kamon et al. | |
| 2009/0297979 A1* | 12/2009 | Hatakeyama | ........... C07C 69/54 430/270.1 |
| 2011/0033799 A1* | 2/2011 | Watanabe | ............. C08F 220/60 430/270.1 |
| 2011/0294070 A1* | 12/2011 | Hatakeyama | ........... C08F 20/26 430/285.1 |
| 2012/0219913 A1 | 8/2012 | Kataoka et al. | |
| 2014/0363772 A1 | 12/2014 | Tsuchiya et al. | |

FOREIGN PATENT DOCUMENTS

| | | |
|---|---|---|
| JP | 2002-234882 A | 8/2002 |
| JP | 2002-371114 A | 12/2002 |

OTHER PUBLICATIONS

Extended European Search Report dated May 22, 2017, issued in counterpart European Patent Application No. 16203978.8. (8 pages).

* cited by examiner

*Primary Examiner* — John S Chu
(74) *Attorney, Agent, or Firm* — Westerman, Hattori, Daniels & Adrian, LLP

(57) ABSTRACT

A polymer comprising recurring units containing a specific lactone ring and having an alkyl group on γ-butyrolactone skeleton of fused ring lactone and an alkyl ester substituent group intervening between the lactone structure and the polymer backbone is provided. A resist composition comprising the polymer as base resin is improved in such properties as DOF margin and MEF and quite effective for precise micropatterning.

13 Claims, No Drawings

RESIST COMPOSITION, PATTERN FORMING PROCESS, POLYMER, AND MONOMER

CROSS-REFERENCE TO RELATED APPLICATION

This non-provisional application claims priority under 35 U.S.C. § 119(a) on Patent Application No. 2015-253067 filed in Japan on Dec. 25, 2015, the entire contents of which are hereby incorporated by reference.

TECHNICAL FIELD

This invention relates to a resist composition for use in photolithography for micropatterning in the manufacture of microelectronic devices, a pattern forming process using the resist composition, a polymer suited for use in the resist composition as base resin, and a monomer for the polymer.

BACKGROUND ART

To meet the demand for higher integration density and operating speed of LSIs, the effort to reduce the pattern rule is in rapid progress. As the advanced micropatterning technology, the ArF immersion lithography involving exposure through a liquid (typically water) held between a projection lens and a substrate is utilized. Besides, studies are being made on the multi-patterning of ArF lithography and the lithography using extreme ultraviolet (EUV) of wavelength 13.5 nm.

In these lithography processes, chemically amplified resist compositions are used. Among constituent units of the base resin, lactone ring-containing constituent units are important in forming patterns at a high resolution, as viewed from the standpoints of dissolution contrast and control of acid diffusion. Suitable compounds providing such constituent units include, for example, methacrylic compounds having a lactone unit such as butyrolactone, valerolactone, norbornanelactone or cyclohexanelactone, or sultone unit. Inter alia, a focus is put on the condensed ring lactone containing butyrolactone skeleton, specifically 7-methacryloyloxy-3-oxabicyclo[4.3.0]nonan-2-one, 8-methacryloyloxy-3-oxabicyclo[4.3.0]nonan-2-one, and a mixture thereof (Patent Document 1) and spiro[methacryloyloxynorbornane-2,3'-tetrahydrofuran-2-one] (Patent Document 2).

CITATION LIST

Patent Document 1: JP-A 2002-234882
Patent Document 2: JP-A 2002-371114 (U.S. Pat. No. 6,746,818)

DISCLOSURE OF INVENTION

For further miniaturization, resist compositions comprising a base resin containing the afore-mentioned lactone are still insufficient in some performance factors including resolution and resist pattern profile.

An object of the invention is to provide a resist composition which when processed by photolithography, is improved in resolution and pattern profile, and exhibits satisfactory depth-of-focus (DOF) margin and mask error factor (MEF), a pattern forming process using the resist composition, a polymer suited for use in the resist composition as base resin, and a monomer for the polymer.

The inventors have found that a resist composition comprising a polymer comprising recurring units containing a specific lactone ring as base resin is improved in such properties as DOF margin and MEF and quite effective for precise micropatterning and that a lactone compound from which the recurring units are derived is readily obtained in high yields.

The recurring unit containing a specific lactone ring possesses an alkyl group on γ-butyrolactone skeleton of fused ring lactone and an alkyl ester substituent group intervening between the lactone structure and the polymer backbone, which ensures an appropriate organic solvent solubility. When a resist film is patterned by organic solvent development, the lipophilicity due to these substituent groups contributes to improved developer solubility and a high dissolution contrast.

In one aspect, the invention provides a polymer comprising recurring units having the formula (1).

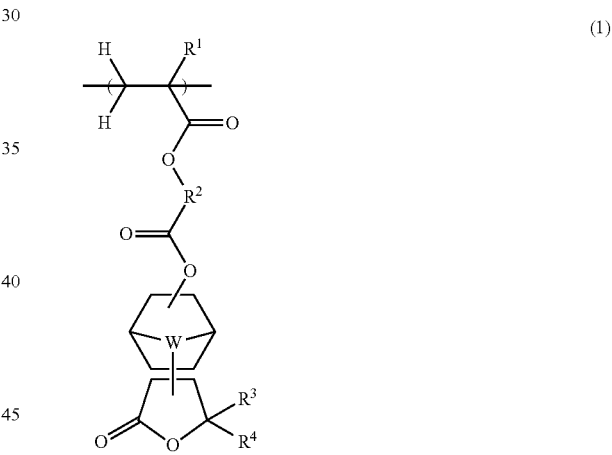

Herein $R^1$ is hydrogen or methyl, $R^2$ is a $C_1$-$C_{20}$ straight, branched or cyclic divalent hydrocarbon group in which any constituent —$CH_2$— moiety may be replaced by —O— or —C(=O)—; $R^3$ and $R^4$ are each independently hydrogen or a $C_1$-$C_{15}$ straight, branched or cyclic alkyl group, at least one of $R^3$ and $R^4$ is a $C_1$-$C_{15}$ straight, branched or cyclic alkyl group, $R^3$ and $R^4$ may bond together to form a ring with the carbon atom to which they are attached, a ring-forming combination of $R^3$ and $R^4$ is a $C_2$-$C_{15}$ straight, branched or cyclic alkylene group; W is —$CH_2$—, —$CH_2CH_2$— or —O—, or two separate —H; the broken line designates a single bond or divalent organic group bonding the norbornane, bicyclo[2.2.2]octane, 7-oxanorbornane or cyclohexane ring structure to the γ-butyrolactone ring structure, or a structure sharing one or two constituent carbon atoms between these ring structures.

In a preferred embodiment, the recurring units having the formula (1) are recurring units having the formula (2) or (3).

(2)

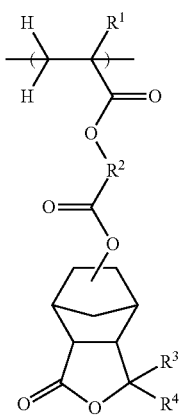

(3)

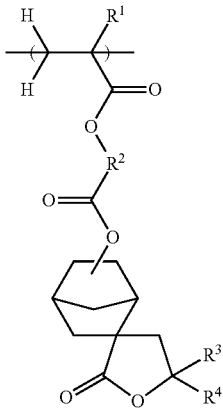

Herein $R^1$ to $R^4$ are as defined above.

In a preferred embodiment, the polymer may further comprise recurring units having the formula (4).

(4)

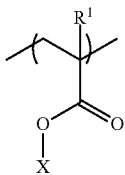

Herein $R^1$ is as defined above, and X is an acid labile group.

In a preferred embodiment, the polymer may further comprise recurring units of at least one type selected from recurring units having the formulae (5) to (7).

(5)

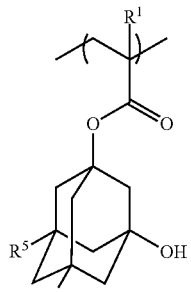

(6)

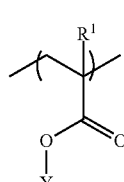

(7)

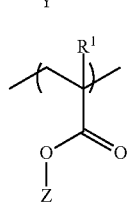

Herein $R^1$ is as defined above, $R^5$ and $R^6$ are each independently hydrogen or hydroxyl, Y is a substituent group containing a lactone structure different from formula (1) or a substituent group containing a sultone structure, Z is hydrogen, a $C_1$-$C_{15}$ fluorinated hydrocarbon group, or a $C_1$-$C_{15}$ fluoroalcohol-containing substituent group.

In a second aspect, the invention provides a resist composition comprising (A) a base resin comprising the polymer defined above, (B) a photoacid generator, and (C) a solvent.

In a preferred embodiment, the photoacid generator (B) comprises a photoacid generator having the formula (B-1).

(B-1)

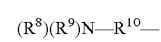

Herein $R^7$ is a $C_1$-$C_{35}$ straight, branched or cyclic monovalent hydrocarbon group which may contain an oxygen atom, a nitrogen-containing heterocyclic group, or a group of the formula (i):

$$(R^8)(R^9)N-R^{10}-\qquad\text{(i)}$$

wherein $R^8$ and $R^9$ are each independently hydrogen or a $C_1$-$C_{20}$ monovalent hydrocarbon group which may contain a heteroatom, $R^8$ and $R^9$ may bond together to form a ring with the nitrogen atom to which they are attached, $R^{10}$ is a $C_1$-$C_{20}$ divalent hydrocarbon group which may contain a heteroatom; A is hydrogen or trifluoromethyl, $R^{101}$, $R^{102}$ and $R^{103}$ are each independently an optionally substituted $C_1$-$C_{10}$ straight or branched alkyl, alkenyl or oxoalkyl group, or an optionally substituted $C_6$-$C_{18}$ aryl, aralkyl or aryloxoalkyl group, any two of $R^{101}$, $R^{102}$ and $R^{103}$ may bond together to form a ring with the sulfur atom to which they are attached.

In a preferred embodiment, the photoacid generator (B) comprises a photoacid generator having the formula (B-2).

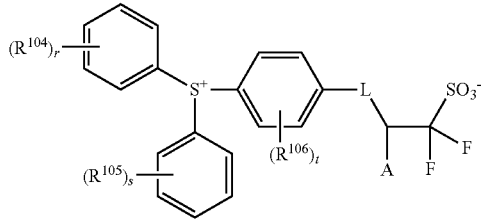
(B-2)

Herein A is hydrogen or trifluoromethyl, $R^{104}$, $R^{105}$ and $R^{106}$ are each independently hydrogen or a $C_1$-$C_{20}$ straight, branched or cyclic monovalent hydrocarbon group which may contain a heteroatom; r and s are each independently an integer of 0 to 5, t is an integer of 0 to 4; and L is a single bond or a $C_1$-$C_{20}$ straight, branched or cyclic divalent hydrocarbon group which may contain a heteroatom.

In a preferred embodiment, the photoacid generator (B) comprises a photoacid generator having the formula (B-3).

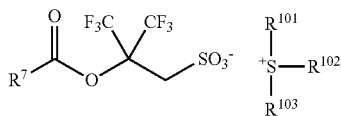
(B-3)

Herein $R^7$ is a $C_1$-$C_{35}$ straight, branched or cyclic monovalent hydrocarbon group which may contain an oxygen atom, a nitrogen-containing heterocyclic group, or a group of the formula (i):

$$(R^8)(R^9)N-R^{10}- \quad (i)$$

wherein $R^8$ and $R^9$ are each independently hydrogen or a $C_1$-$C_{20}$ monovalent hydrocarbon group which may contain a heteroatom, $R^8$ and $R^9$ may bond together to form a ring with the nitrogen atom to which they are attached, $R^{10}$ is a $C_1$-$C_{20}$ divalent hydrocarbon group which may contain a heteroatom; $R^{101}$, $R^{102}$ and $R^{103}$ are each independently an optionally substituted $C_1$-$C_{10}$ straight or branched alkyl, alkenyl or oxoalkyl group, or an optionally substituted $C_6$-$C_{18}$ aryl, aralkyl or aryloxoalkyl group, any two of $R^{101}$, $R^{102}$ and $R^{103}$ may bond together to form a ring with the sulfur atom to which they are attached.

The resist composition may further comprise (D) a second polymer different from the polymer (A), the second polymer comprising recurring units of at least one type selected from recurring units having the formulae (D-1) to (D-5).

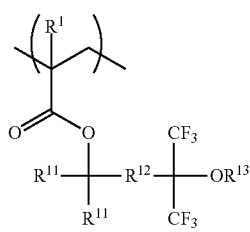
(D-1)

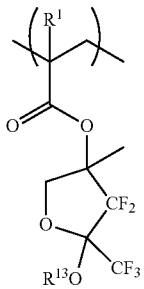
(D-2)

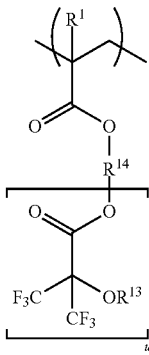
(D-3)

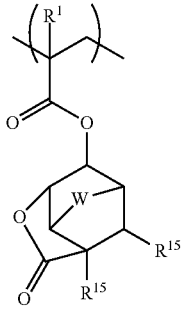
(D-4)

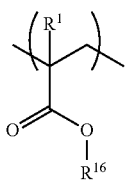
(D-5)

Herein $R^1$ and W are as defined above; $R^{11}$ is each independently hydrogen or a $C_1$-$C_{10}$ straight, branched or cyclic monovalent hydrocarbon group; $R^{12}$ is a single bond or a $C_1$-$C_5$ straight or branched divalent hydrocarbon group; $R^{13}$ is each independently hydrogen, a $C_1$-$C_{15}$ straight, branched or cyclic monovalent hydrocarbon or monovalent fluorinated hydrocarbon group, or an acid labile group, the monovalent hydrocarbon or fluorinated hydrocarbon group represented by $R^{13}$ may have an ether bond (—O—) or carbonyl moiety (—C(=O)—) intervening in a carbon-carbon bond; $R^{14}$ is a $C_1$-$C_{20}$ straight, branched or cyclic (u+1)-valent hydrocarbon or fluorinated hydrocarbon group; u is an integer of 1 to 3; $R^{15}$ is each independently hydrogen or a group of the formula (ii):

$$-C(=O)-O-R^{17} \quad (ii)$$

wherein $R^{17}$ is a $C_1$-$C_{20}$ straight, branched or cyclic monovalent fluorinated hydrocarbon group; $R^{16}$ is a $C_1$-$C_{15}$ straight, branched or cyclic monovalent hydrocarbon or monovalent fluorinated hydrocarbon group which may have an ether bond (—O—) or carbonyl moiety (—C(=O)—) intervening in a carbon-carbon bond.

In a third aspect, the invention provides a pattern forming process comprising the steps of applying the resist composition defined herein onto a substrate, prebaking to form a resist film, exposing the resist film to KrF excimer laser, ArF excimer laser, EB or EUV, baking, and developing the exposed resist film in a developer.

Preferably, the exposure step is carried out by immersion lithography using a liquid having a refractive index of at least 1.0 between the resist film and a projection lens.

The process may further comprise the step of forming a protective film on the resist film prior to the exposure step, wherein immersion lithography is carried out while the liquid is held between the protective film and the projection lens.

The developing step may use the developer comprising an organic solvent to form a negative pattern.

In a fourth aspect, the invention provides a monomer having the formula (8).

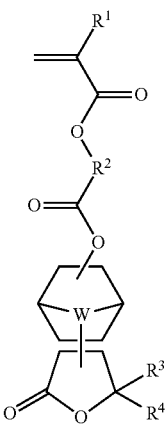

(8)

Herein $R^1$ is hydrogen or methyl, $R^2$ is a $C_1$-$C_{20}$ straight, branched or cyclic divalent hydrocarbon group in which any constituent —$CH_2$— moiety may be replaced by —O— or —C(=O)—; $R^3$ and $R^4$ are each independently hydrogen or a $C_1$-$C_{15}$ straight, branched or cyclic alkyl group, at least one of $R^3$ and $R^4$ is a $C_1$-$C_{15}$ straight, branched or cyclic alkyl group, $R^3$ and $R^4$ may bond together to form a ring with the carbon atom to which they are attached, a ring-forming combination of $R^3$ and $R^4$ is a $C_2$-$C_{15}$ straight, branched or cyclic alkylene group; W is —$CH_2$—, —$CH_2CH_2$— or —O—, or two separate —H; the broken line designates a single bond or divalent organic group bonding the norbornane, bicyclo[2.2.2]octane, 7-oxanorbornane or cyclohexane ring structure to the γ-butyrolactone ring structure, or a structure sharing one or two constituent carbon atoms between these ring structures.

Also contemplated herein are monomers having the formulae (9) and (10) wherein $R^1$ to $R^4$ are as defined above.

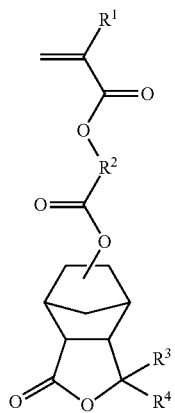

(9)

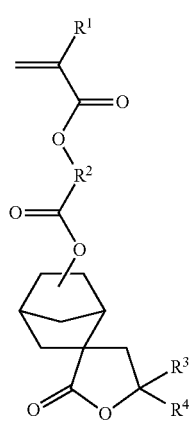

(10)

Advantageous Effects of Invention

When the resist composition is processed by lithography, a high dissolution contrast is obtainable especially in the case of organic solvent development, and a resist pattern with improved DOF margin and MEF can be formed.

DESCRIPTION OF PREFERRED EMBODIMENTS

In the disclosure, the singular forms "a," "an" and "the" include plural referents unless the context clearly dictates otherwise. The notation (Cn-Cm) means a group containing from n to m carbon atoms per group. In the chemical formulae, the broken line denotes a valence bond.

The abbreviations and acronyms have the following meaning.
EUV: extreme ultraviolet
PAG: photoacid generator
Mw: weight average molecular weight
Mn: number average molecular weight
Mw/Mn: molecular weight distribution or dispersity
GPC: gel permeation chromatography
PEBs post-exposure bake
DOFs depth of focus
MEF: mask error factor It is understood that for some structures represented by chemical formulae, there can exist enantiomers and diastereomers because of the presence of asymmetric carbon atoms. In such a case, a single formula collectively represents all such isomers. The isomers may be used alone or in admixture.

Polymer

A first embodiment of the invention is a polymer comprising recurring units having the formula (1).

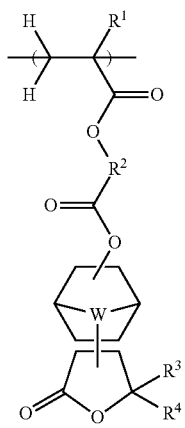
(1)

Herein $R^1$ is hydrogen or methyl. $R^2$ is a $C_1$-$C_{20}$ straight, branched or cyclic divalent hydrocarbon group in which any constituent —$CH_2$— moiety may be replaced by —O— or —C(=O)—. $R^3$ and $R^4$ are each independently hydrogen or a $C_1$-$C_{15}$ straight, branched or cyclic alkyl group, at least one of $R^3$ and $R^4$ is a $C_1$-$C_{15}$ straight, branched or cyclic alkyl group. $R^3$ and $R^4$ may bond together to form a ring with the carbon atom to which they are attached, and in this case, a ring-forming combination of $R^3$ and $R^4$ is a $C_2$-$C_{15}$ straight, branched or cyclic alkylene group. W is —$CH_2$—, —$CH_2CH_2$— or —O—, or two separate —H. The broken line is a single bond or divalent organic group bonding the norbornane, bicyclo[2.2.2]octane, 7-oxanorbornane or cyclohexane ring structure to the γ-butyrolactone ring structure, or designates a structure sharing one or two constituent carbon atoms between these ring structures.

Examples of the $C_1$-$C_{20}$ straight, branched or cyclic divalent hydrocarbon group are given below, but not limited thereto.

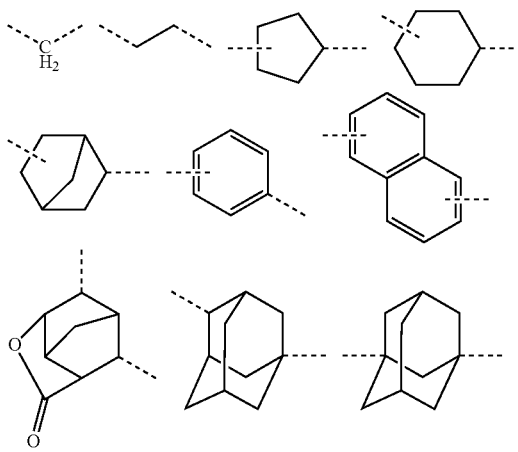

Examples of the $C_1$-$C_{15}$ straight, branched or cyclic alkyl group include methyl, ethyl, n-propyl, isopropyl, cyclopropyl, n-butyl, isobutyl, s-butyl, t-butyl, cyclobutyl, n-pentyl, cyclopentyl, n-hexyl, cyclohexyl, n-heptyl, n-octyl, n-nonyl, n-decyl, n-undecyl, n-dodecyl, tridecyl, tetradecyl, pentadecyl, adamantyl and norbornyl. Inter alia, $C_1$-$C_5$ straight, branched or cyclic alkyl groups are preferred.

W is —$CH_2$—, —$CH_2CH_2$— or —O—, or two separate —H. The relevant structure is a norbornane ring structure when W is —$CH_2$—, a bicyclo[2.2.2]octane ring structure when W is —$CH_2CH_2$—, and a 7-oxanorbornane ring structure when W is —O—. When W is two separate —H, a cyclohexane ring structure as shown below forms.

that is

Exemplary of the divalent organic group depicted by the broken line are $C_1$-$C_6$ alkylene groups and $C_1$-$C_5$ oxaalkylene groups.

Of the recurring units having formula (1), recurring units having the formula (2) or (3) are preferred.

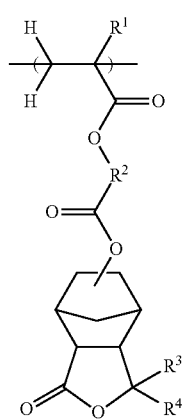
(2)

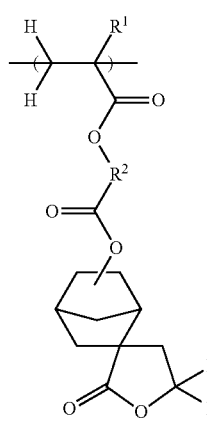
(3)

Herein $R^1$ to $R^4$ are as defined above.

Illustrative, non-limiting examples of the recurring unit having formula (1) are shown below. Herein $R^1$ is as defined above.

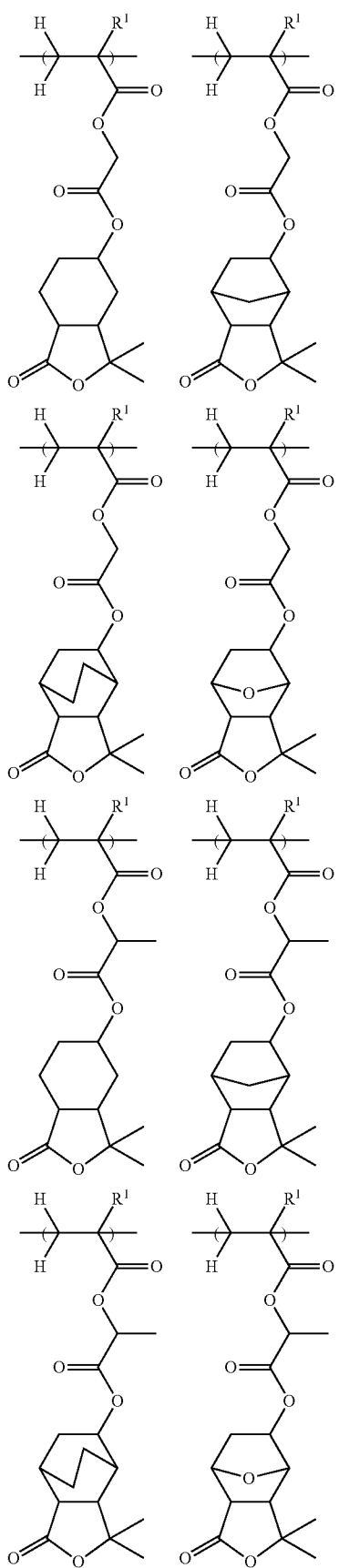
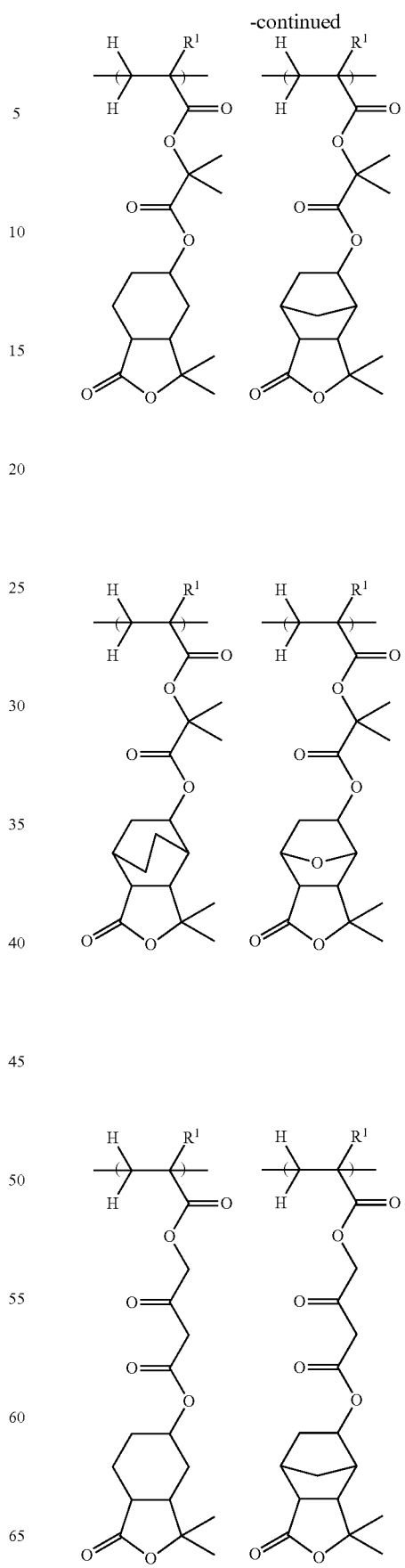

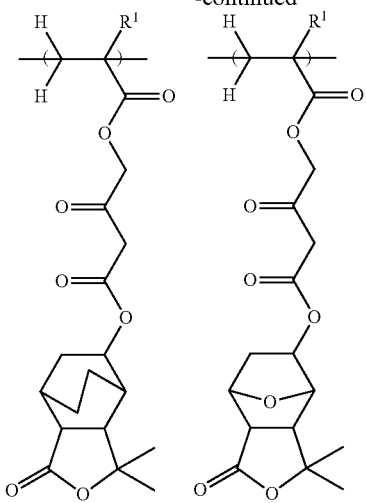
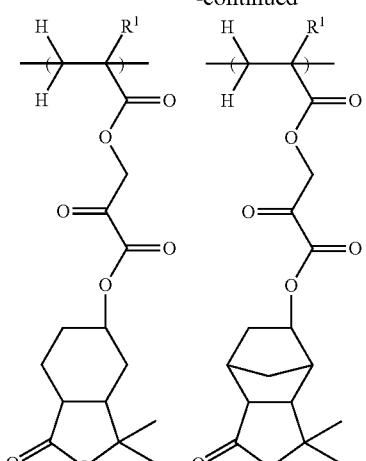
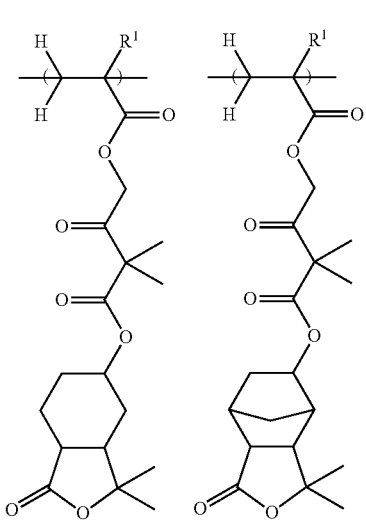
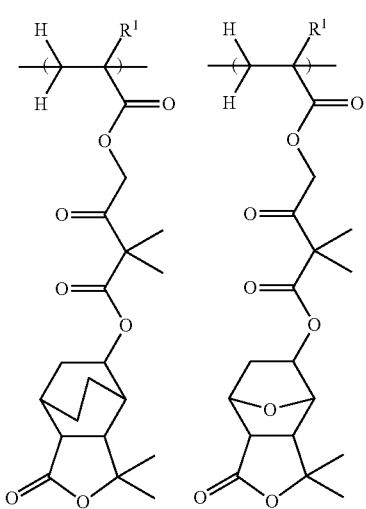
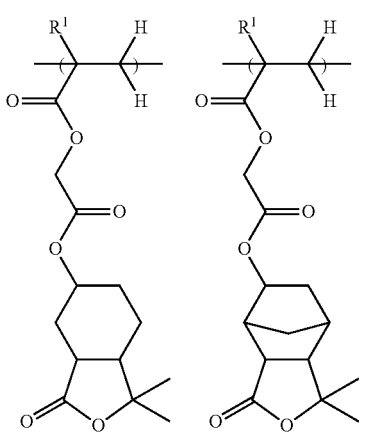

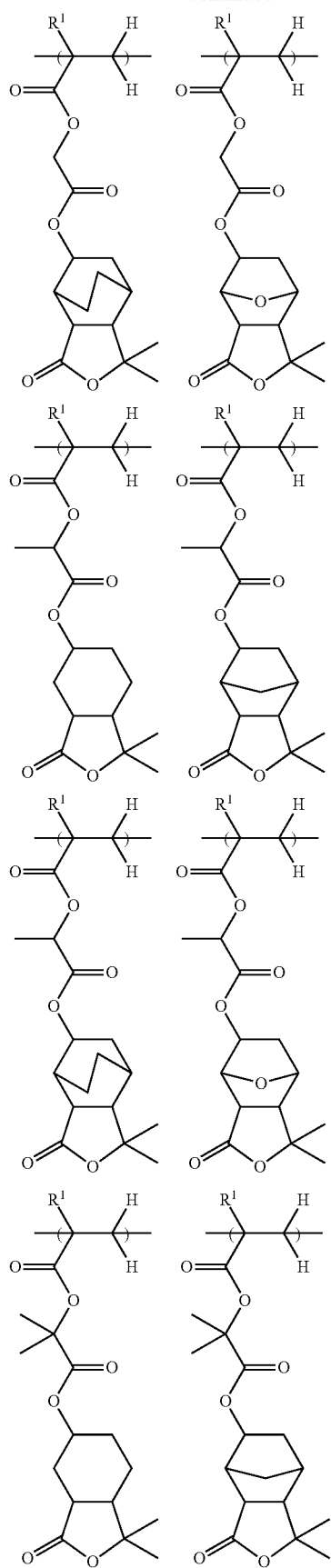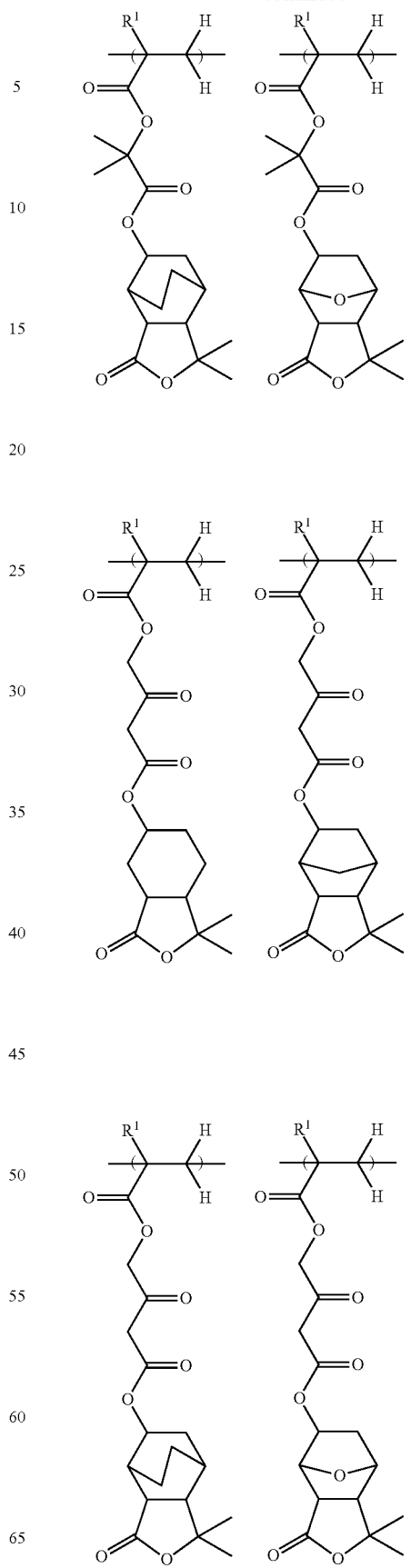

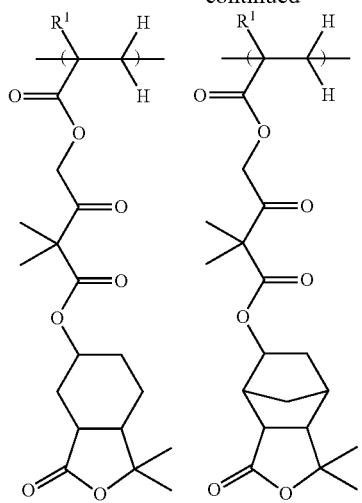
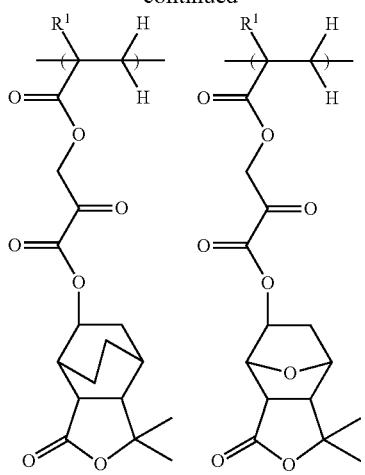
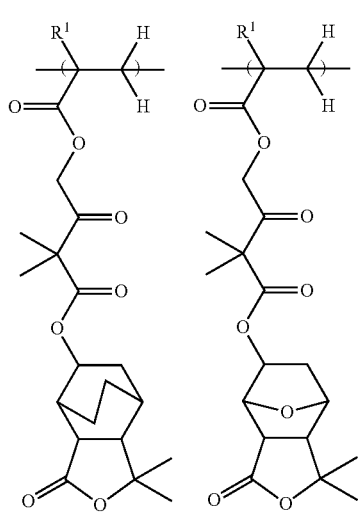
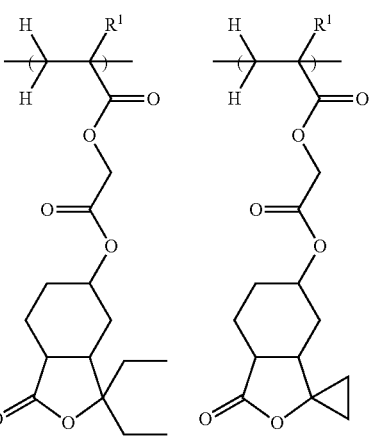
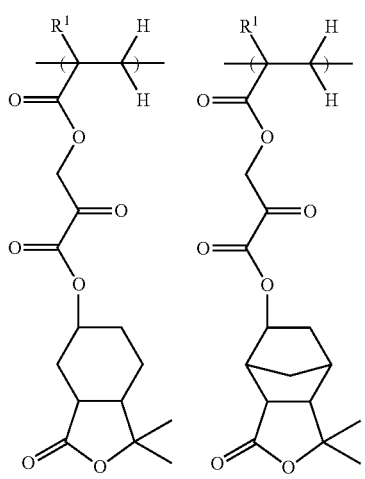
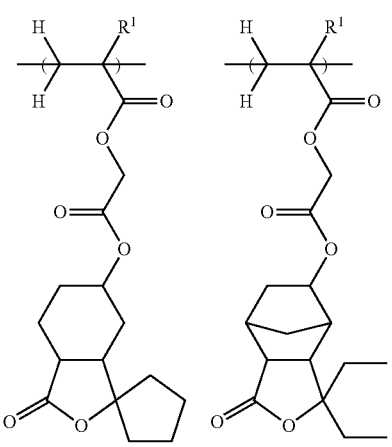

-continued
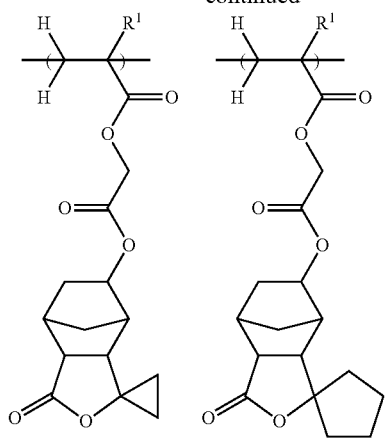
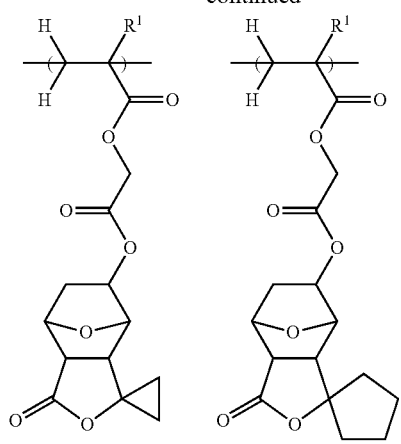
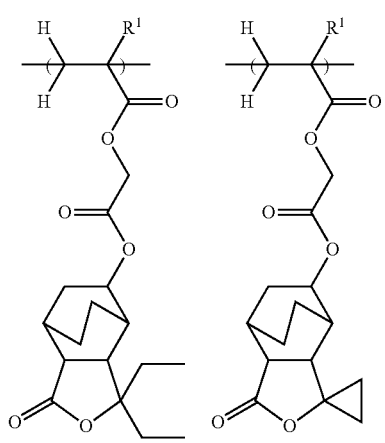
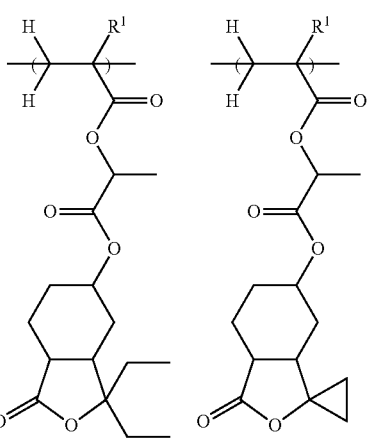
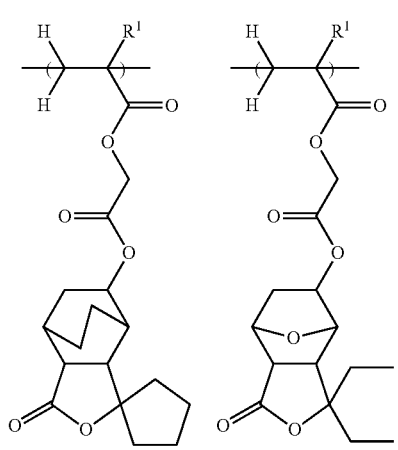
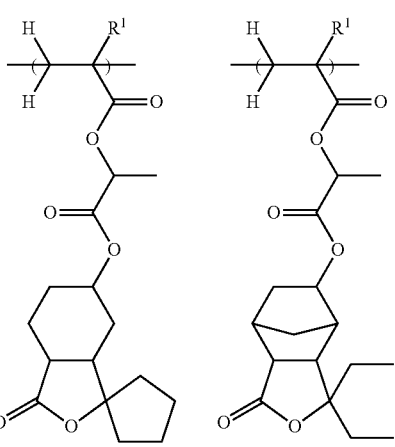

-continued
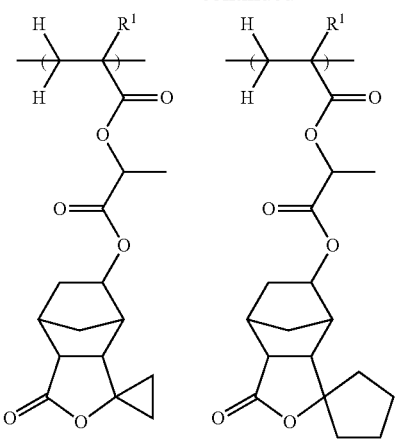
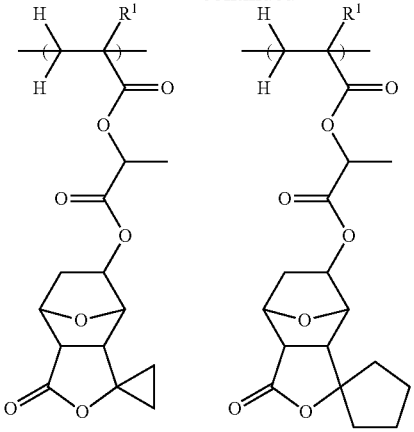
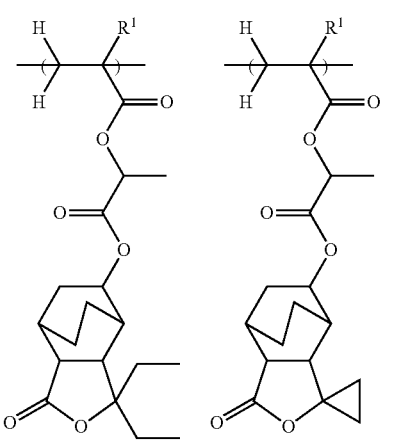
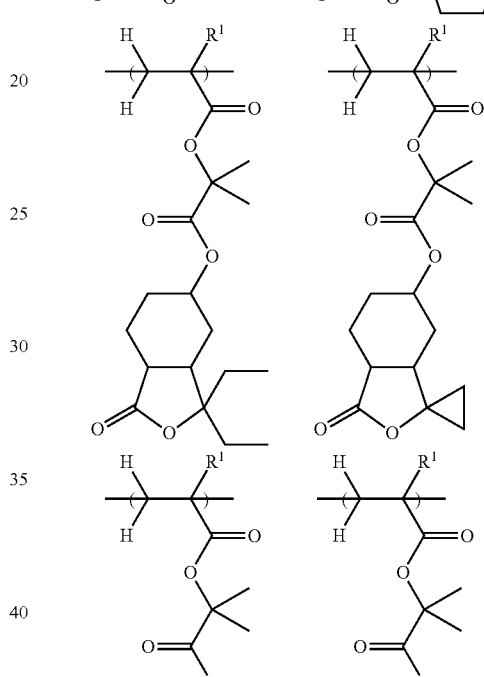
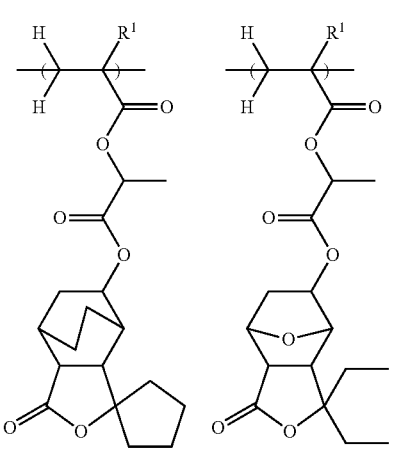
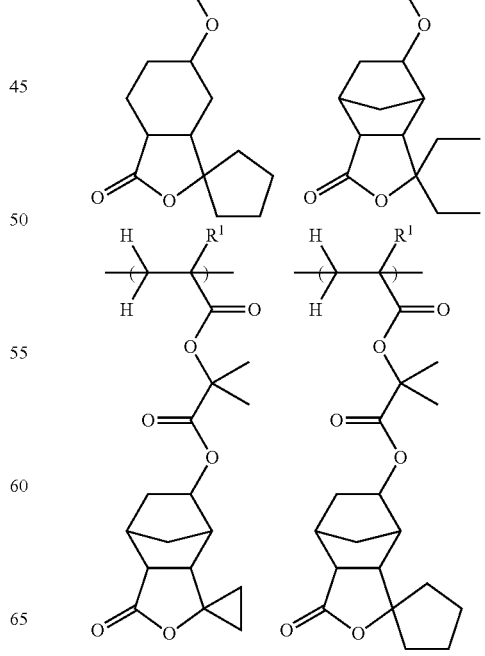

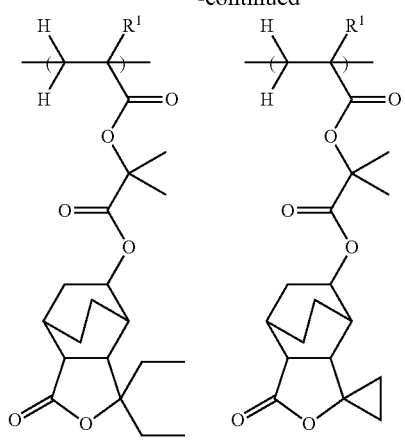
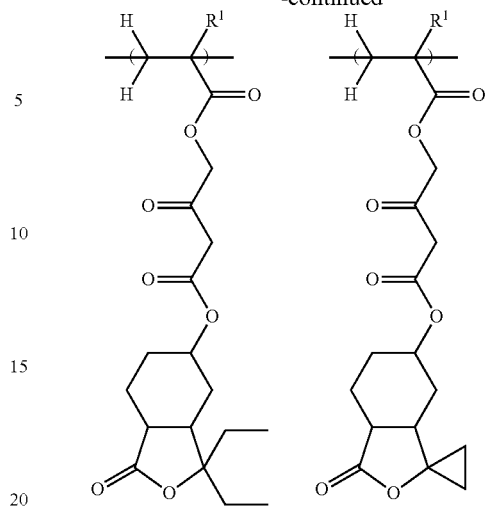
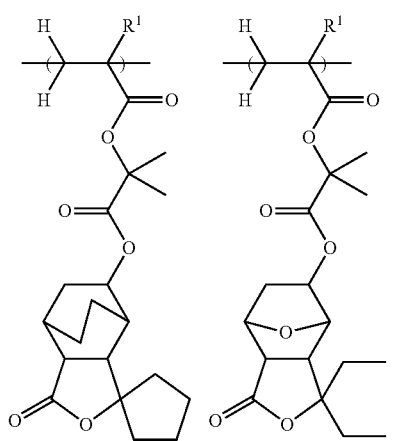
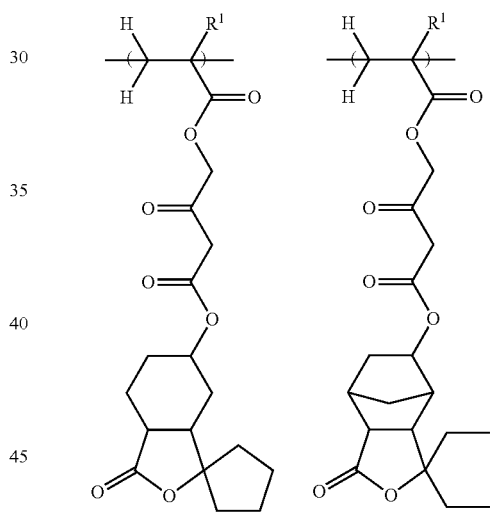
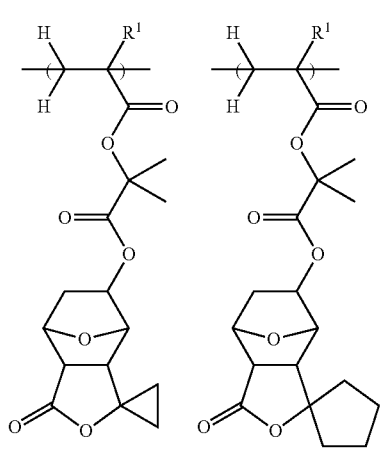
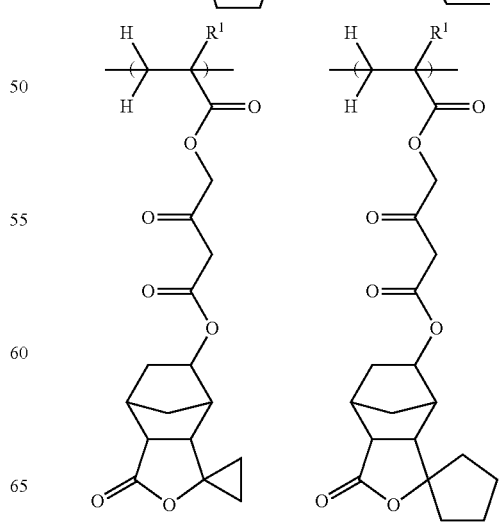

-continued
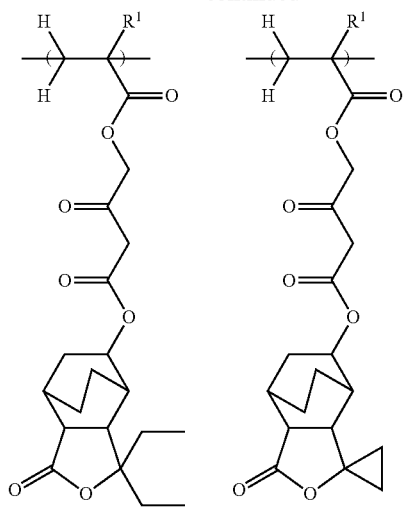
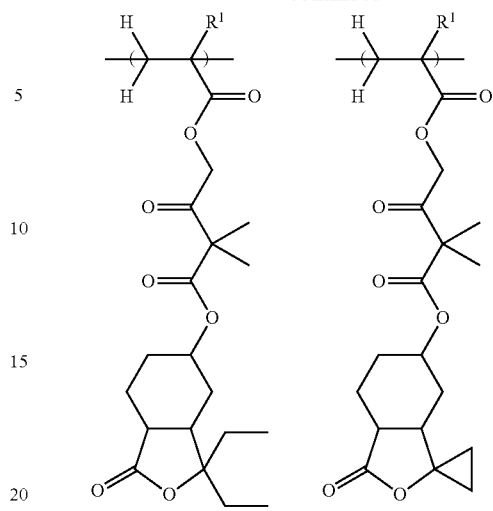
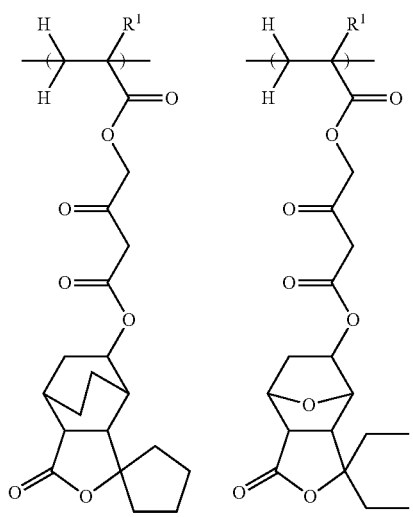
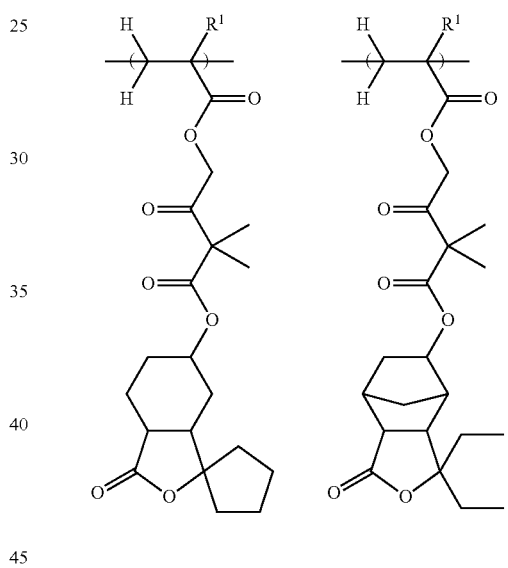
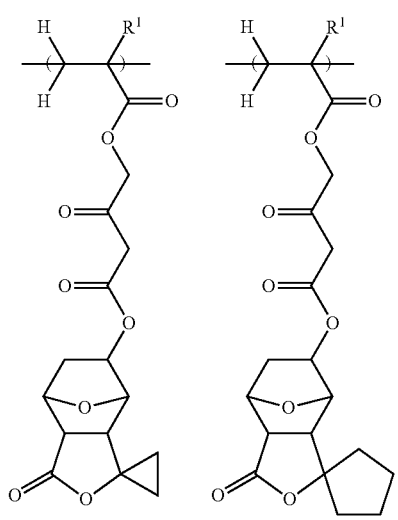
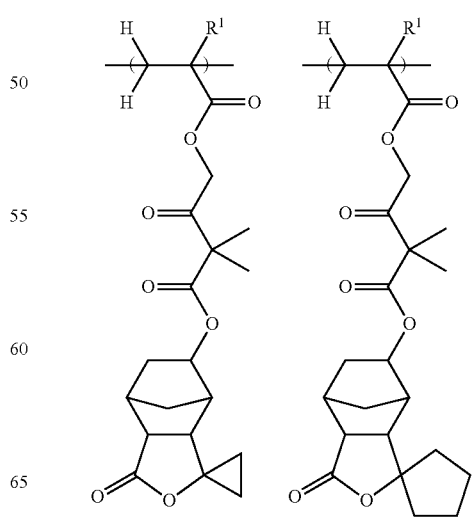

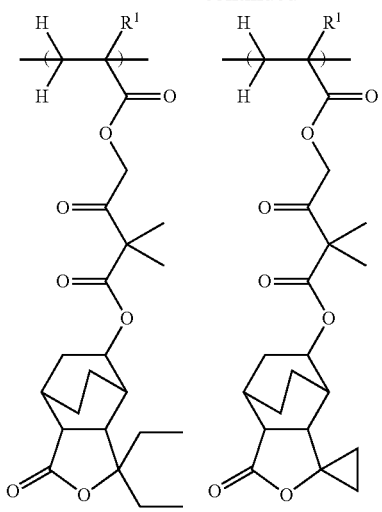
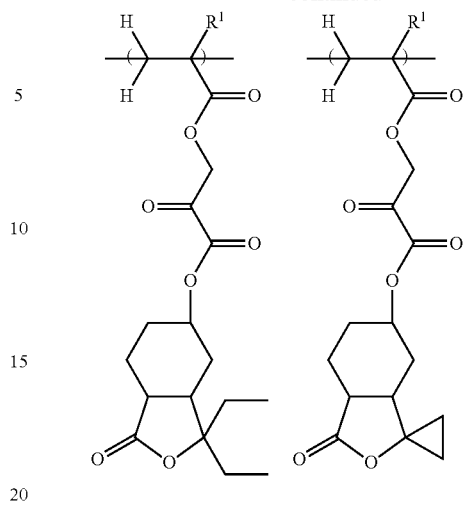
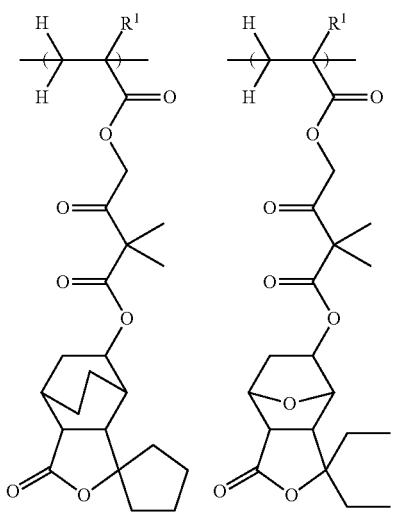
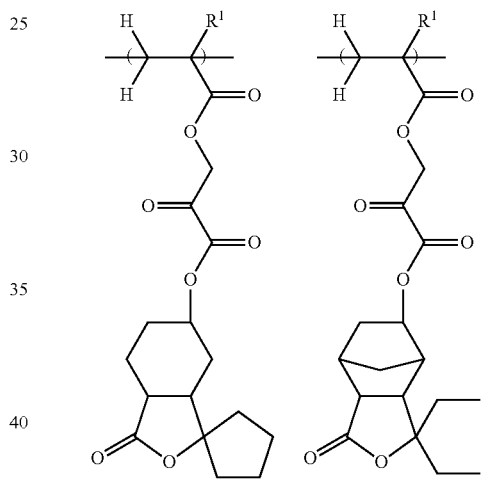
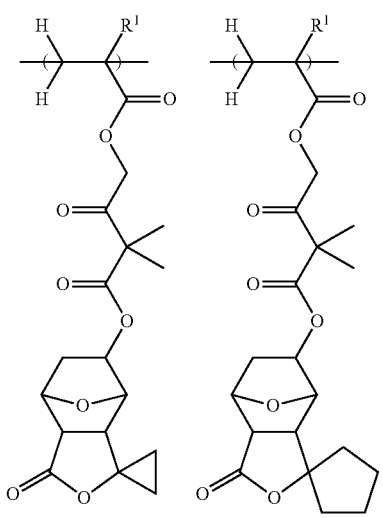
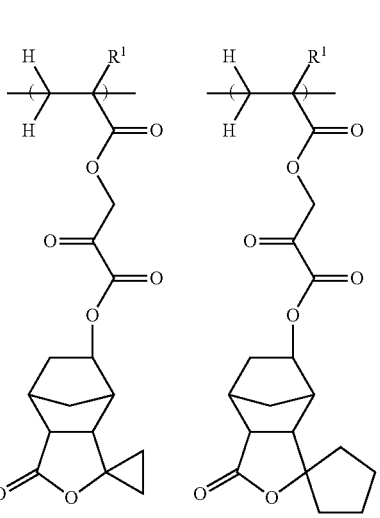

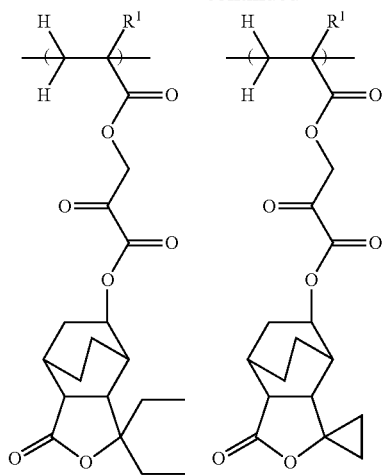
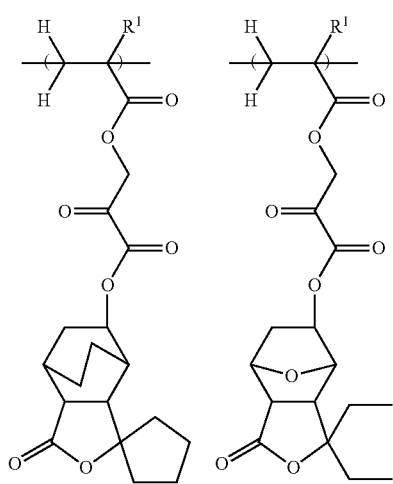
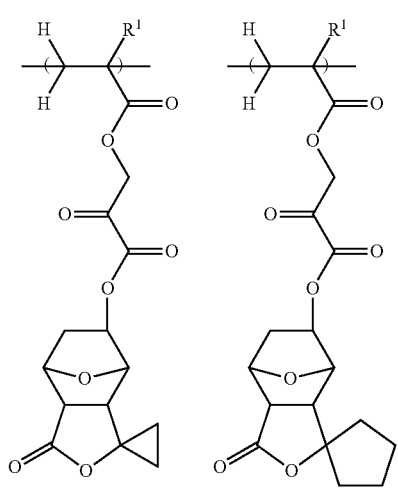
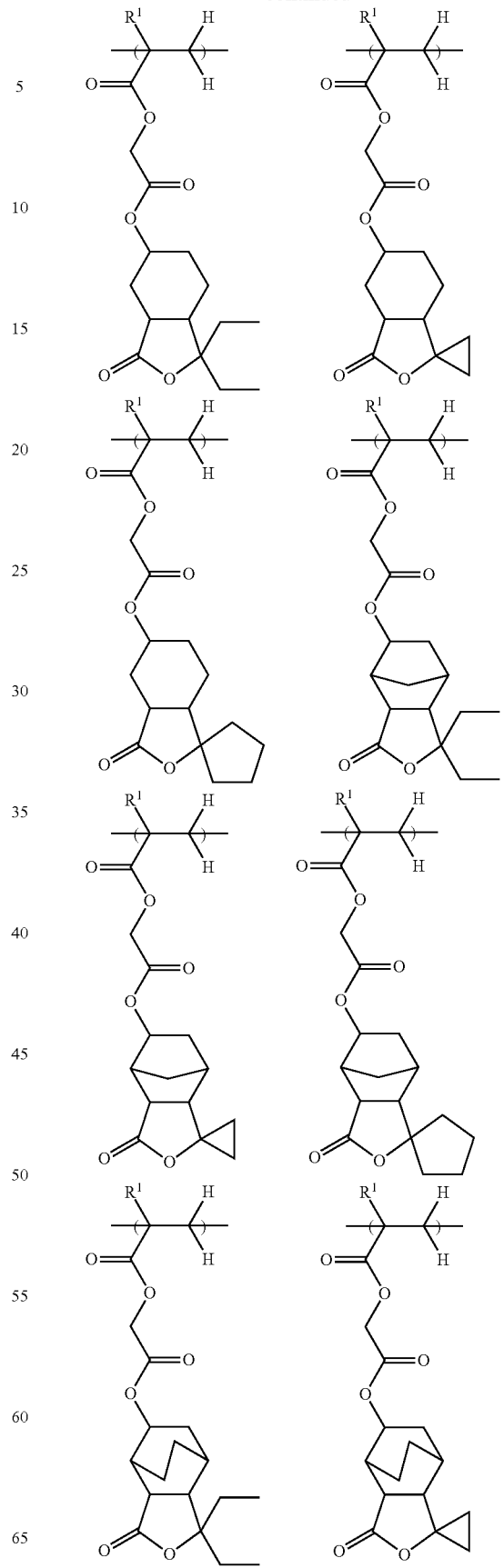

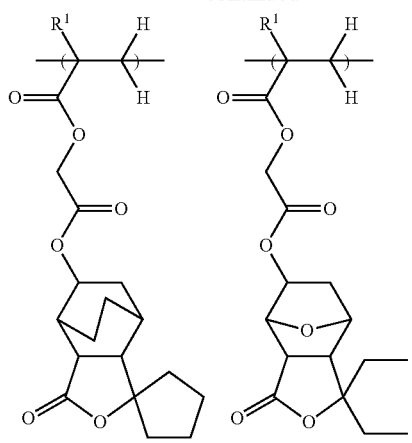
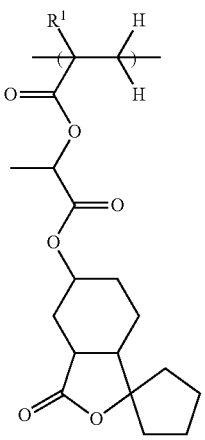
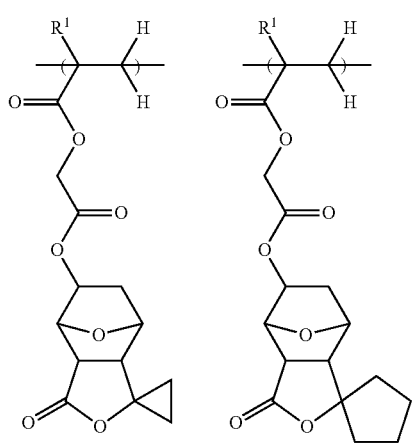
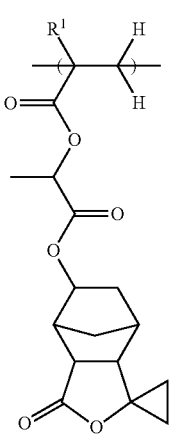
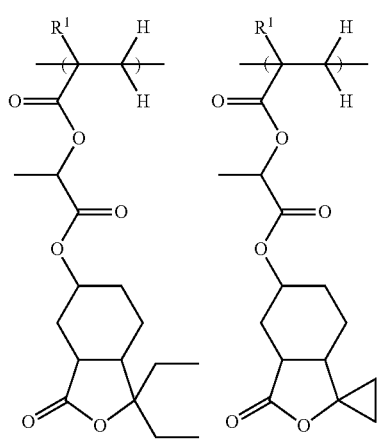
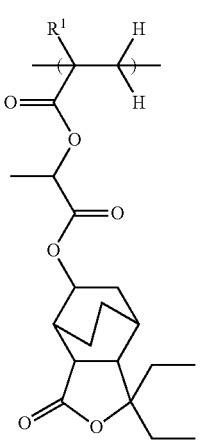

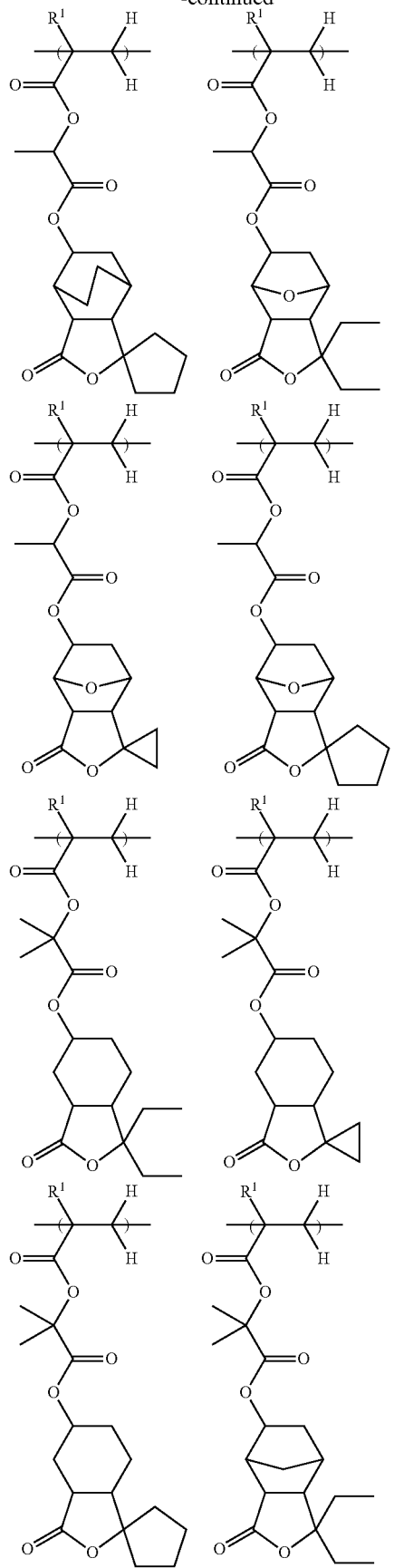
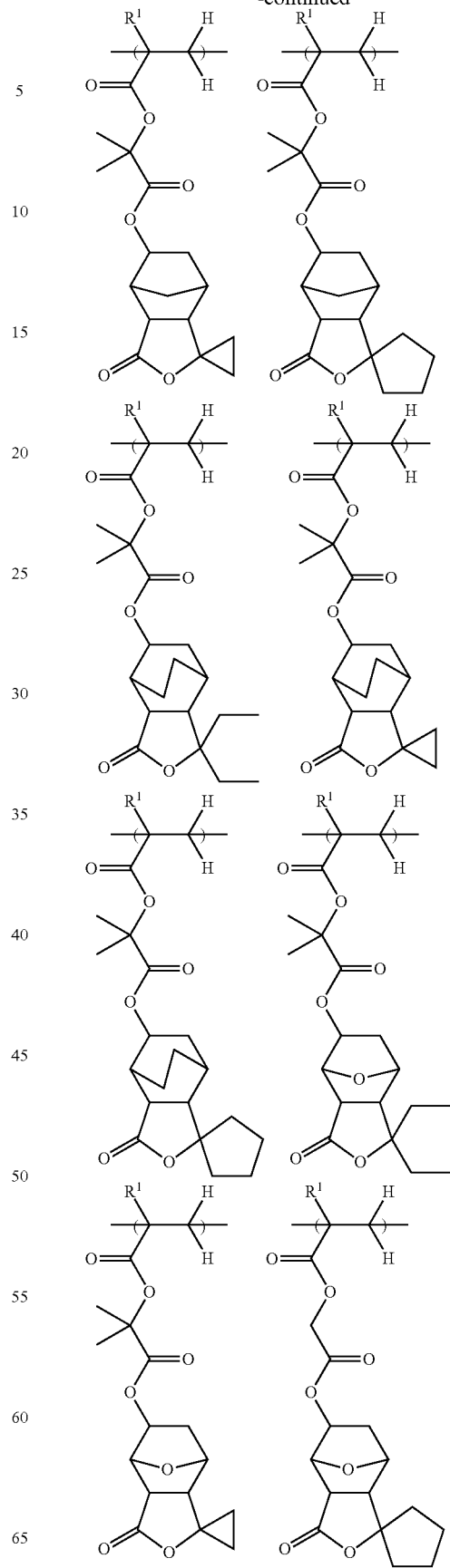

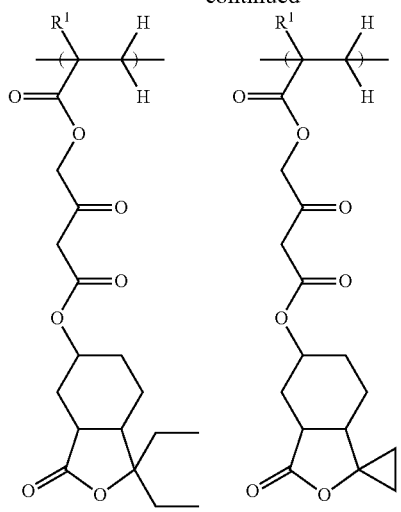
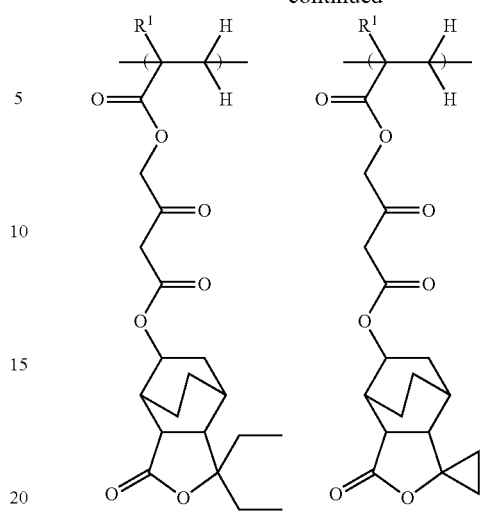
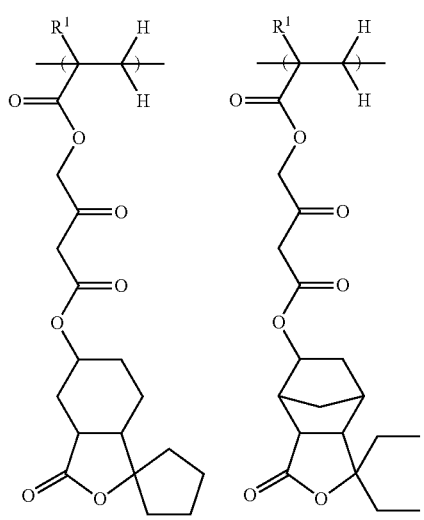
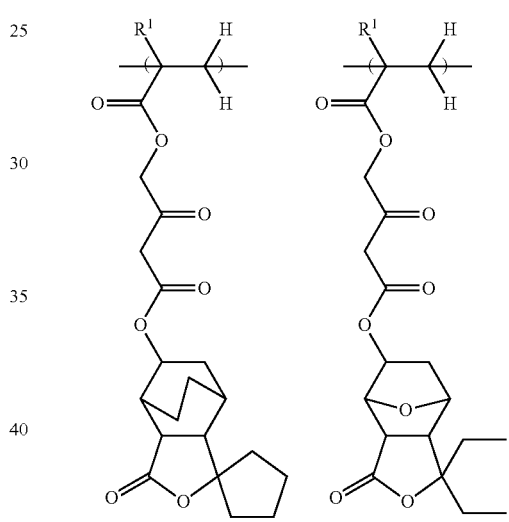
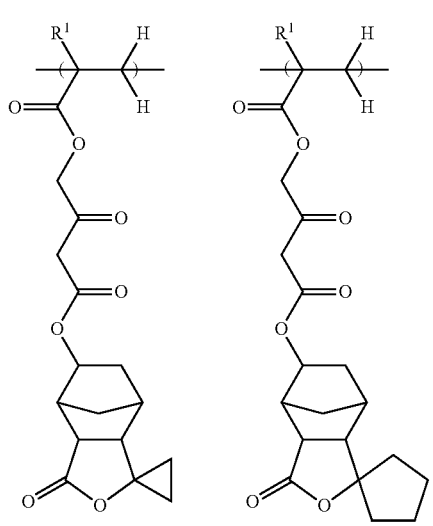
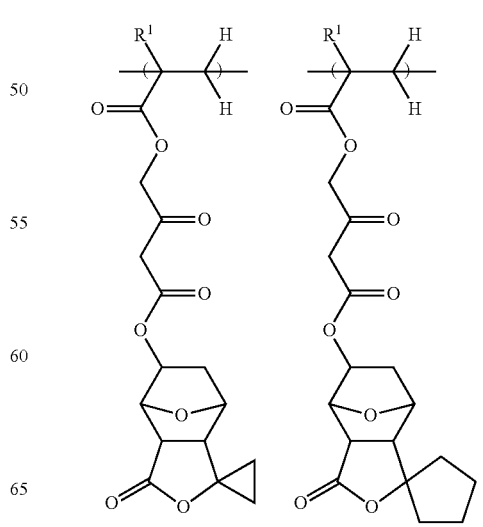

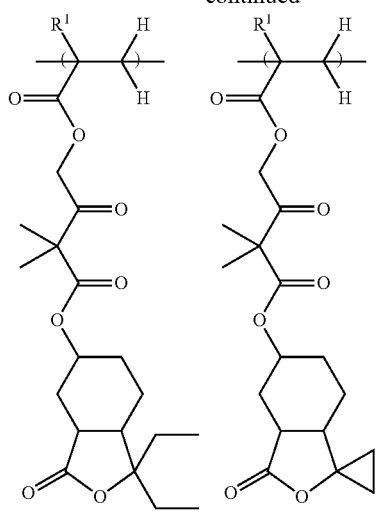
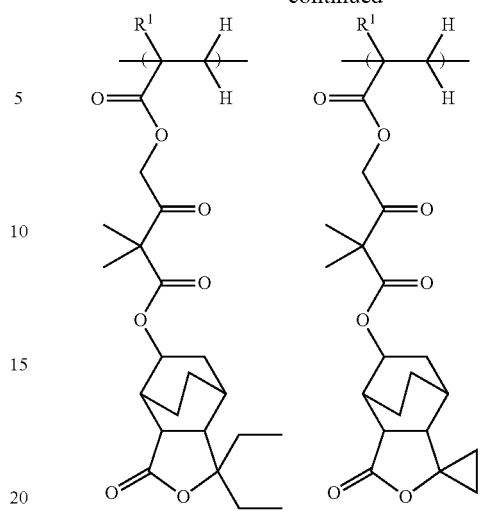
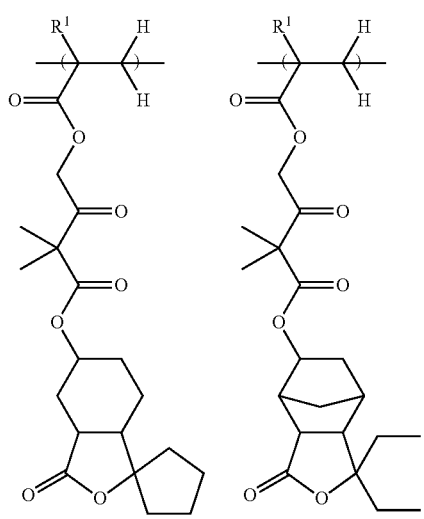
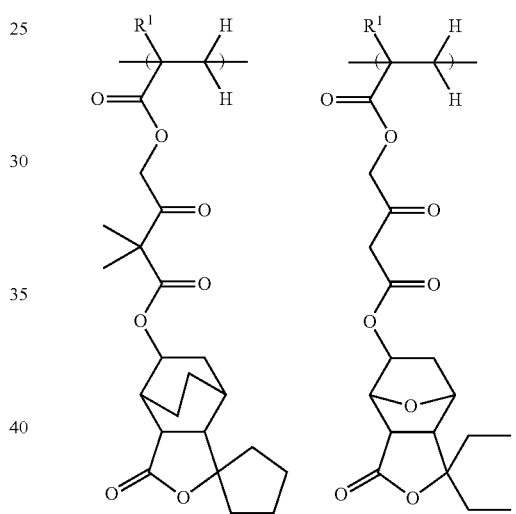
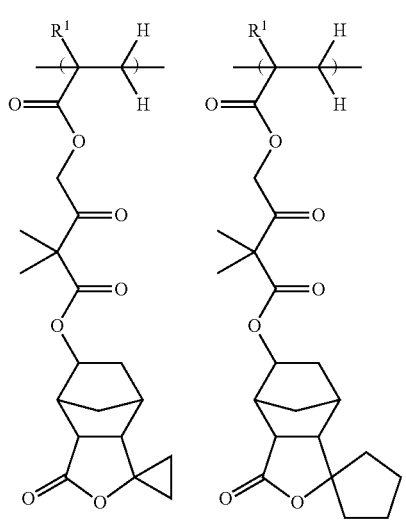
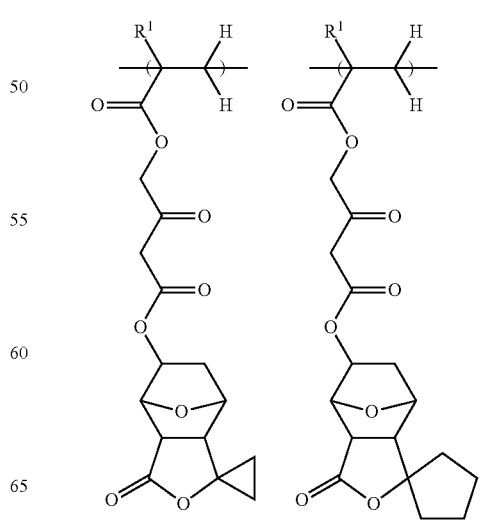

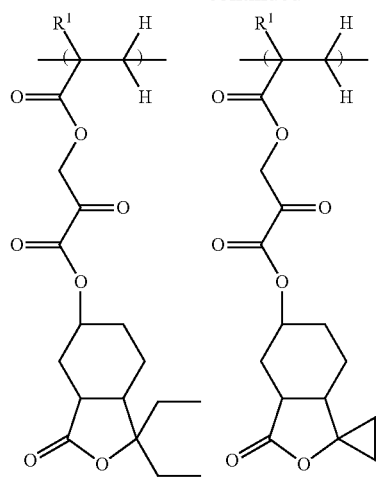
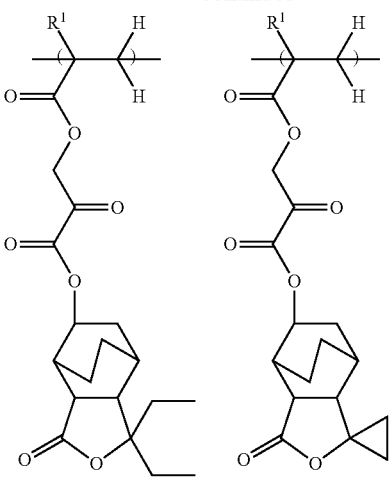
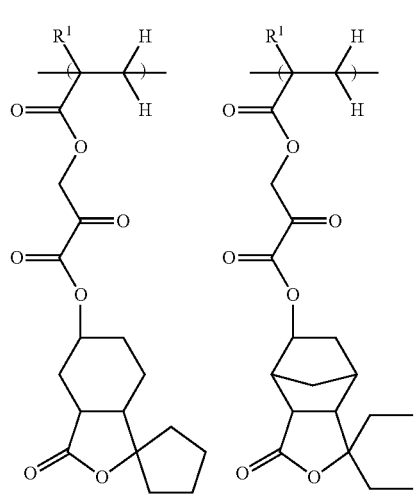
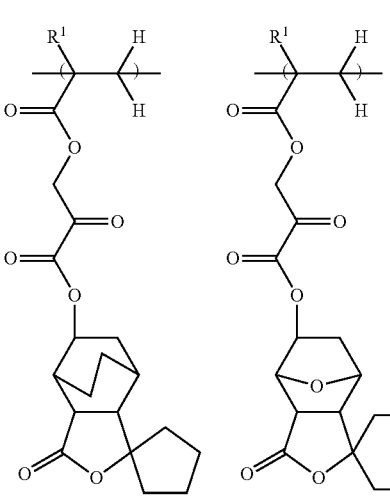
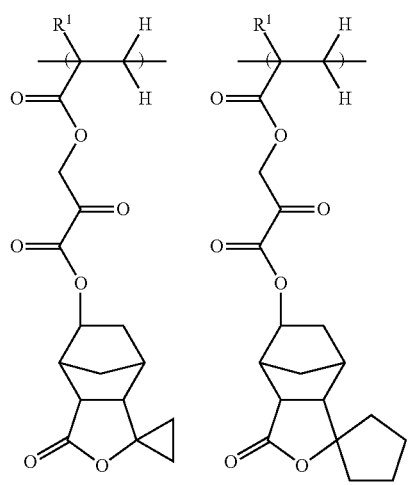
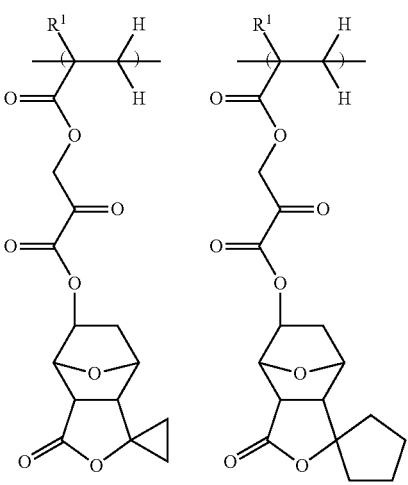

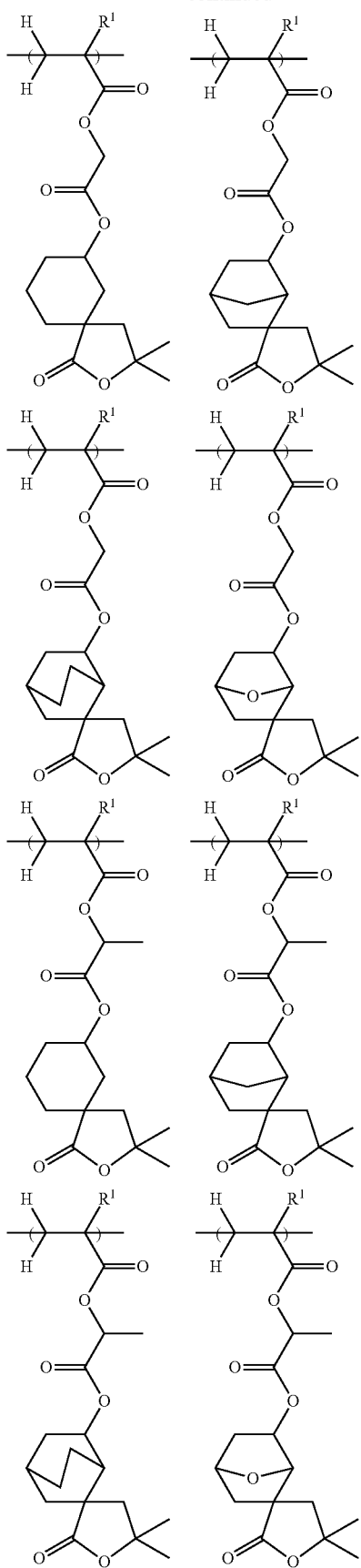
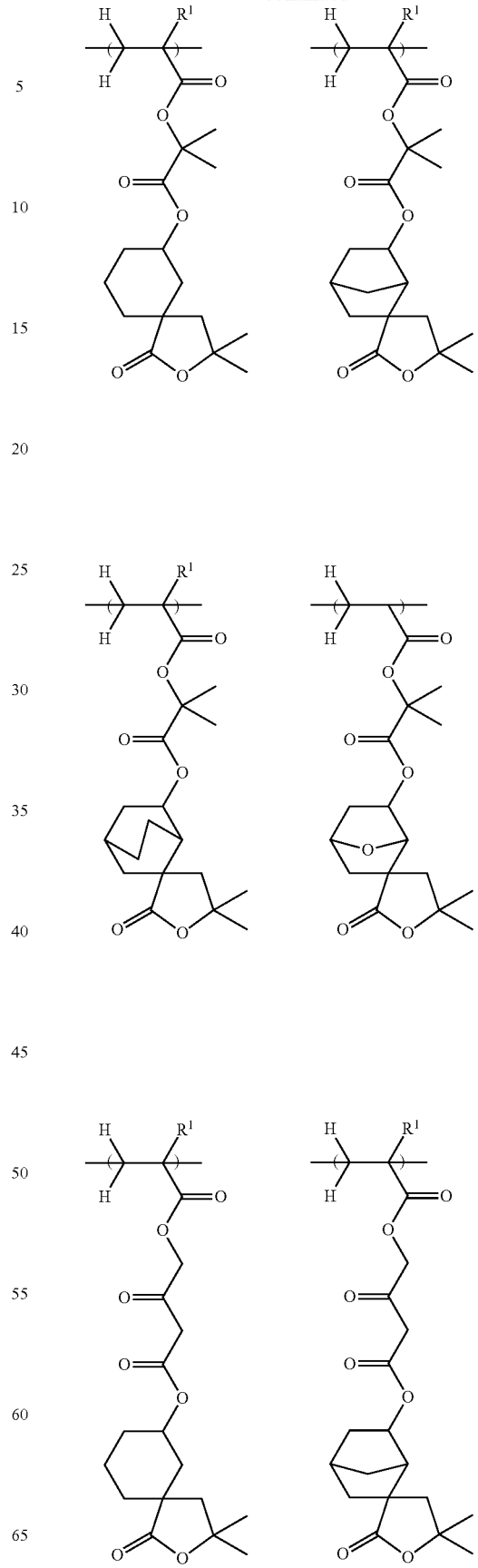

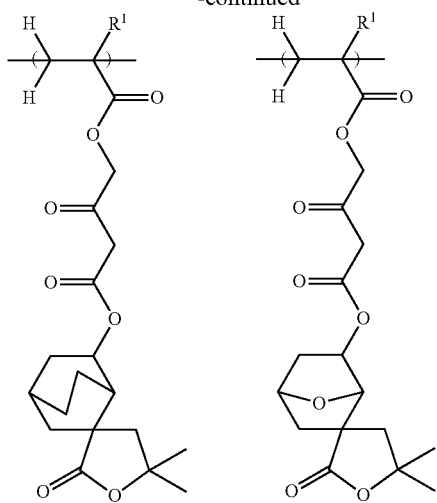
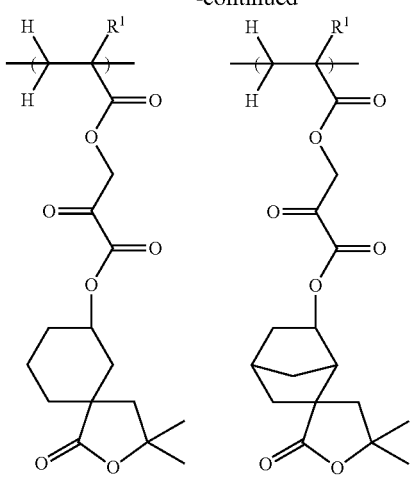
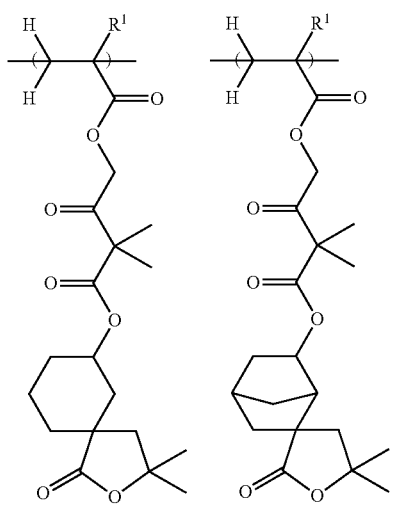
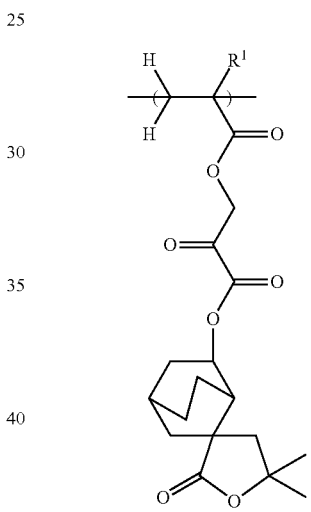
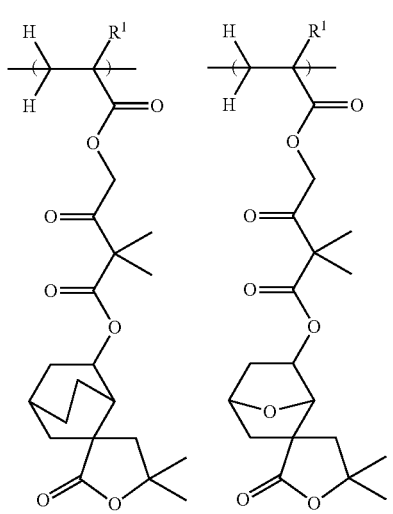
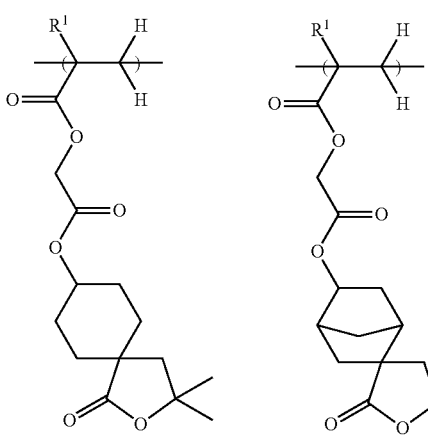

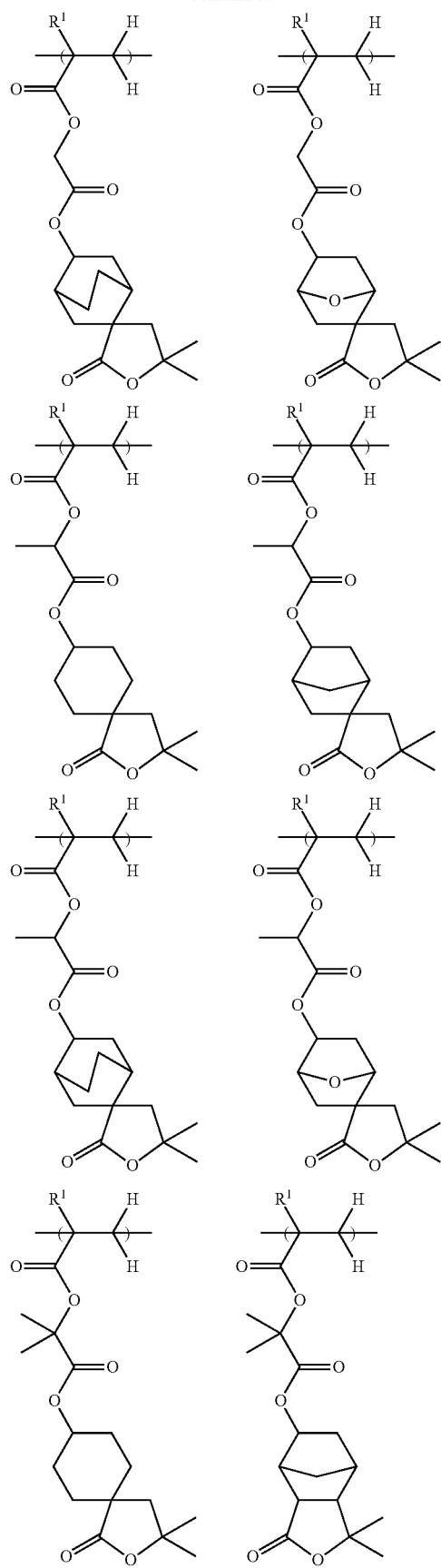
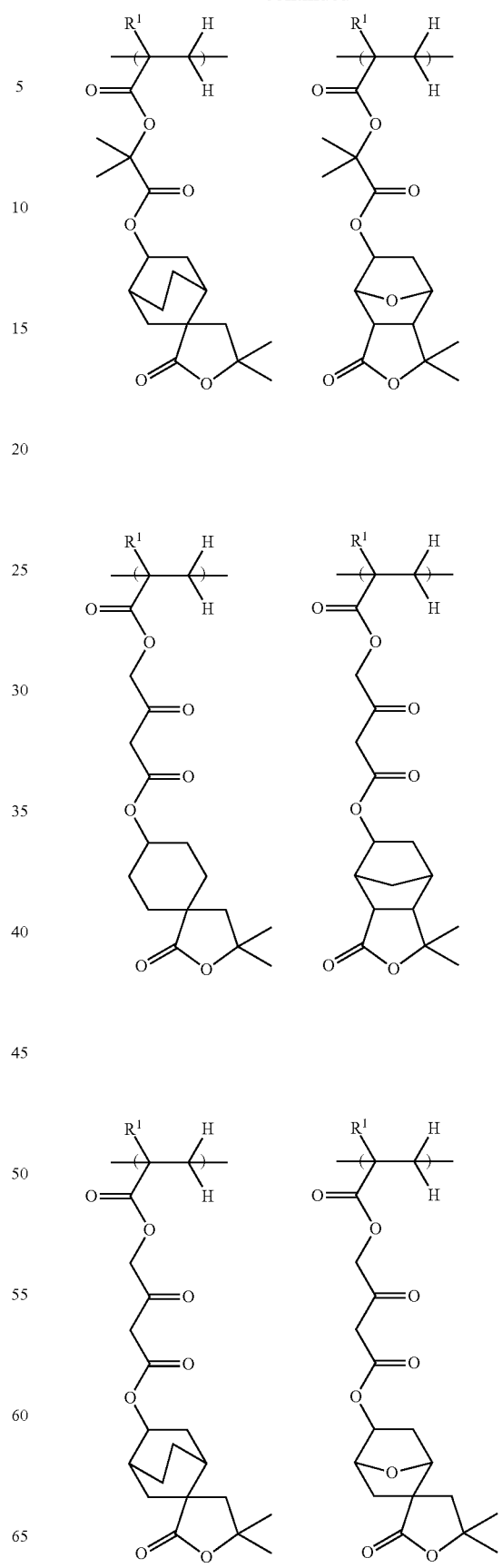

-continued
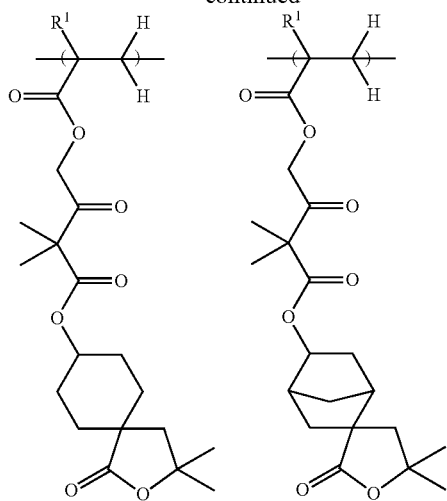
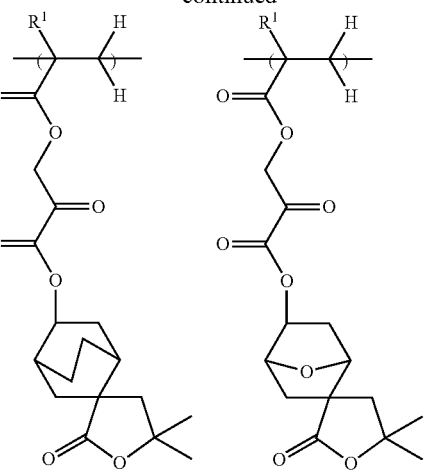
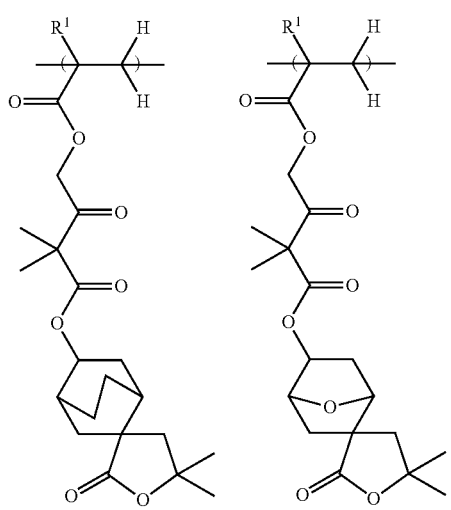
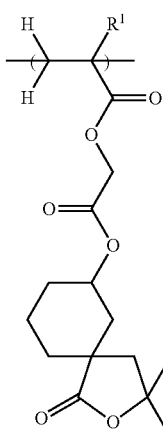
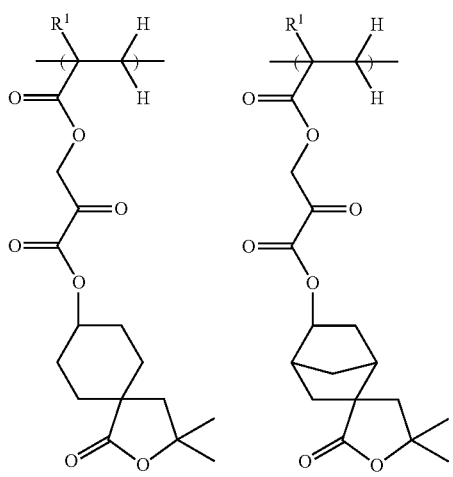
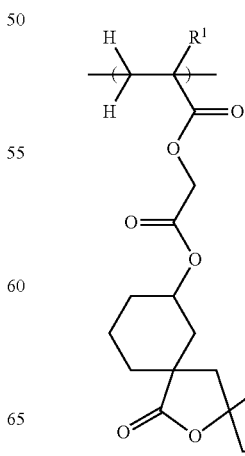

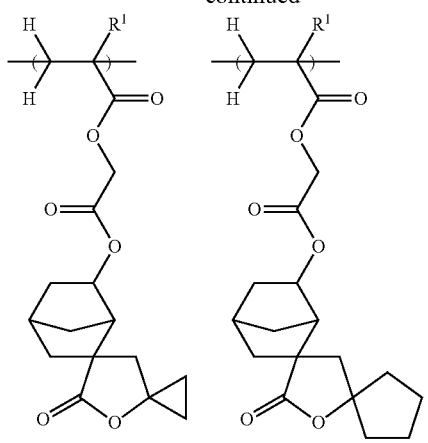
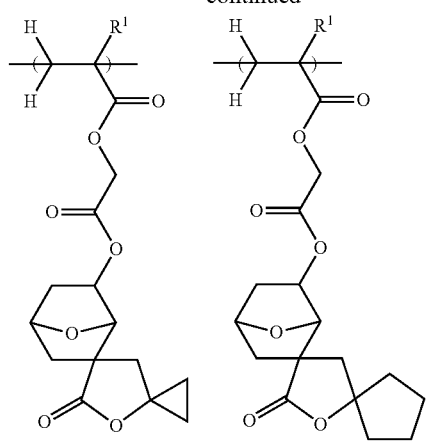
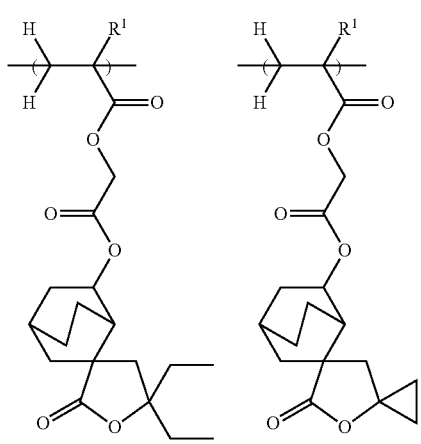
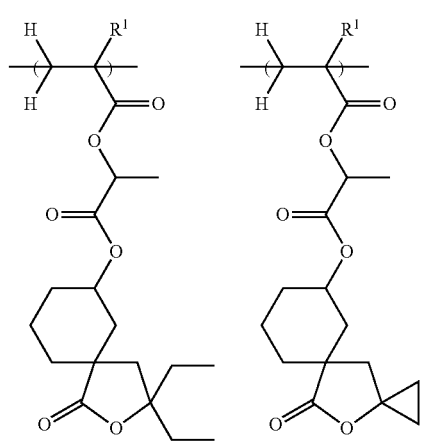
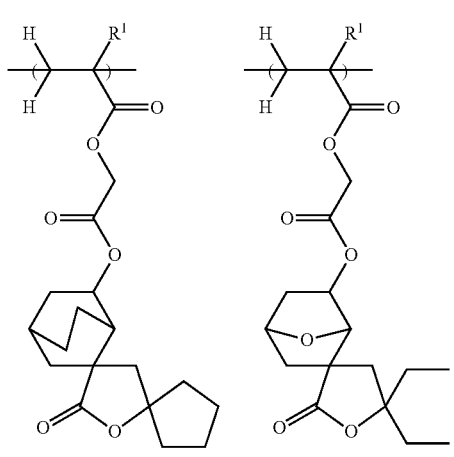
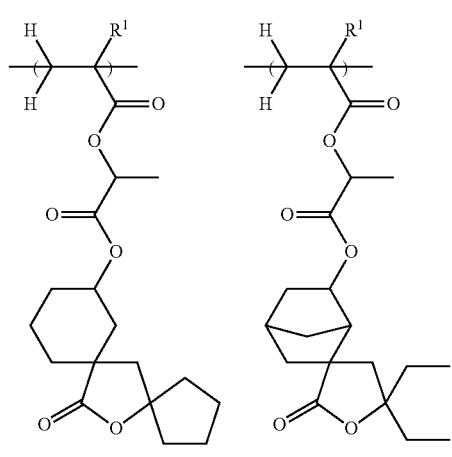

-continued
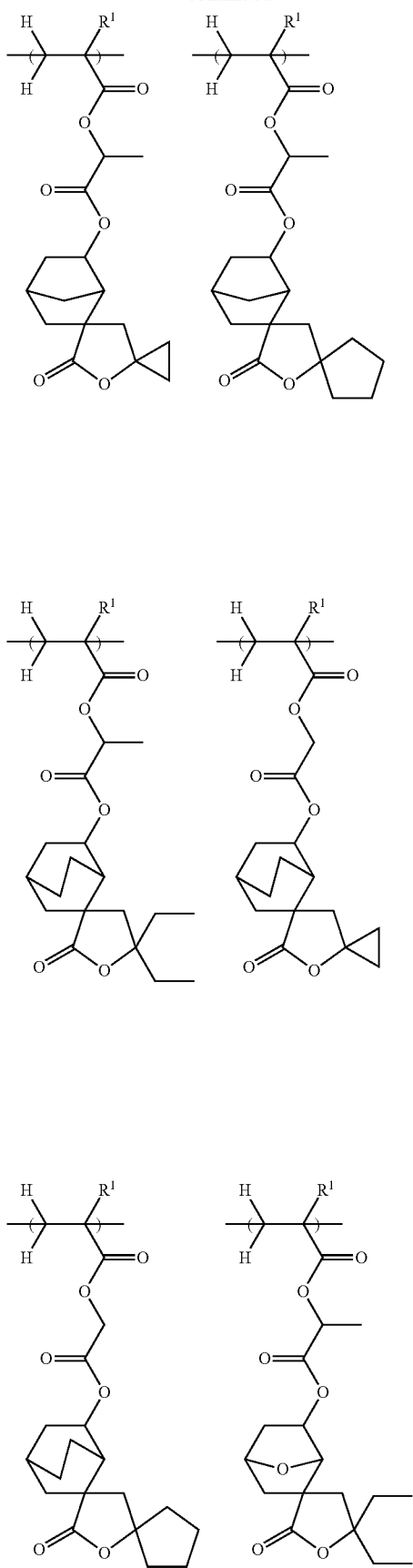
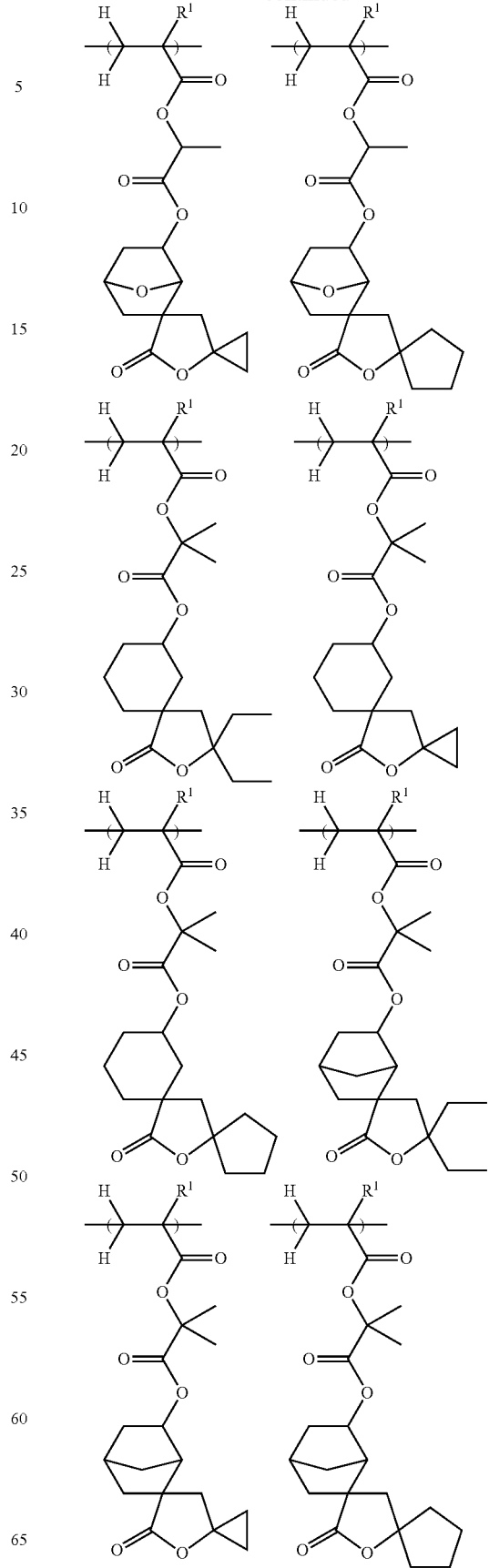

-continued
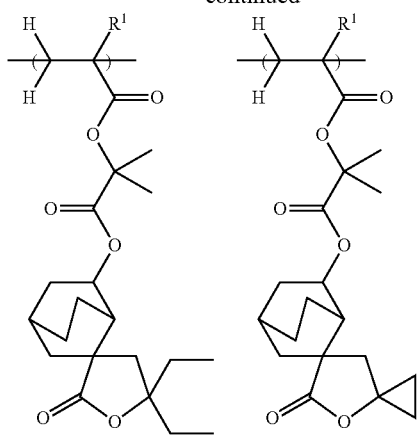
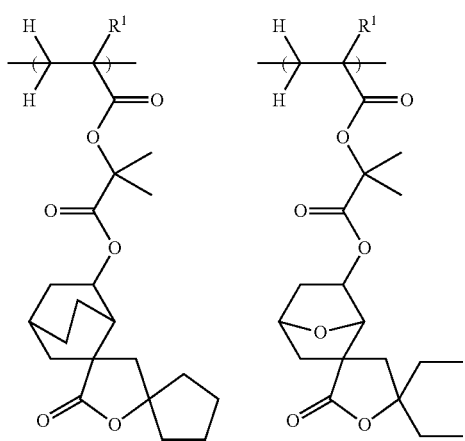
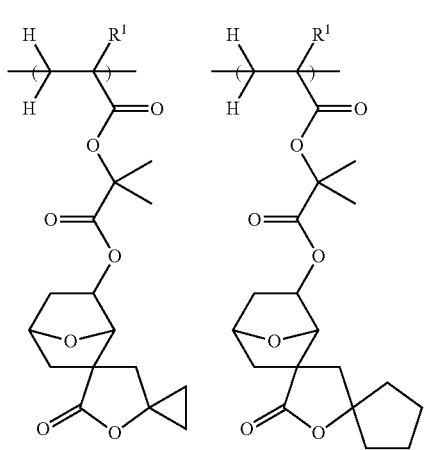
-continued
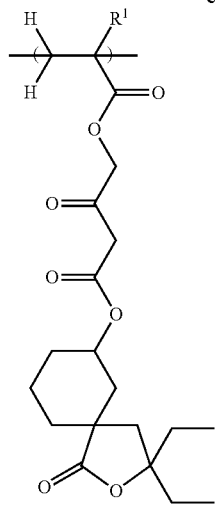
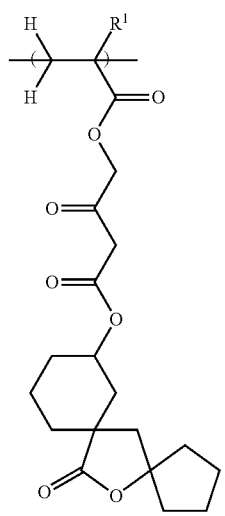
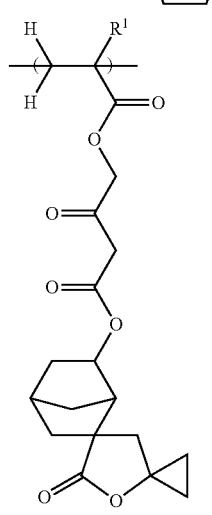

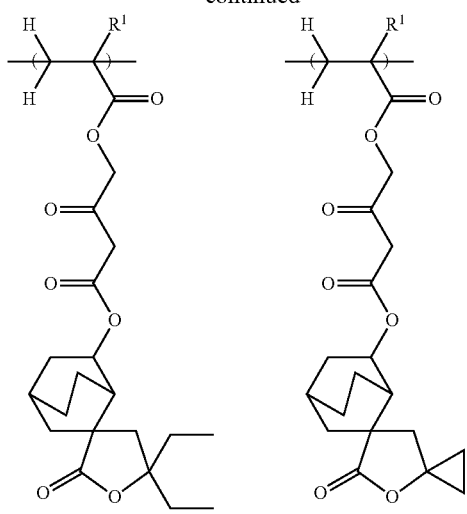
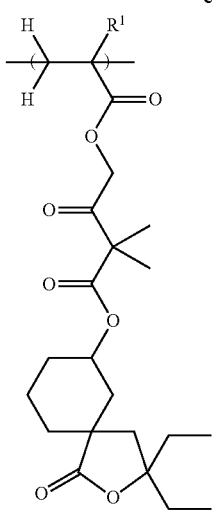
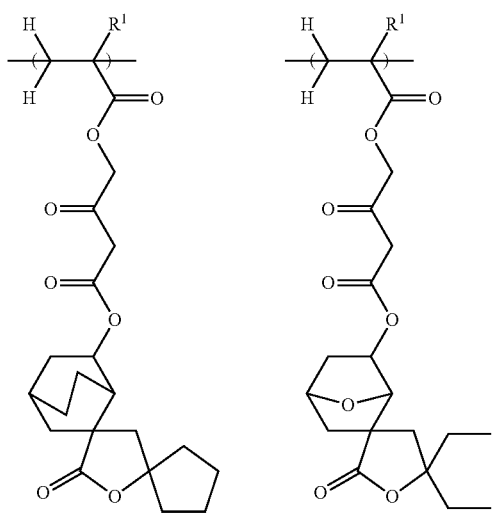
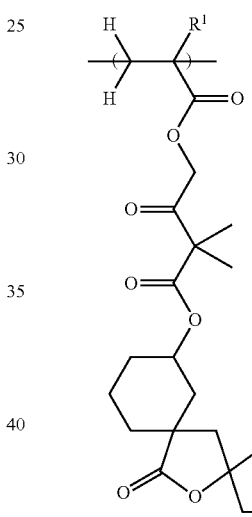
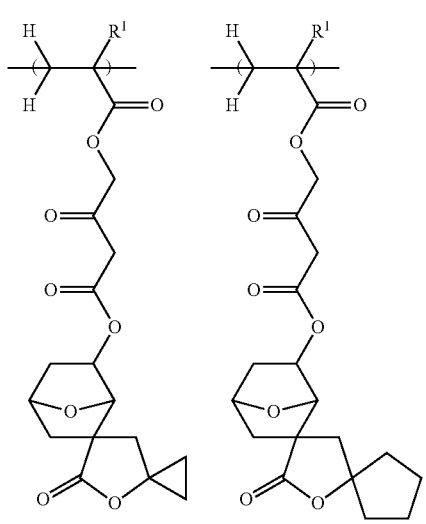
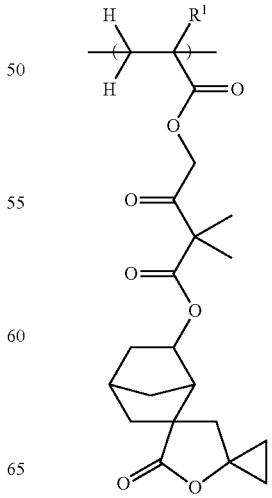

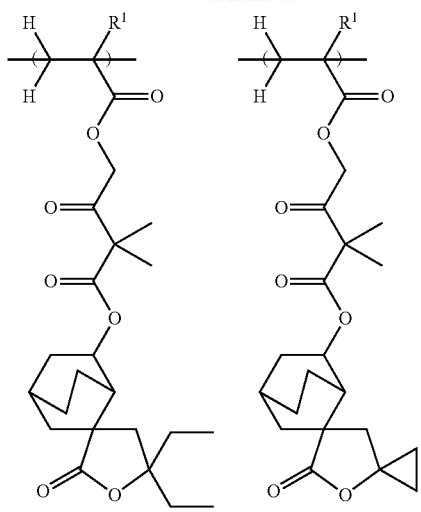
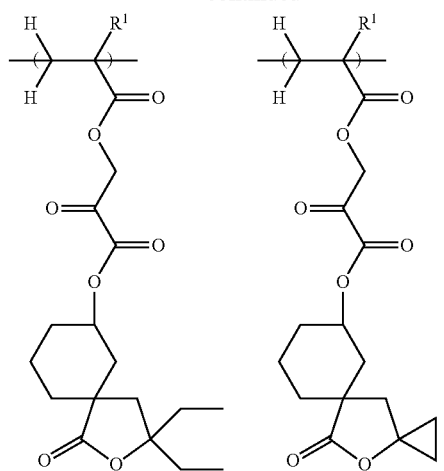
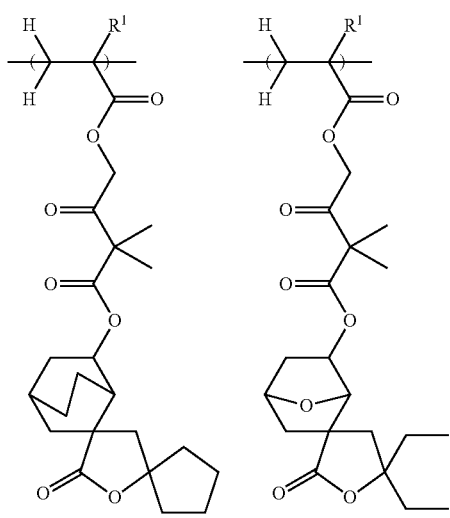
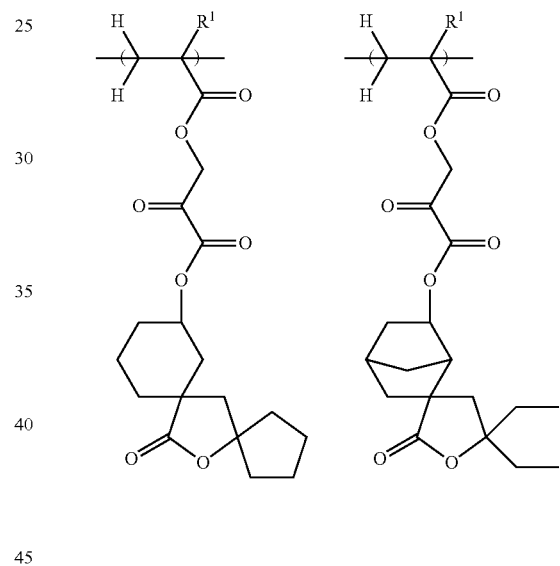
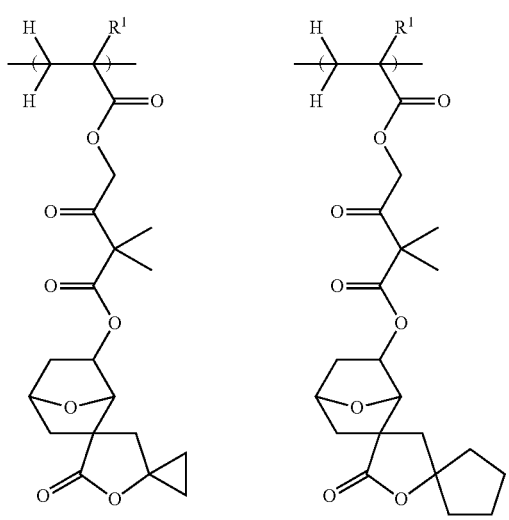
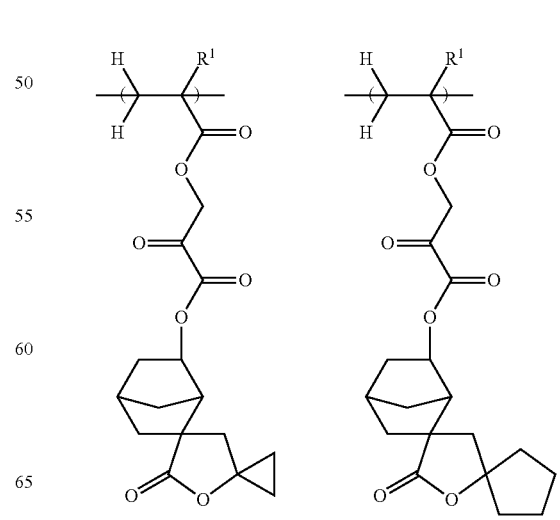

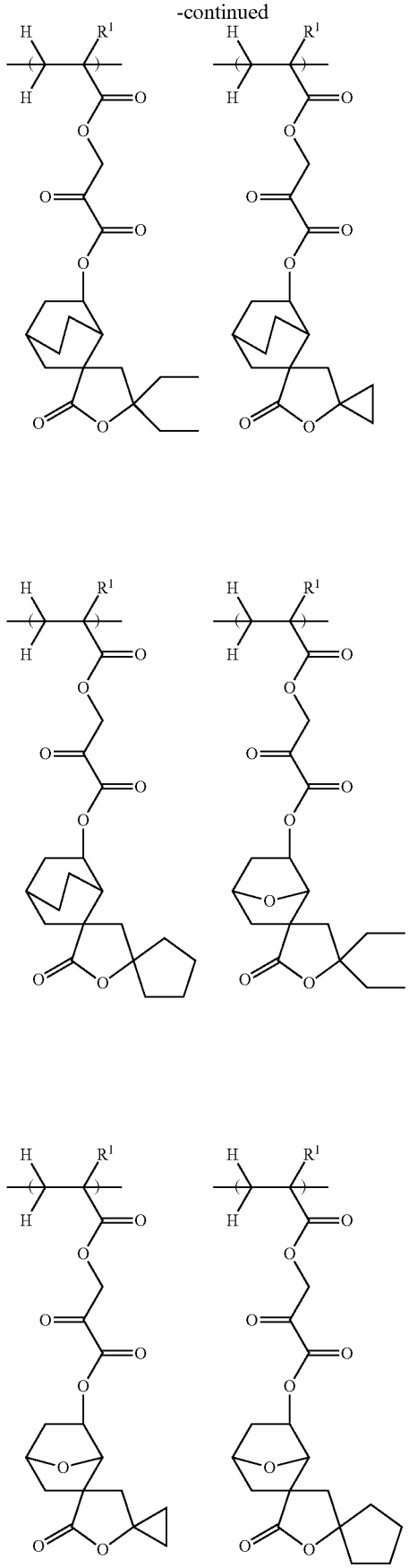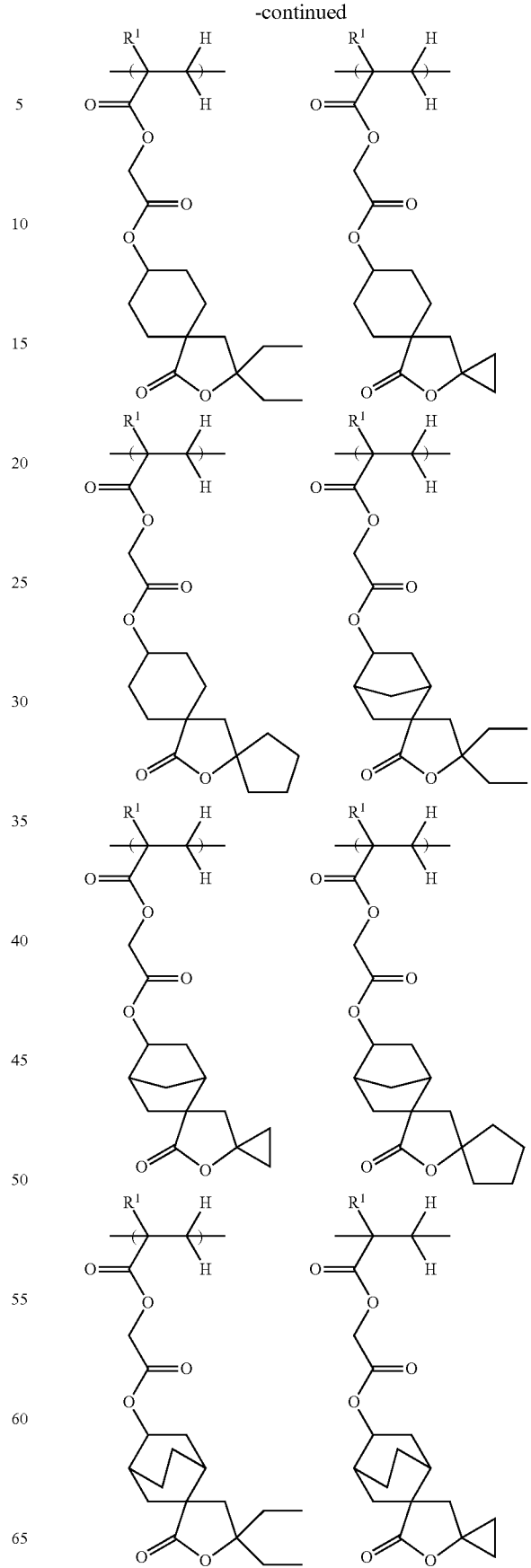

61
-continued
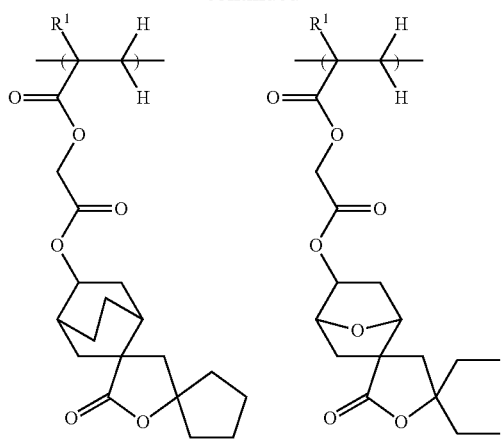
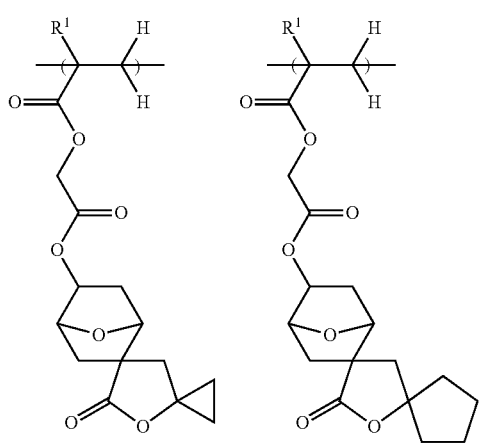
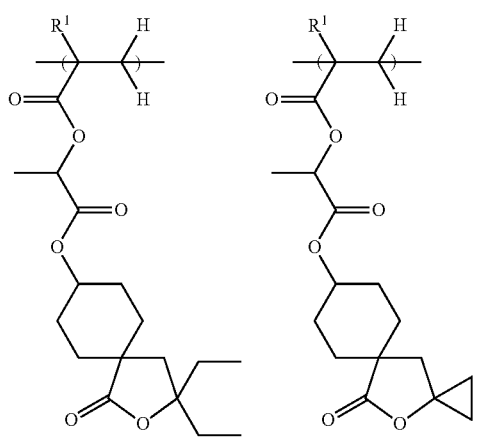
62
-continued
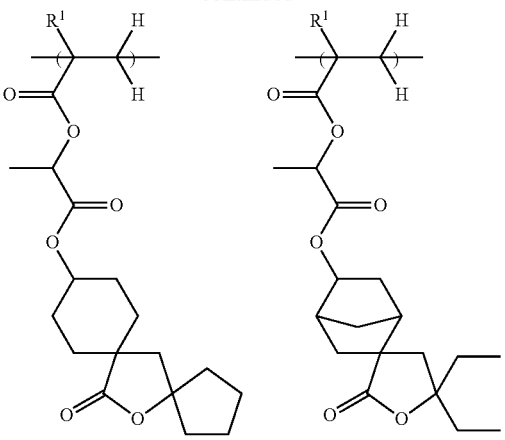
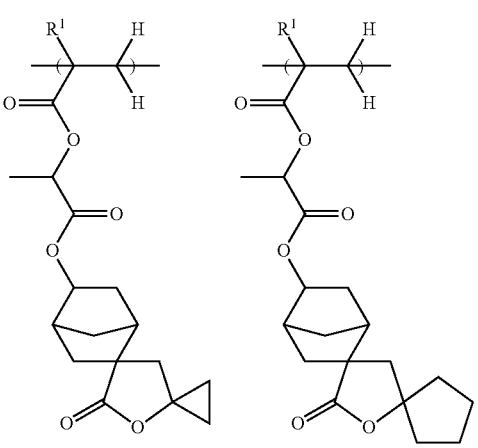
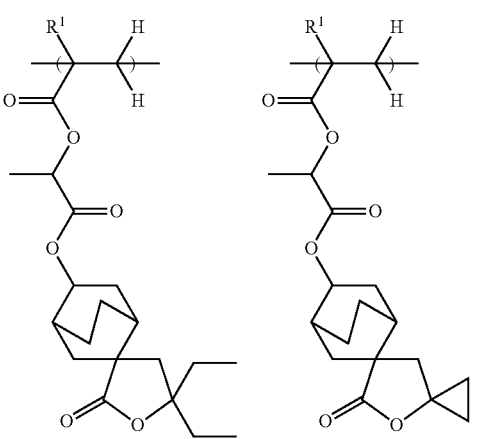

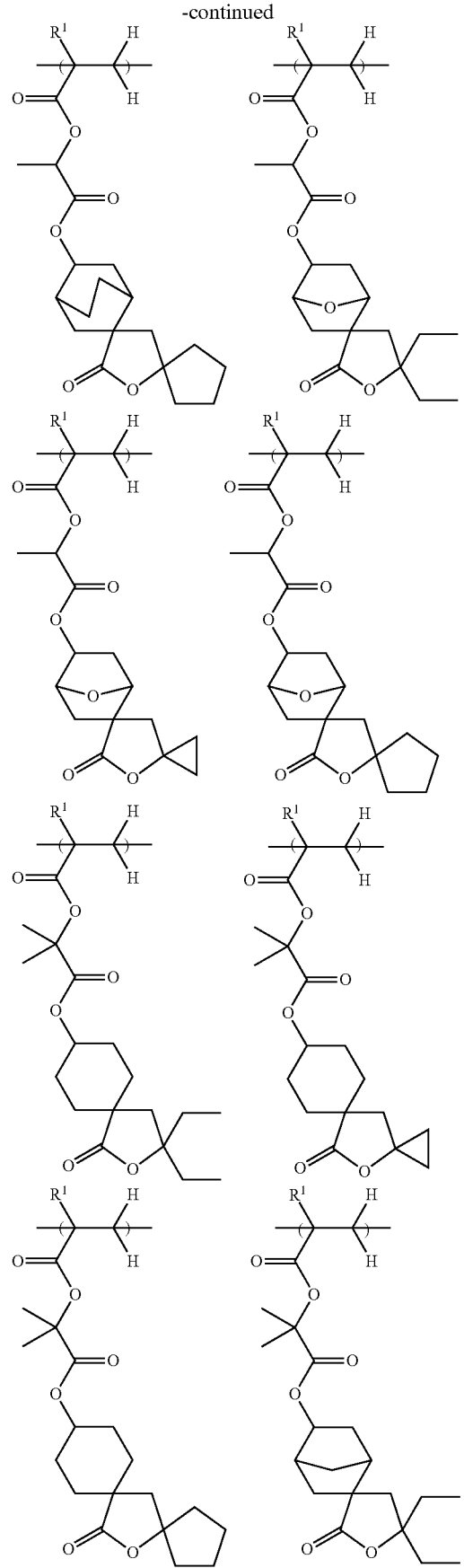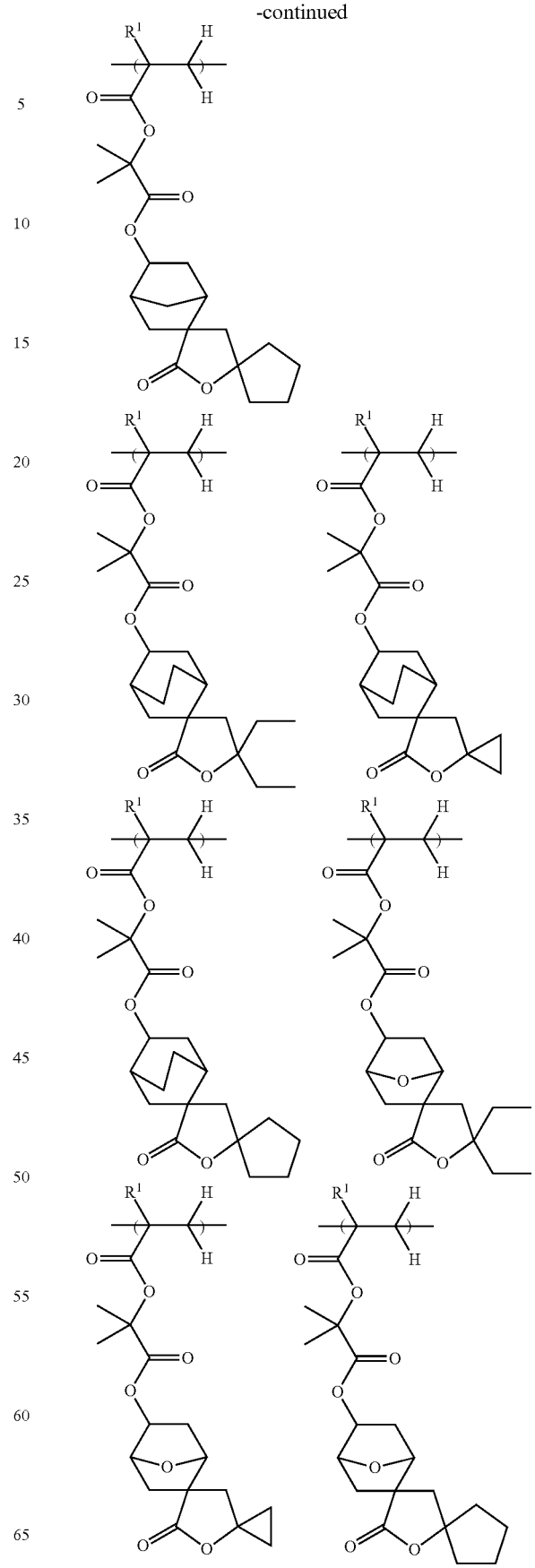

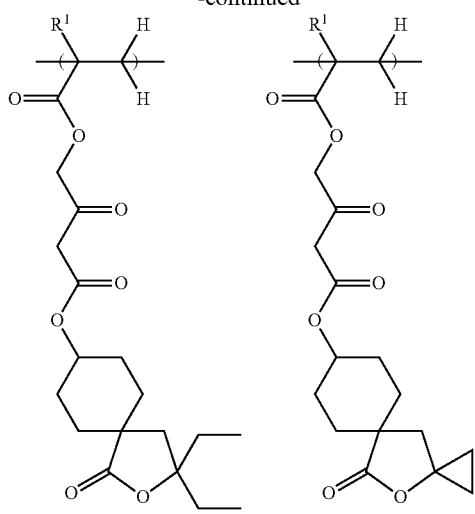
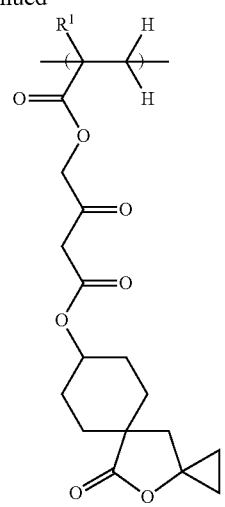
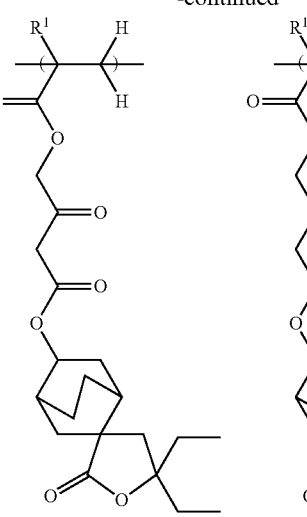
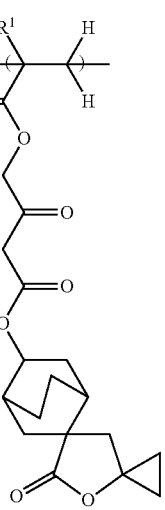
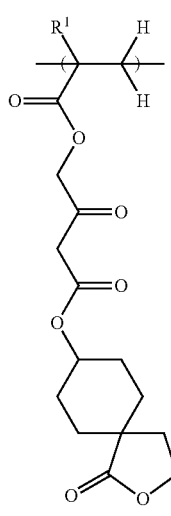
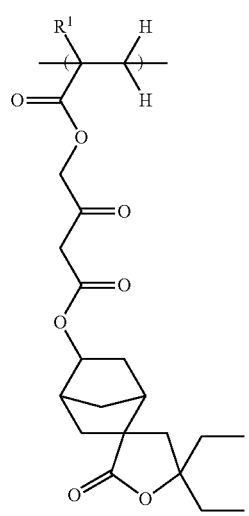
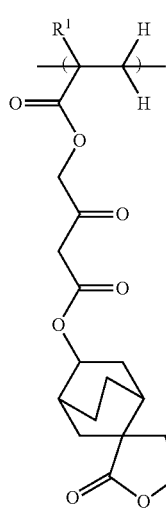
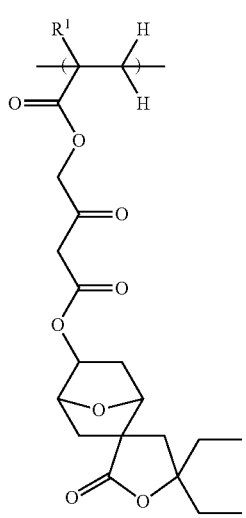
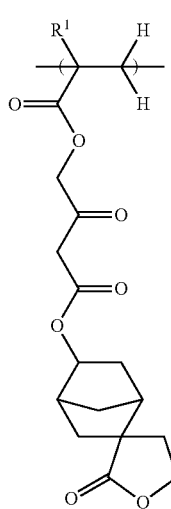
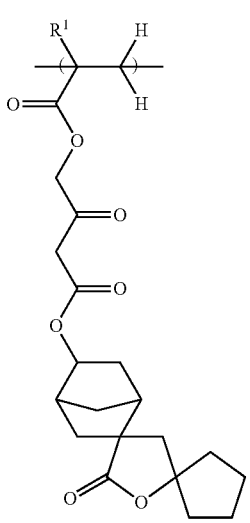
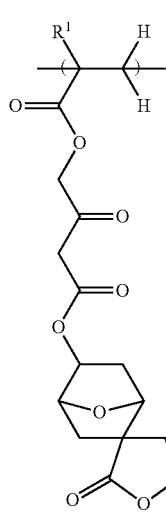
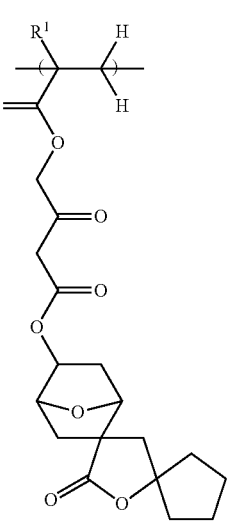

-continued
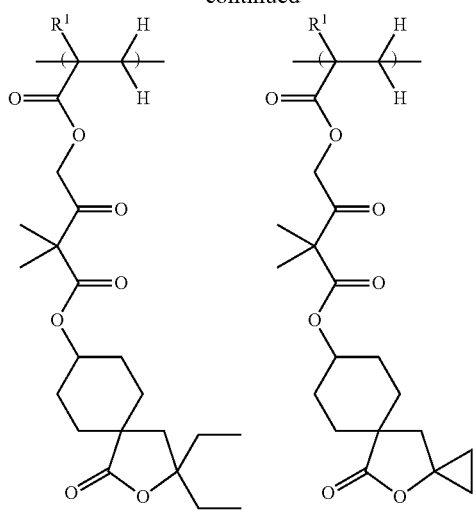
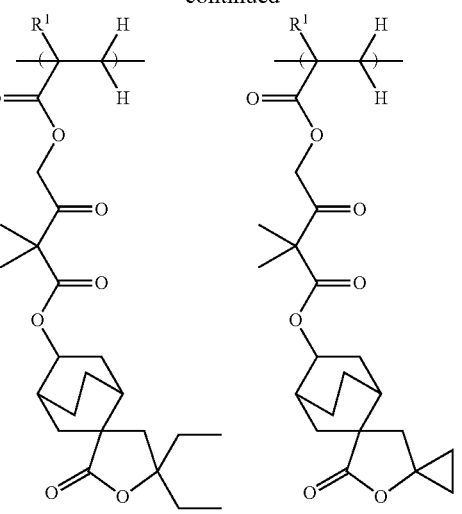
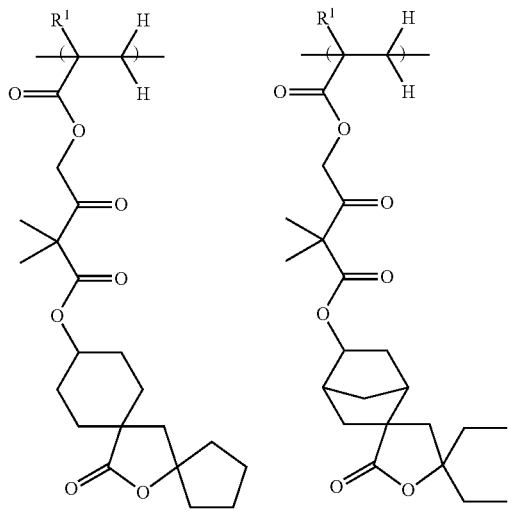
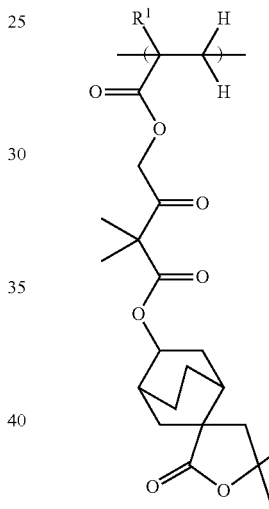
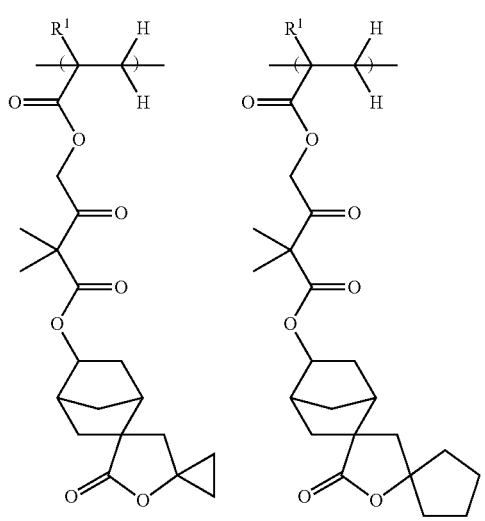
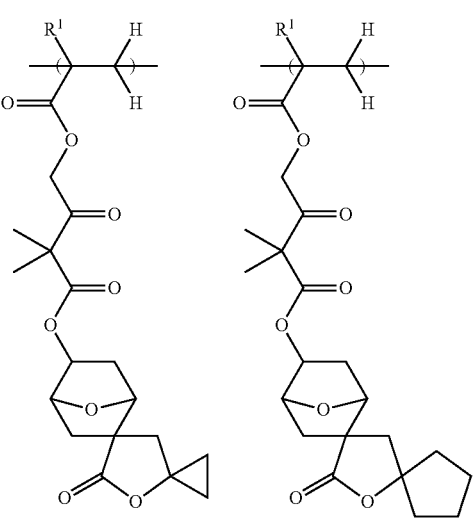

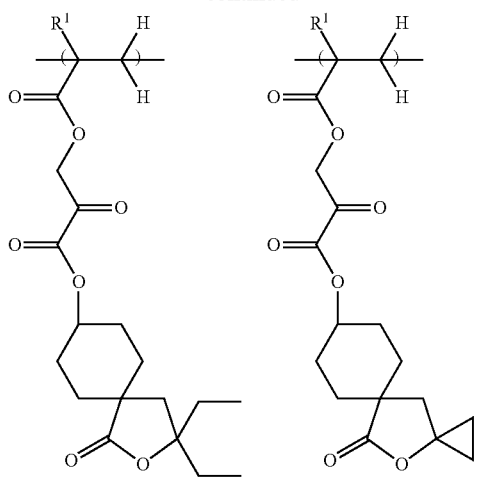
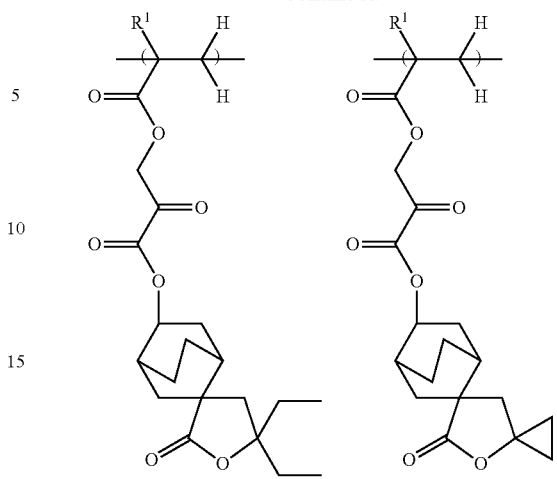

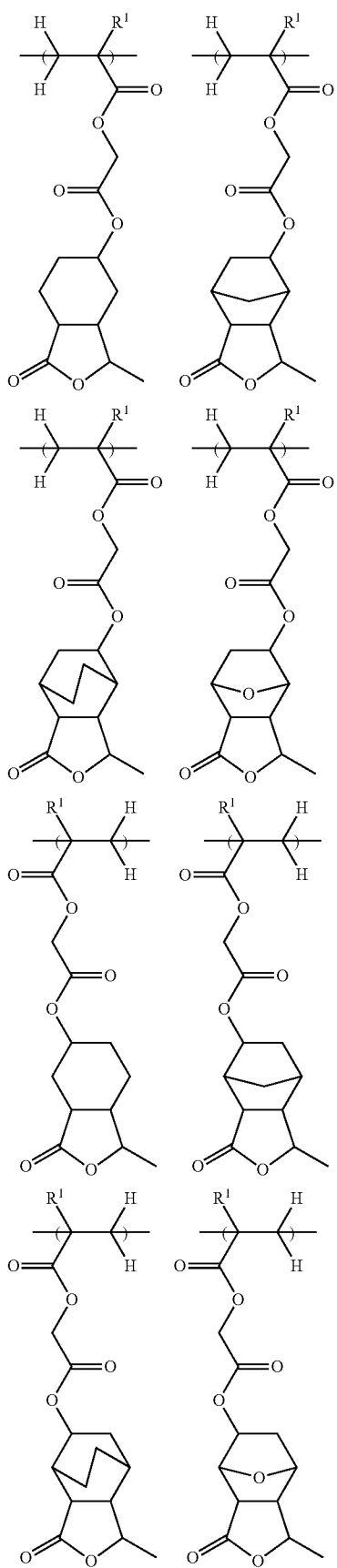
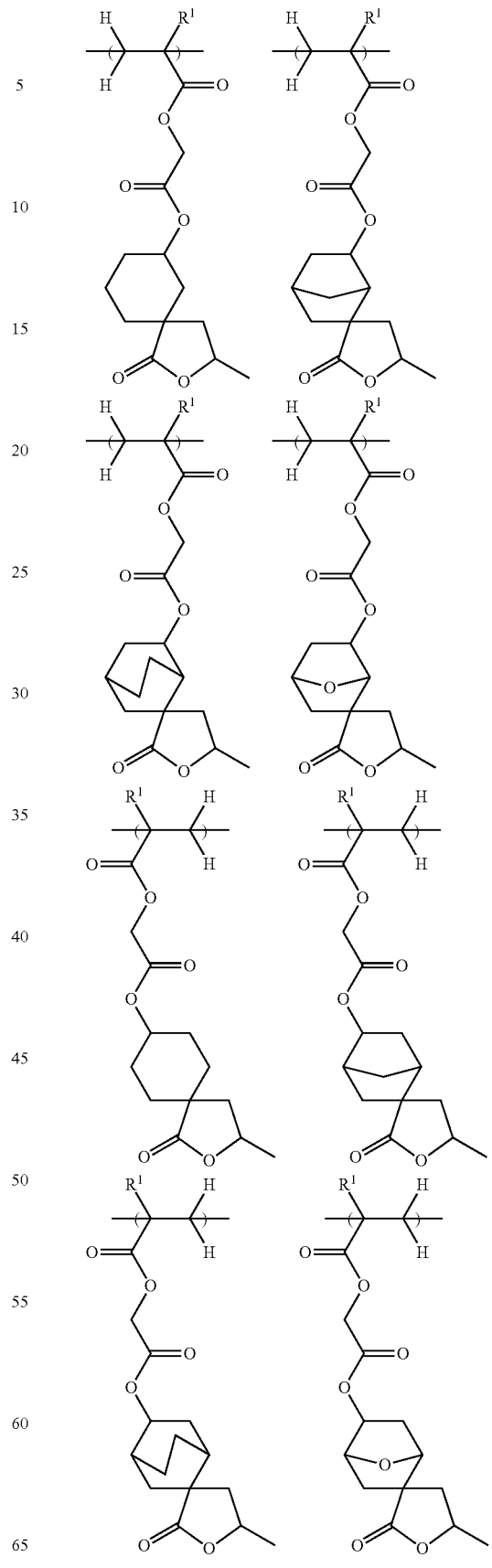

Monomer

The monomer from which the recurring unit having formula (1) is derived has the formula (8).

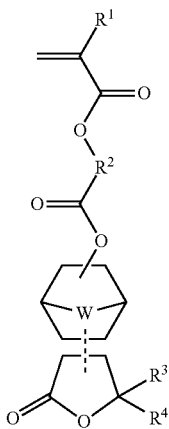
(8)

Herein R¹ to R⁴ and W are as defined above.

Of the monomers having formula (8), monomers having the formula (9) or (10) are preferred.

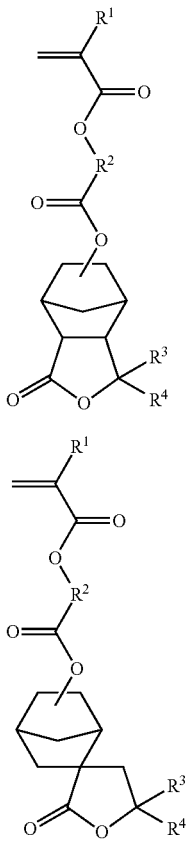
(9)

(10)

Herein R¹ to R⁴ are as defined above.

The monomer having formula (8) may be synthesized by reactions as shown in Scheme A below, for example, although the synthesis route is not limited thereto.

SCHEME A

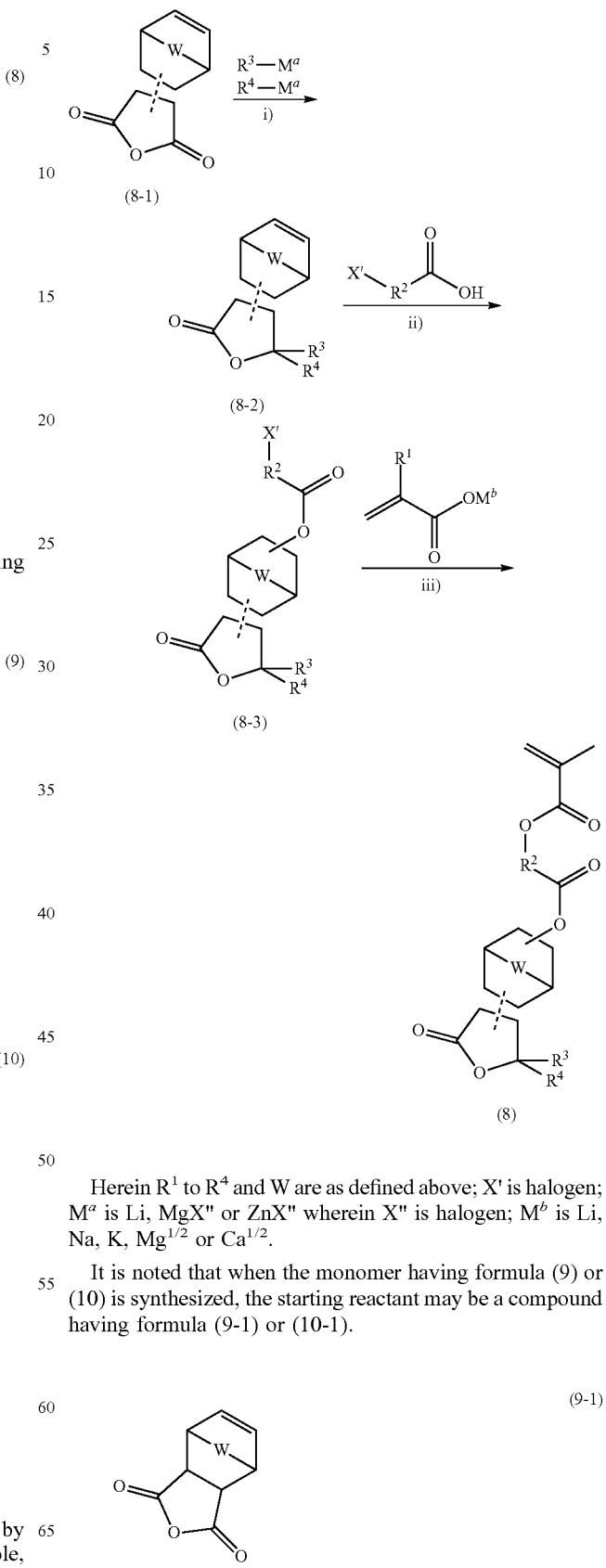

Herein R¹ to R⁴ and W are as defined above; X' is halogen; $M^a$ is Li, MgX" or ZnX" wherein X" is halogen; $M^b$ is Li, Na, K, $Mg^{1/2}$ or $Ca^{1/2}$.

It is noted that when the monomer having formula (9) or (10) is synthesized, the starting reactant may be a compound having formula (9-1) or (10-1).

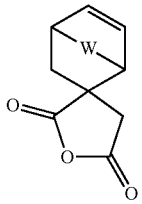

(10-1)

In Scheme A, reaction i) is reaction of an acid anhydride (8-1) with organometallic reagents to form a corresponding lactone compound (8-2).

The reaction readily takes place by a well-known procedure. Suitable organometallic reagents include Grignard reagents, organic lithium reagents and organic zinc reagents. The organometallic reagents are sequentially reacted with the reactant, carboxylic anhydride in an amount of 1 mole of each reagent per mole of the carboxylic anhydride, to form a corresponding lactone unit. Where $R^3$ and $R^4$ in the organometallic reagents are identical, 2 moles of the organometallic reagent is reacted with 1 mole of the reactant, carboxylic anhydride to form a corresponding lactone unit. $R^3$ and $R^4$ may bond together, and in this case, the group formed by $R^3$ and $R^4$ is a $C_2$-$C_{15}$ straight, branched or cyclic alkylene group.

Reaction ii) in Scheme A is addition reaction of carboxylic acid to the olefin to form a corresponding haloalkyl ester (8-3).

The reaction may be performed by a standard procedure. The olefin unit is reacted with carboxylic acid in the presence of a strong acid. Suitable strong acids include mineral acids such as hydrochloric acid, sulfuric acid, nitric acid and perchloric acid, and organic acids such as methanesulfonic acid, trifluoroacetic acid, trifluoromethanesulfonic acid, p-toluenesulfonic acid, and benzenesulfonic acid. The reaction may be performed in a solventless system, although a solvent may be used in an auxiliary manner, for example, methylene chloride, toluene, hexane, diethyl ether, tetrahydrofuran or acetonitrile.

Reaction iii) in Scheme A is reaction of haloalkyl ester (8-3) with carboxylic acid or carboxylic acid salt to form a corresponding lactone compound (8).

The reaction readily takes place by a well-known procedure. As the carboxylic acid salt, commercially available carboxylic acid salts, typically carboxylic acid metal salts may be used as such. Alternatively, the carboxylic acid salt may be prepared in situ from a corresponding carboxylic acid (e.g., methacrylic acid or acrylic acid) and a base. An appropriate amount of the carboxylic acid salt is 0.5 to 10 moles, more preferably 1.0 to 3.0 moles per mole of the haloalkyl ester. If the salt is less than 0.5 mole, a large fraction of the reactant may be left unreacted, with a substantial drop of yield. More than 10 moles of the salt may be uneconomical because of the increased amount of the salt and a lowering of pot yield.

Examples of the base used herein include amines such as ammonia, triethylamine, pyridine, lutidine, collidine, and N,N-dimethylaniline; hydroxides such as sodium hydroxide, potassium hydroxide, and tetramethylammonium hydroxide; carbonates such as potassium carbonate and sodium hydrogencarbonate, metals such as sodium, metal hydrides such as sodium hydride; metal alkoxides such as sodium methoxide and potassium t-butoxide, organometallic compounds such as butyl lithium and ethylmagnesium bromide; and metal amides such as lithium diisopropylamide, which may be used alone or in admixture. An appropriate amount of the base used is 0.2 to 10 moles, more preferably 0.5 to 2.0 moles per mole of the corresponding carboxylic acid. If the base is less than 0.2 mole, a large fraction of the carboxylic acid may become waste, which is uneconomical. More than 10 moles of the base may promote side reactions, with a substantial drop of yield.

A solvent may be used for reaction iii). Suitable solvents include hydrocarbons such as toluene, xylene, hexane and heptane, chlorinated solvents such as methylene chloride, chloroform, and dichloroethane; ethers such as diethyl ether, tetrahydrofuran and dibutyl ether, ketones such as acetone and 2-butanone; esters such as ethyl acetate and butyl acetate; nitriles such as acetonitrile; alcohols such as methanol and ethanol; aprotic polar solvents such as N,N-dimethylformamide, N,N-dimethylacetamide and dimethyl sulfoxide; and water, which may be used alone or in admixture. To the reaction system, a phase transfer catalyst such as tetrabutylammonium hydrogensulfate may be added. An appropriate amount of the phase transfer catalyst added is 0.0001 to 1.0 mole, more preferably 0.001 to 0.5 mole per mole of the haloalkyl ester. Less than 0.0001 mole of the phase transfer catalyst may fail to exert catalytic effect whereas more than 1.0 mole may be uneconomical because of the increased catalyst cost.

The intermediate, haloalkyl ester (8-3) may also be synthesized by the method shown as Scheme B below.

SCHEME B

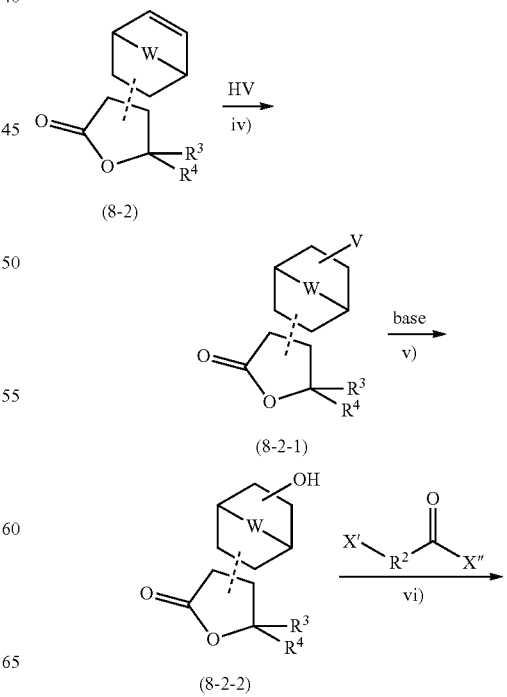

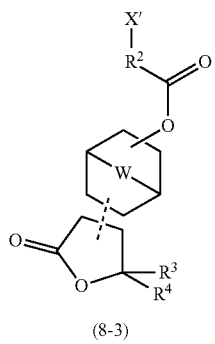

(8-3)

Herein $R^2$ to $R^4$, W and X' are as defined above, X" is halogen, and HV designates an acid.

In Scheme B, reaction iv) is addition reaction of an acid to an olefin to form a corresponding lactone derivative (8-2-1).

The reaction may be performed by a standard procedure. Examples of the acid HV include mineral acids such as hydrogen chloride, hydrogen bromide, hydrogen iodide, hydrochloric acid, hydrobromic acid, hydroiodic acid, nitric acid, perchloric acid and sulfuric acid, and organic acids such as formic acid, acetic acid, propionic acid, benzoic acid, chloroformic acid, chloroacetic acid, dichloroacetic acid, trichloroacetic acid, fluoroacetic acid, trifluoroacetic acid, 3,3,3-trifluoropropionic acid, p-toluenesulfonic acid, methanesulfonic acid and trifluoromethanesulfonic acid, which may be used alone or in admixture. The reaction may be performed in a solventless system, although a solvent may be used in an auxiliary manner.

Reaction v) in Scheme B is reaction of lactone derivative (8-2-1) with a base to form a corresponding hydroxy-lactone compound (8-2-2).

The reaction may be performed by a standard procedure, i.e., by reacting the reactant with a base in a solvent. Suitable bases include alkoxides such as sodium methoxide, sodium ethoxide, lithium methoxide, lithium ethoxide, lithium tert-butoxide, and potassium tert-butoxide, inorganic hydroxides such as sodium hydroxide, lithium hydroxide, potassium hydroxide, barium hydroxide and tetra-n-butylammonium hydroxide, and inorganic carbonates such as sodium carbonate, sodium hydrogencarbonate, lithium carbonate, and potassium carbonate. Suitable solvents include alcohols such as methanol, ethanol, and isopropanol, hydrocarbons such as toluene, xylene, hexane and heptane, and ethers such as diethyl ether and tetrahydrofuran, which may be used alone or in admixture.

Reaction vi) in Scheme B is reaction of hydroxy-lactone compound (8-2-2) with an acid halide to form a corresponding haloalkyl ester (8-3).

The reaction may be performed by a standard procedure. Specifically, the reaction may be performed in a solventless system or in a solvent (e.g., methylene chloride, toluene, hexane, diethyl ether, tetrahydrofuran or acetonitrile) by adding hydroxy-lactone compound (8-2-2), a corresponding acid halide (e.g., 2-chloroacetic acid chloride), and a base (e.g., triethylamine, pyridine or 4-dimethylaminopyridine) in sequence or at the same time, and optional cooling or heating.

The intermediate, haloalkyl ester (8-3) may also be synthesized by the method shown as Scheme C below.

SCHEME C

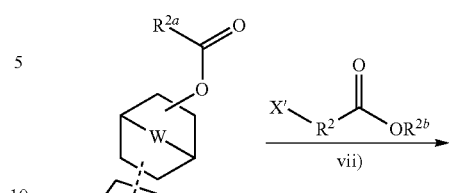

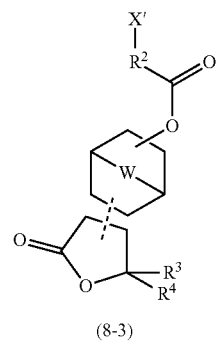

(8-3)

Herein $R^2$ to $R^4$, W and X' are as defined above, $R^{2a}$ is hydrogen or a $C_1$-$C_{10}$ straight, branched or cyclic hydrocarbon group, and $R^{2b}$ is a $C_1$-$C_{10}$ straight, branched or cyclic hydrocarbon group.

Reaction vii) in Scheme C is transesterification to form a corresponding haloalkyl ester (8-3).

The reaction may be performed by a standard procedure. The reaction may be performed in a solventless system, although a solvent may be used in an auxiliary manner. Suitable solvents used herein include ethers such as tetrahydrofuran, diethyl ether, di-n-butyl ether, and 1,4-dioxane, and hydrocarbons such as n-hexane, n-heptane, benzene, toluene, xylene, and cumene, which may be used alone or in admixture.

If desired, a catalyst may be used. Suitable catalysts include metal alkoxides such as sodium methoxide, sodium ethoxide, potassium t-butoxide, magnesium ethoxide, titanium(IV) methoxide, titanium(IV) ethoxide, and titanium (IV) isopropoxide; tin compounds such as dibutyltin oxide and dibutyltin dimethoxide; organic amines such as triethylamine, N,N-dimethylaminopyridine, and 1,8-diazabicyclo [5.4.0]-7-undecene; inorganic bases such as sodium hydroxide, potassium carbonate and sodium carbonate, which may be used alone or in admixture. An appropriate amount of the catalyst used is 0.001 to 5.0 moles, more preferably 0.001 to 0.1 mole per mole of the reactant. The reaction temperature, which varies with other reaction conditions, is preferably in a range of 50 to 200° C. Preferably the reaction is performed while distilling off the ester by-product resulting from the reaction.

In addition to the recurring units having formula (1), the polymer may further comprise recurring units having formula (4).

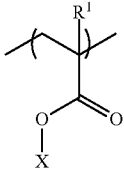
(4)

Herein R¹ is as defined above, and X is an acid labile group.

A polymer comprising recurring units of formula (4) is decomposed under the action of acid to generate carboxylic acid so that it may turn alkali soluble. The acid labile group X may be selected from a variety of such groups. Examples of the acid labile group are groups of the following general formulae (L1) to (L9), tertiary alkyl groups of 4 to 20 carbon atoms, preferably 4 to 15 carbon atoms, trialkylsilyl groups in which each alkyl moiety has 1 to 6 carbon atoms, and oxoalkyl groups of 4 to 20 carbon atoms.

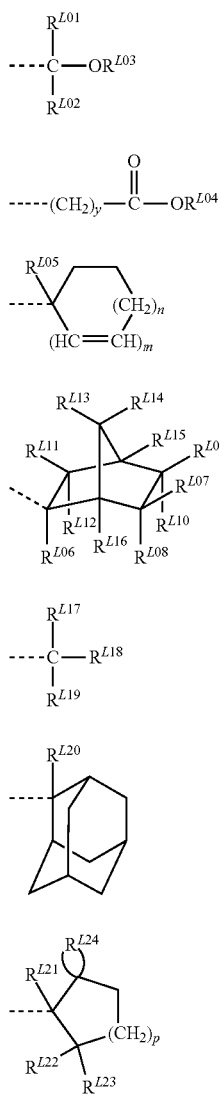

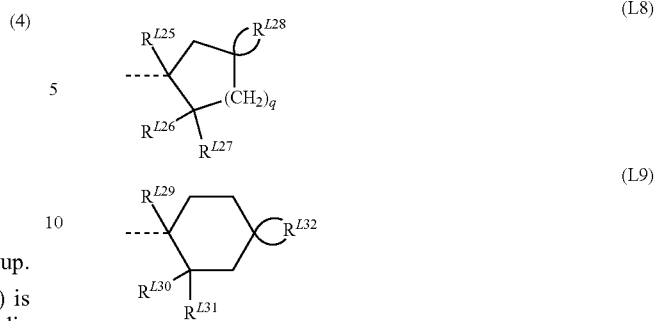

In formula (L1), $R^{L01}$ and $R^{L02}$ are each independently hydrogen or a straight, branched or cyclic alkyl group of 1 to 18 carbon atoms, preferably 1 to 10 carbon atoms, examples of which include methyl, ethyl, propyl, isopropyl, n-butyl, sec-butyl, tert-butyl, cyclopentyl, cyclohexyl, 2-ethylhexyl, n-octyl, norbornyl, tricyclodecanyl, tetracyclododecanyl, and adamantyl. $R^{L03}$ is a monovalent hydrocarbon group of 1 to 18 carbon atoms, preferably 1 to 10 carbon atoms, which may contain a heteroatom such as oxygen, examples of which include straight, branched or cyclic alkyl groups and substituted forms of these groups in which some hydrogen atoms are replaced by hydroxyl, alkoxy, oxo, amino, alkylamino or the like. Suitable straight, branched or cyclic alkyl groups are as exemplified for $R^{L01}$ and $R^{L02}$. Exemplary substituted alkyl groups are illustrated below.

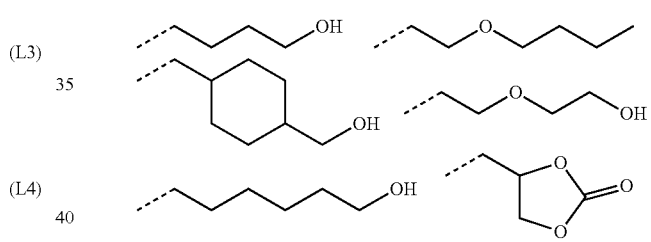

A pair of $R^{L01}$ and $R^{L02}$, $R^{L01}$ and $R^{L03}$, or $R^{L02}$ and $R^{L03}$ may bond together to form a ring with the carbon and oxygen atoms to which they are attached. A ring-forming combination of $R^{L01}$, $R^{L02}$, and $R^{L03}$ is a straight or branched alkylene group of 1 to 18 carbon atoms, preferably 1 to 10 carbon atoms.

In formula (L2), $R^{L04}$ is a $C_4$-$C_{20}$, preferably $C_4$-$C_{15}$ tertiary alkyl group, a trialkylsilyl group in which each alkyl moiety has 1 to 6 carbon atoms, a $C_4$-$C_{20}$ oxoalkyl group, or a group of formula (L1). Suitable tertiary alkyl groups include tert-butyl, tert-pentyl, 1,1-diethylpropyl, 2-cyclopentylpropan-2-yl, 2-cyclohexylpropan-2-yl, 2-(bicyclo[2.2.1]heptan-2-yl)propan-2-yl, 2-(adamantan-1-yl)propan-2-yl, 1-ethylcyclopentyl, 1-butylcyclopentyl, 1-ethylcyclohexyl, 1-butylcyclohexyl, 1-ethyl-2-cyclopentenyl, 1-ethyl-2-cyclohexenyl, 2-methyl-2-adamantyl, and 2-ethyl-2-adamantyl. Suitable trialkylsilyl groups include trimethylsilyl, triethylsilyl, and dimethyl-tert-butylsilyl. Suitable oxyalkyl groups include 3-oxocyclohexyl, 4-methyl-2-oxooxan-4-yl, and 5-methyl-2-oxooxolan-5-yl. In formula (L2), y is an integer of 0 to 6.

In formula (L3), $R^{L05}$ is an optionally substituted, straight, branched or cyclic $C_1$-$C_8$ alkyl group or optionally substituted $C_6$-$C_{20}$ aryl group. Examples of the optionally substituted alkyl groups include straight, branched or cyclic ones such as methyl, ethyl, propyl, isopropyl, n-butyl, sec-butyl, tert-butyl, tert-pentyl, n-pentyl, n-hexyl, cyclopentyl, and cyclohexyl; and substituted forms of the foregoing in which some hydrogen atoms are replaced by hydroxyl, alkoxy, carboxyl, alkoxycarbonyl, oxo, amino, alkylamino, cyano, mercapto, alkylthio, sulfo or other groups. Exemplary optionally substituted aryl groups are phenyl, methylphenyl, naphthyl, anthryl, phenanthryl, and pyrenyl. In formula (L3), m is 0 or 1, n is an integer of 0 to 3, and 2m+n is equal to 2 or 3.

In formula (L4), $R^{L06}$ is an optionally substituted, straight, branched or cyclic $C_1$-$C_8$ alkyl group or optionally substituted $C_6$-$C_{20}$ aryl group. Examples are as exemplified for $R^{L05}$. $R^{L07}$ to $R^{L16}$ each independently denote hydrogen or a $C_1$-$C_{15}$ monovalent hydrocarbon group. Exemplary hydrocarbon groups are straight, branched or cyclic alkyl groups such as methyl, ethyl, propyl, isopropyl, n-butyl, sec-butyl, tert-butyl, tert-pentyl, n-pentyl, n-hexyl, n-octyl, n-nonyl, n-decyl, cyclopentyl, cyclohexyl, cyclopentylmethyl, cyclopentylethyl, cyclopentylbutyl, cyclohexylmethyl, cyclohexylethyl and cyclohexylbutyl, and substituted forms of the foregoing in which some hydrogen atoms are replaced by hydroxyl, alkoxy, carboxyl, alkoxycarbonyl, oxo, amino, alkylamino, cyano, mercapto, alkylthio, sulfo or other groups. Alternatively, a pair of $R^{L07}$ to $R^{L16}$ (e.g., $R^{L07}$ and $R^{L08}$, $R^{L07}$ and $R^{L09}$, $R^{L08}$ and $R^{L10}$, $R^{L09}$ and $R^{L10}$, $R^{L11}$ and $R^{L12}$, or $R^{L13}$ and $R^{L14}$) may bond together to form a ring. A ring-forming combination of $R^{L07}$ to $R^{L16}$ is a $C_1$-$C_{15}$ divalent hydrocarbon group, examples of which are those exemplified above for the monovalent hydrocarbon groups, with one hydrogen atom being eliminated. Also a pair of $R^{L07}$ to $R^{L16}$ (e.g., $R^{L07}$ and $R^{L09}$, $R^{L09}$ and $R^{L15}$, or $R^{L13}$ and $R^{L15}$) which are attached to vicinal carbon atoms may bond together directly to form a double bond.

In formula (L5), $R^{L17}$ to $R^{L19}$ are each independently a $C_1$-$C_{15}$ straight, branched or cyclic alkyl group. Suitable alkyl groups include methyl, ethyl, propyl, isopropyl, n-butyl, sec-butyl, tert-butyl, cyclopentyl, cyclohexyl, 2-ethylhexyl, n-octyl, 1-adamantyl and 2-adamantyl.

In formula (L6), $R^{L20}$ is an optionally substituted, straight, branched or cyclic $C_1$-$C_{10}$ alkyl group or optionally substituted $C_6$-$C_{20}$ aryl group. Examples are as exemplified for $R^{L05}$.

In formula (L7), $R^{L21}$ is an optionally substituted, straight, branched or cyclic $C_1$-$C_{10}$ alkyl group or optionally substituted $C_6$-$C_{20}$ aryl group. Examples are as exemplified for $R^{L05}$. $R^{L22}$ and $R^{L23}$ are each independently hydrogen or a $C_1$-$C_{15}$ straight, branched or cyclic monovalent hydrocarbon group. $R^{L22}$ and $R^{L23}$ may bond together to form a ring with the carbon atom to which they are attached, and the ring is a substituted or unsubstituted cyclopentane or cyclohexane ring. $R^{L24}$ is a divalent group which forms a substituted or unsubstituted cyclopentane, cyclohexane or norbornane ring with the carbon atom to which it is attached. In formula (L7), p is 1 or 2.

In formula (L8), $R^{L25}$ is an optionally substituted, straight, branched or cyclic $C_1$-$C_{10}$ alkyl group or optionally substituted $C_6$-$C_{20}$ aryl group. Examples are as exemplified for $R^{L05}$. $R^{L28}$ is a divalent group which forms a substituted or unsubstituted cyclopentane, cyclohexane or norbornane ring with the carbon atom to which it is attached. $R^{L26}$ and $R^{L27}$ are each independently hydrogen or a $C_1$-$C_{10}$ straight, branched or cyclic monovalent hydrocarbon group. $R^{L26}$ and $R^{L27}$ may bond together to form a ring with the carbon atom to which they are attached, and the ring is a substituted or unsubstituted cyclopentane or cyclohexane ring. In formula (L8), q is 1 or 2.

In formula (L9), $R^{L29}$ is an optionally substituted, straight, branched or cyclic $C_1$-$C_{10}$ alkyl group or optionally substituted $C_6$-$C_{20}$ aryl group. Examples are as exemplified for $R^{L05}$. $R^{L30}$ and $R^{L31}$ are each independently hydrogen or a $C_1$-$C_{10}$ straight, branched or cyclic monovalent hydrocarbon group. $R^{L30}$ and $R^{L31}$ may bond together to form a ring with the carbon atom to which they are attached, and the ring is a substituted or unsubstituted cyclopentane or cyclohexane ring. $R^{L32}$ is a divalent group which forms a substituted or unsubstituted cyclopentane, cyclohexane or norbornane ring with the carbon atom to which it is attached.

Of the acid labile groups of formula (L1), the straight or branched groups are exemplified below, but not limited thereto.

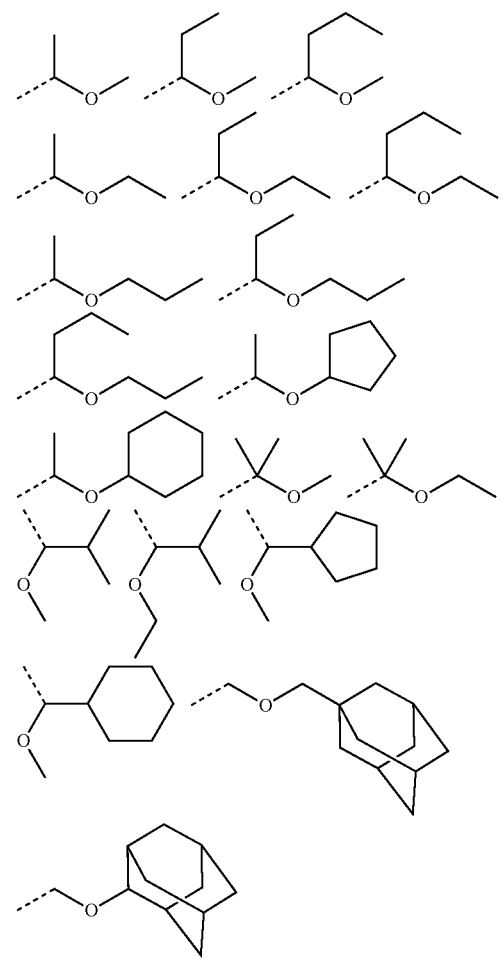

Of the acid labile groups of formula (L1), the cyclic groups are, for example, tetrahydrofuran-2-yl, 2-methyltetrahydrofuran-2-yl, tetrahydropyran-2-yl, and 2-methyltetrahydropyran-2-yl.

Examples of the acid labile group of formula (L2) include tert-butoxycarbonyl, tert-butoxycarbonylmethyl, tert-pentyloxycarbonyl, tert-pentyloxycarbonylmethyl, 1,1-diethylpropyloxycarbonyl, 1, 1-diethylpropyloxycarbonylmthylmethyl, 1-ethylcyclopentyloxycarbonyl, 1-ethylcyclopentyloxycarbonylmethyl, 1-ethyl-2-cyclopentenyloxycarbonyl, 1-ethyl-2-cyclopentenyloxycarbonylmethyl, 1-ethoxyethoxycarbonylmethyl, 2-tetrahydropyranyloxycarbonyl, and 2-tetrahydrofuranyloxycarbonylmethyl.

Examples of the acid labile group of formula (L3) include 1-methylcyclopentyl, 1-ethylcyclopentyl, 1-n-propylcyclopentyl, 1-isopropylcyclopentyl, 1-n-butylcyclopentyl, 1-sec-butylcyclopentyl, 1-tert-butylcyclopentyl, 1-cyclohexylcyclopentyl, 1-(4-methoxy-n-butyl)cyclopentyl, 1-methylcyclohexyl, 1-ethylcyclohexyl, 3-methyl-1-cyclopenten-3-yl, 3-ethyl-1-cyclopenten-3-yl, 3-methyl-1-cyclohexen-3-yl, and 3-ethyl-1-cyclohexen-3-yl.

Of the acid labile groups of formula (L4), those groups of the following formulae (L4-1) to (L4-4) are preferred.

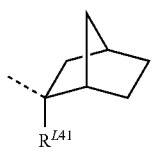
(L4-1)

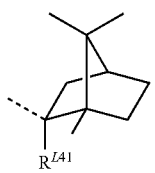
(L4-2)

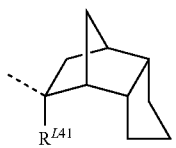
(L4-3)

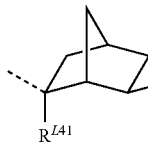
(L4-4)

In formulas (L4-1) to (L4-4), the broken line denotes a bonding site and direction. $R^{L41}$ is each independently a monovalent hydrocarbon group, typically a $C_1$-$C_{10}$ straight, branched or cyclic alkyl group, such as methyl, ethyl, propyl, isopropyl, n-butyl, sec-butyl, tert-butyl, tert-pentyl, n-pentyl, n-hexyl, cyclopentyl and cyclohexyl.

For formulas (L4-1) to (L4-4), there can exist enantiomers and diastereomers. Each of formulae (L4-1) to (L4-4) collectively represents all such stereoisomers. Such stereoisomers may be used alone or in admixture.

For example, the formula (L4-3) represents one or a mixture of two selected from groups having the following formulas (L4-3-1) and (L4-3-2).

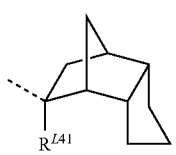
(L4-3-1)

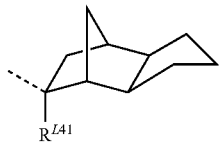
(L4-3-2)

Note that $R^{L41}$ is as defined above.

Similarly, the formula (L4-4) represents one or a mixture of two or more selected from groups having the following formulas (L4-4-1) to (L4-4-4).

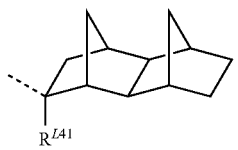
(L4-4-1)

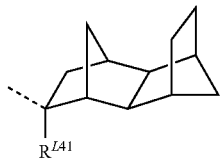
(L4-4-2)

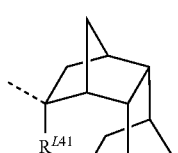
(L4-4-3)

(L4-4-4)

Note that $R^{L41}$ is as defined above.

Each of formulas (L4-1) to (L4-4), (L4-3-1) and (L4-3-2), and (4-4-1) to (L4-4-4) collectively represents an enantiomer thereof and a mixture of enantiomers.

It is noted that in the above formulas (L4-1) to (L4-4), (L4-3-1) and (L4-3-2), and (L4-4-1) to (L4-4-4), the bond direction is on the exo side relative to the bicyclo[2.2.1] heptane ring, which ensures high reactivity for acid catalyzed elimination reaction (see JP-A 2000-336121). In preparing these monomers having a tertiary exo-alkyl group of bicyclo[2.2.1]heptane structure as a substituent group, there may be contained monomers substituted with an endo-alkyl group as represented by the following formulas (L4-1-endo) to (L4-4-endo). For good reactivity, an exo proportion of at least 50 mol % is preferred, with an exo proportion of at least 80 mol % being more preferred.

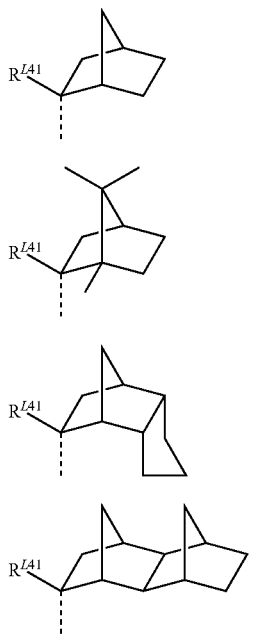

Note that $R^{L41}$ is as defined above.

Illustrative examples of the acid labile group of formula (L4) are given below.

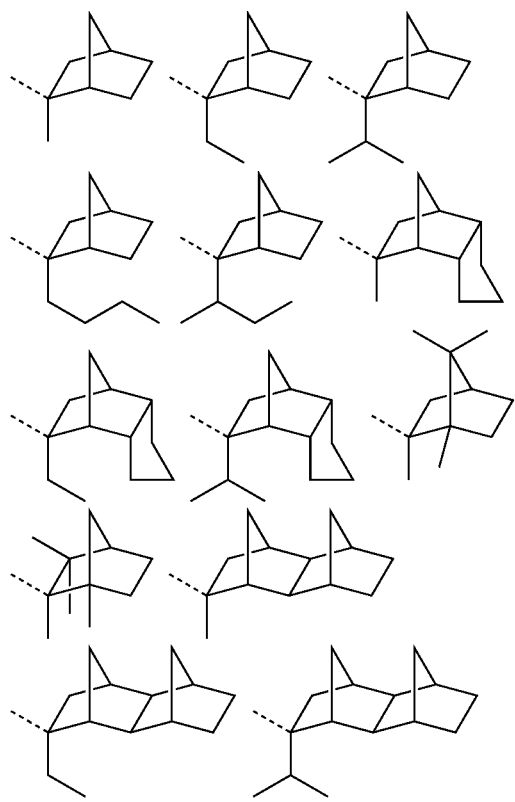

Illustrative examples of the acid labile group of formula (L5) include tert-butyl, tert-pentyl and the groups shown below, but are not limited thereto.

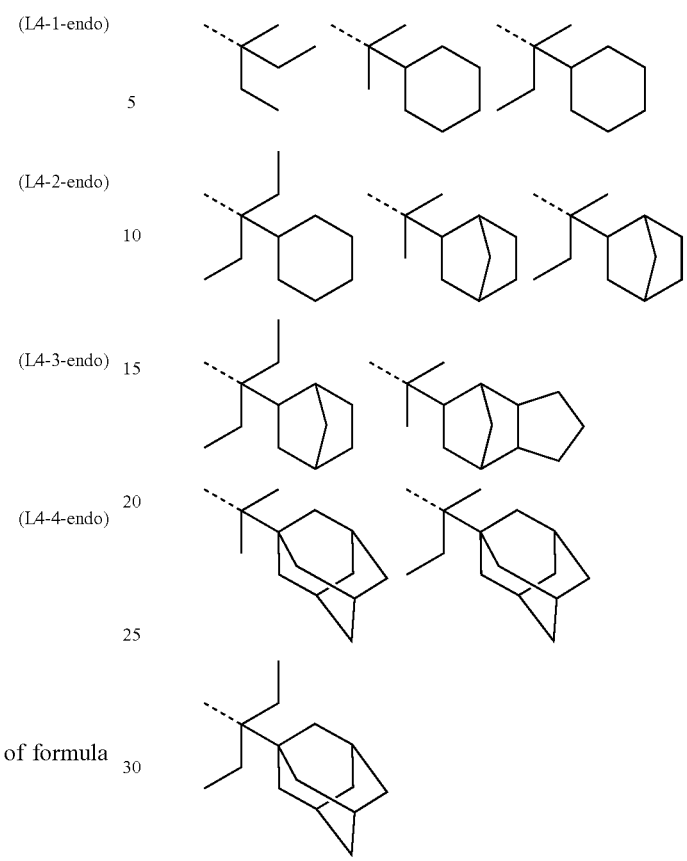

Illustrative examples of the acid labile group of formula (L6) are given below, but not limited thereto.

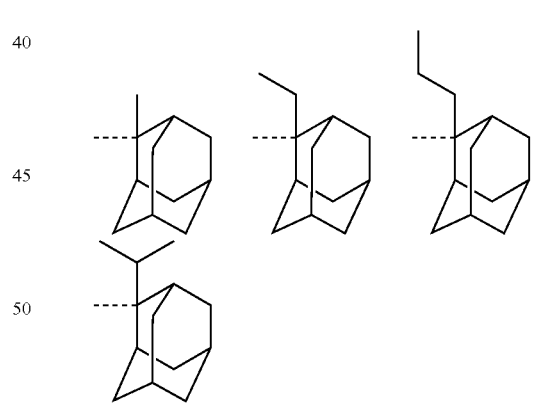

Illustrative examples of the acid labile group of formula (L7) are given below, but not limited thereto.

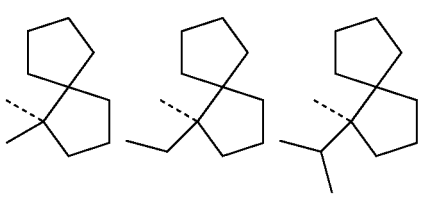

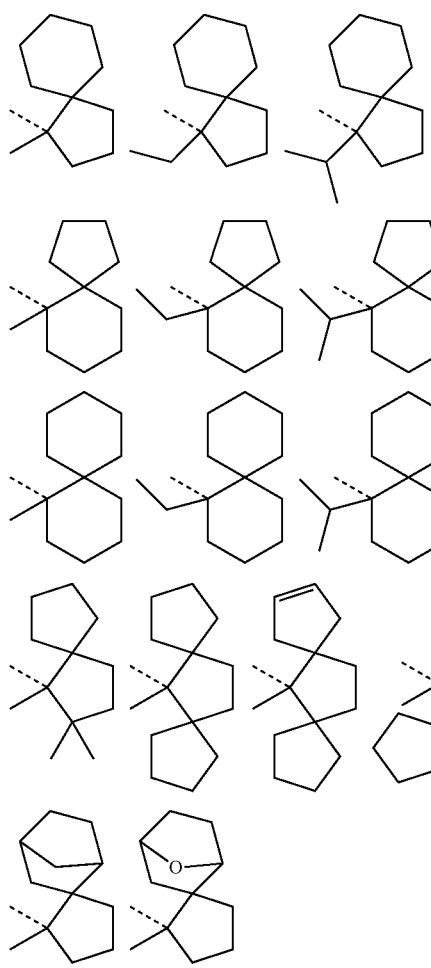

Illustrative examples of the acid labile group of formula (L8) are given below, but not limited thereto.

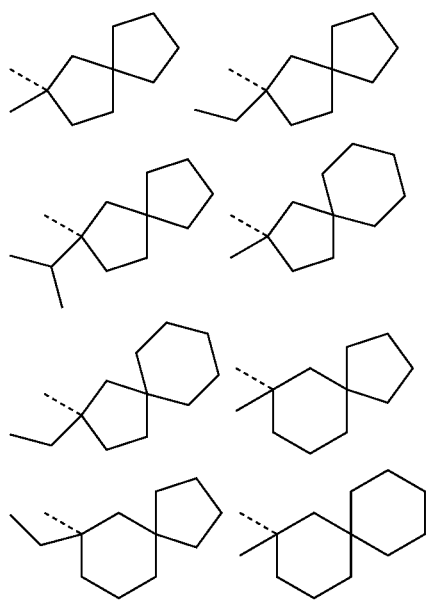

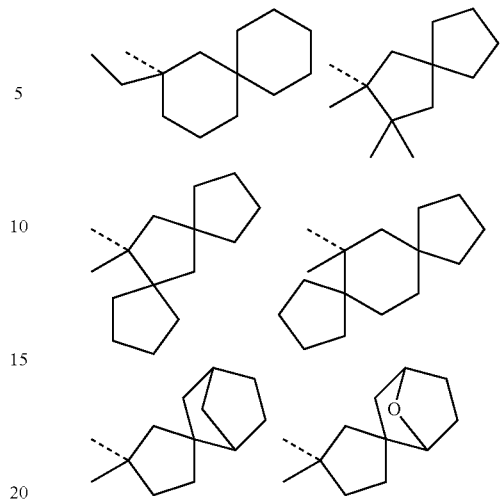

Illustrative examples of the acid labile group of formula (L9) are given below, but not limited thereto.

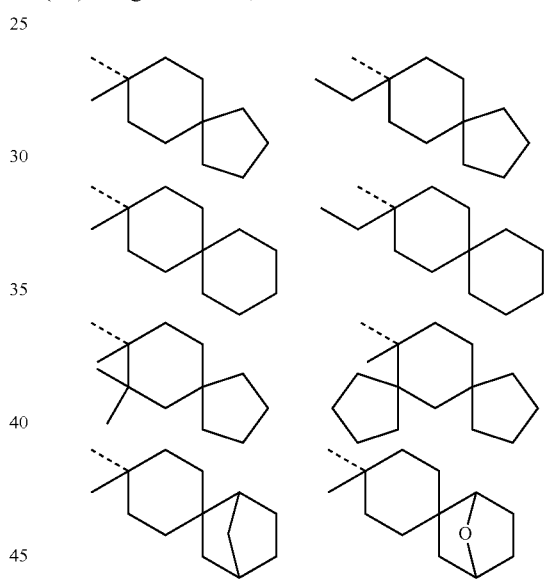

Examples of the tertiary $C_4$-$C_{20}$ alkyl groups, trialkylsilyl groups in which each alkyl moiety has 1 to 6 carbon atoms, and $C_4$-$C_{20}$ oxoalkyl groups are as exemplified for $R^{L04}$ and the like.

Illustrative examples of the recurring units having formula (4) are given below, but not limited thereto. $R^1$ is as defined above.

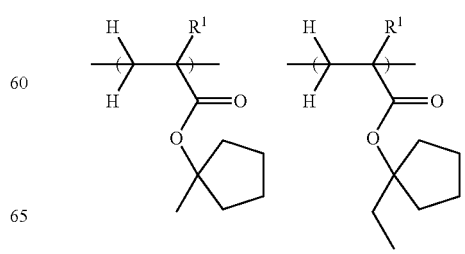

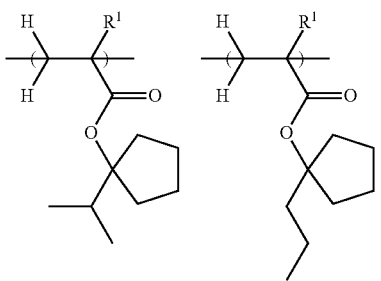
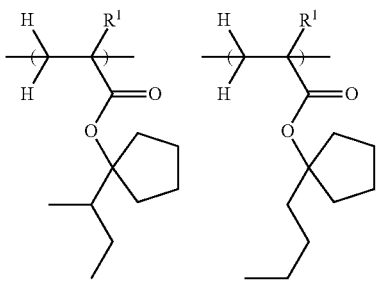
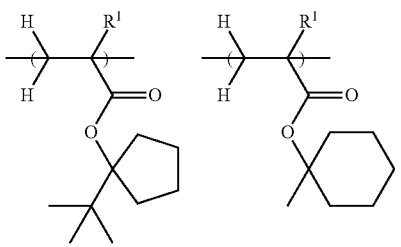
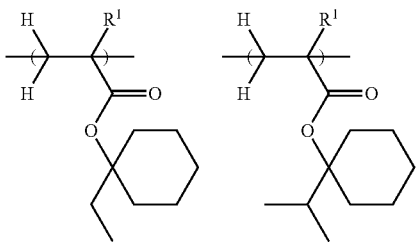
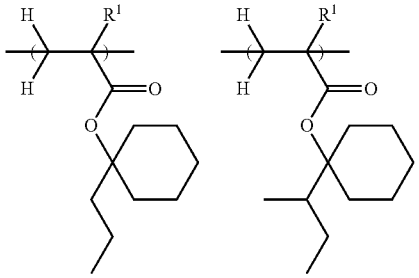
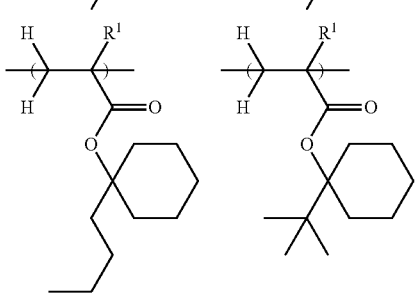
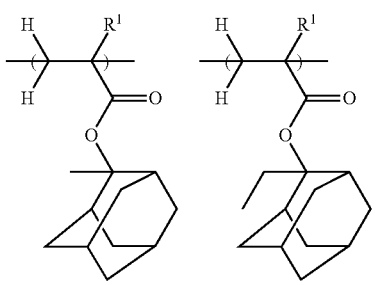
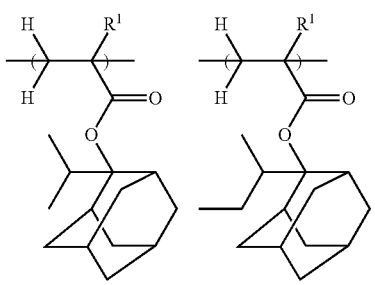
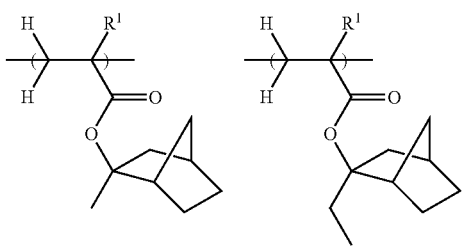
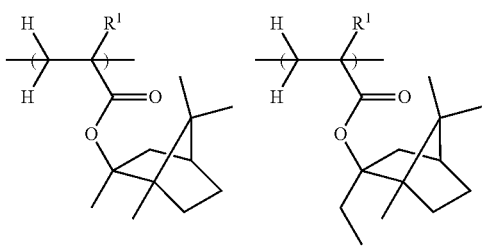
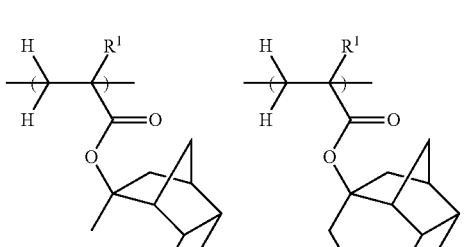
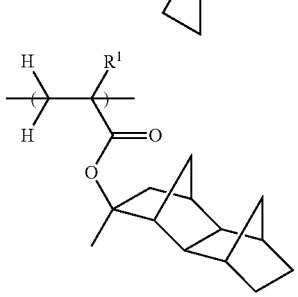

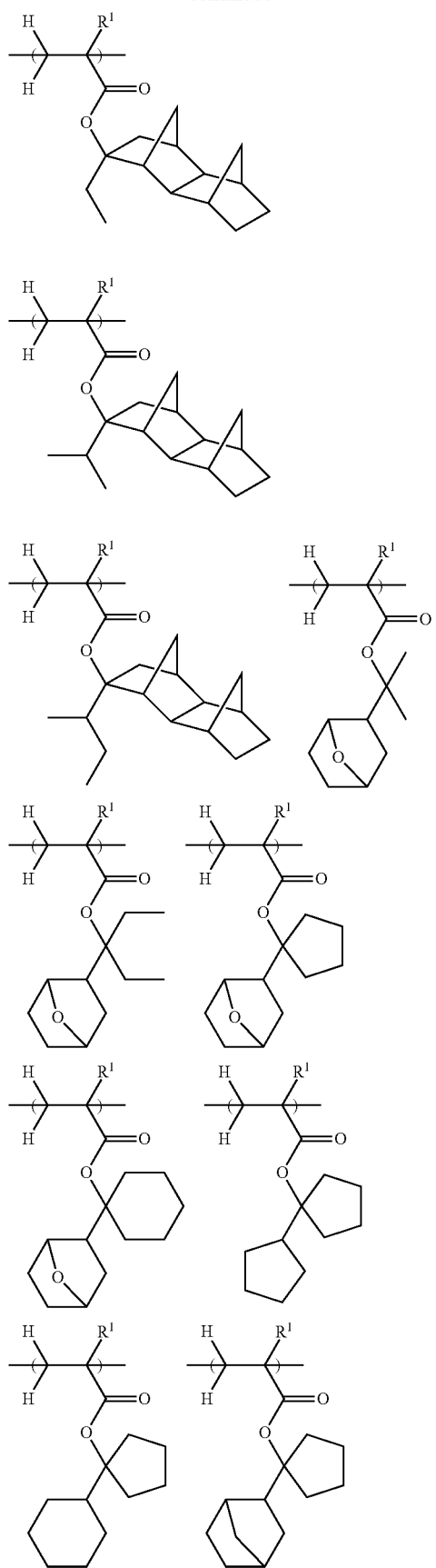
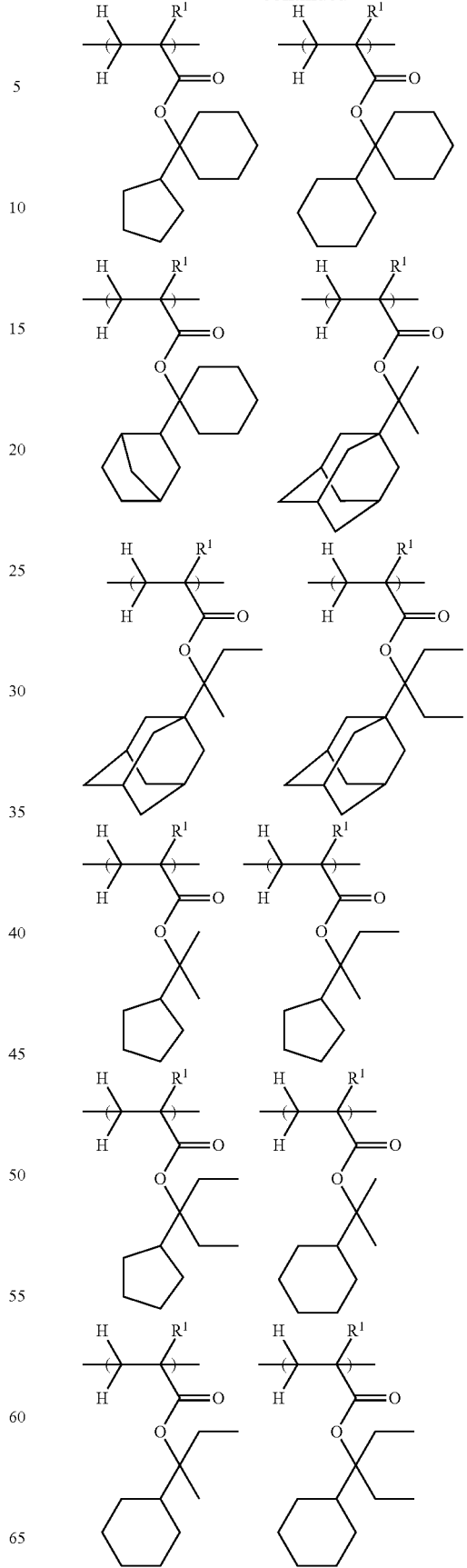

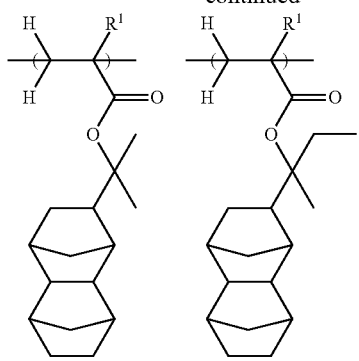
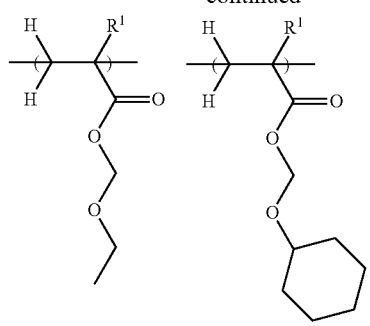
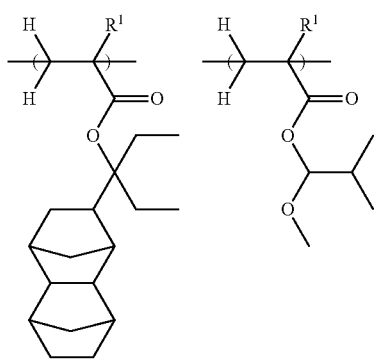
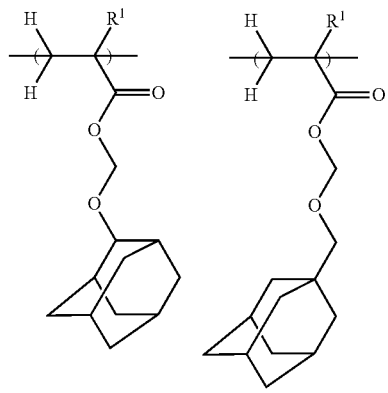
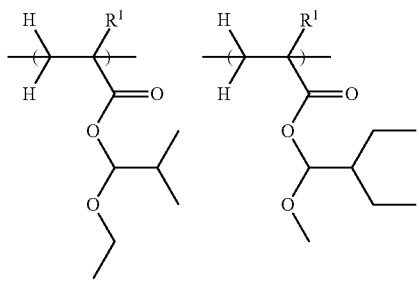
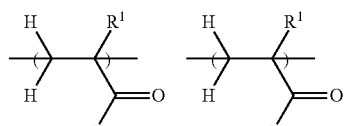
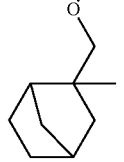
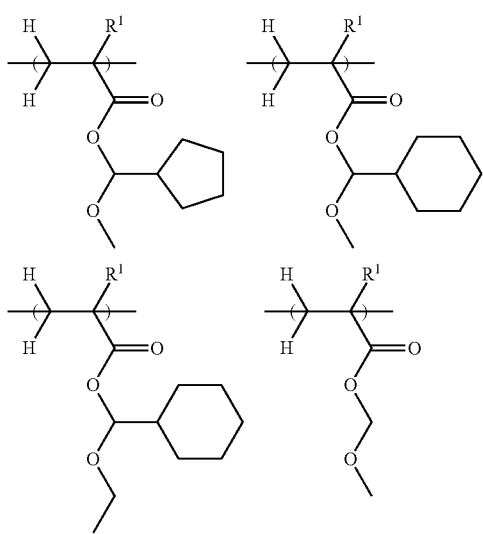
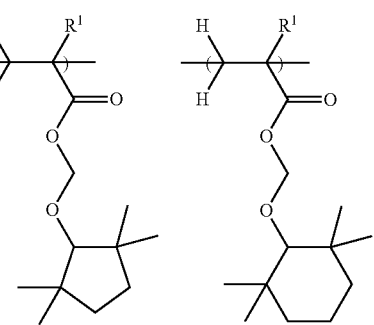

-continued

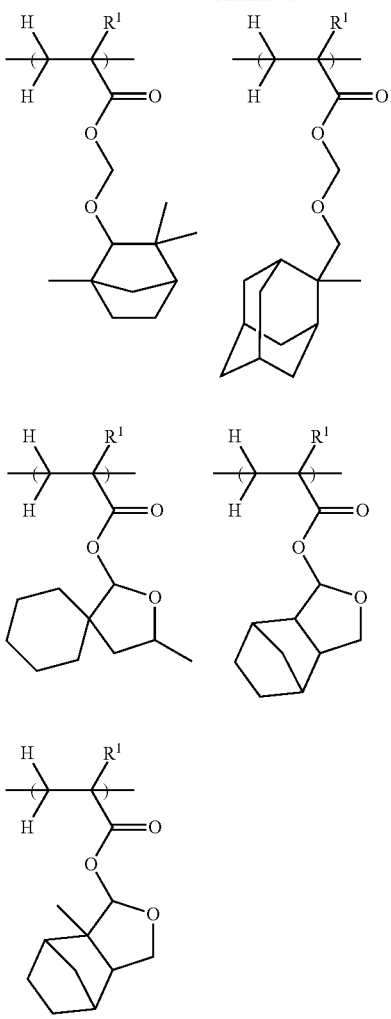

The polymer may further comprise recurring units of at least one type selected from recurring units having the formulae (5) to (7).

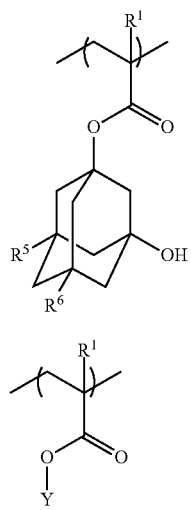

(5)

(6)

-continued

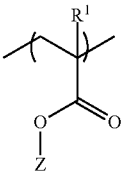

(7)

Herein $R^1$ is as defined above. $R^5$ and $R^6$ are each independently hydrogen or hydroxyl. Y is a substituent group containing a lactone structure different from formula (1) or a substituent group containing a sultone structure. Z is hydrogen, a $C_1$-$C_{15}$ fluorinated hydrocarbon group, or a $C_1$-$C_{15}$ fluoroalcohol-containing substituent group.

Illustrative examples of the recurring units having formula (5) are given below, but not limited thereto. Herein $R^1$ is as defined above.

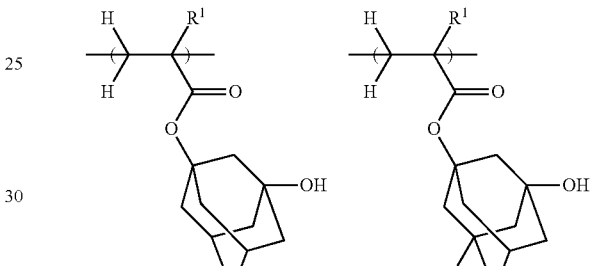

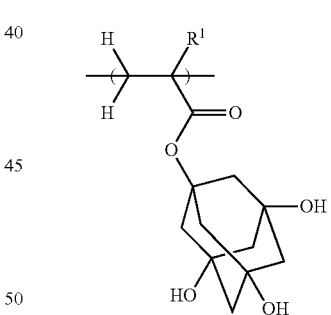

Illustrative examples of the recurring units having formula (6) are given below, but not limited thereto. Herein $R^1$ is as defined above.

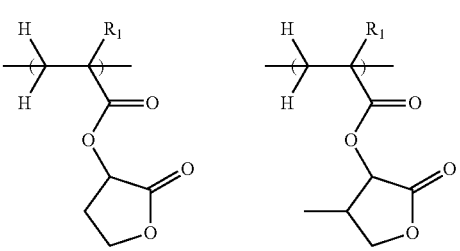

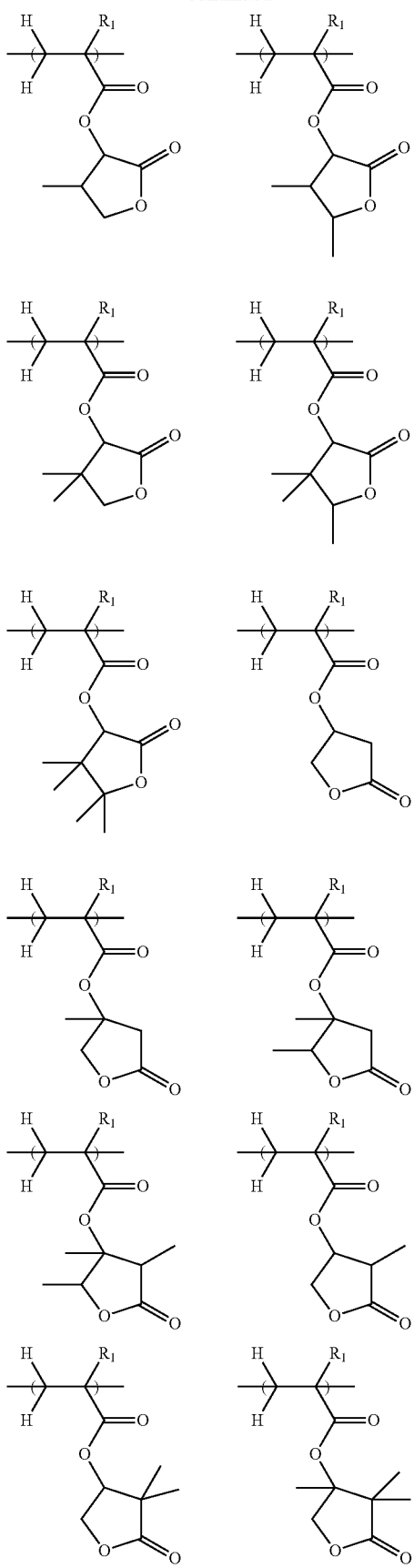
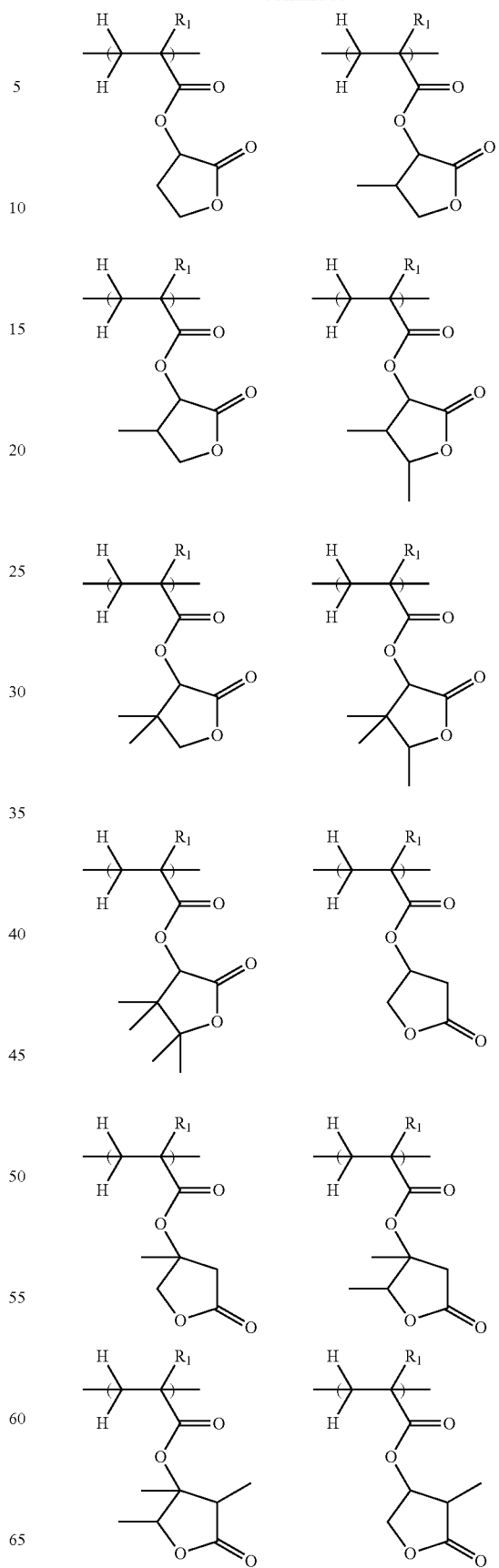

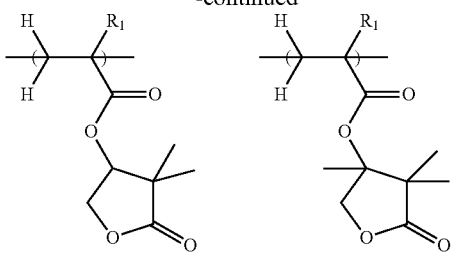
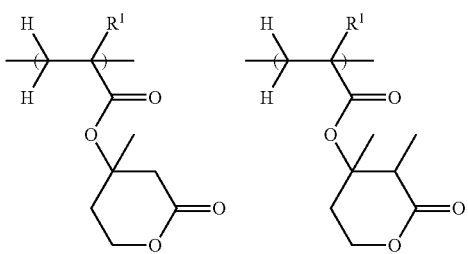
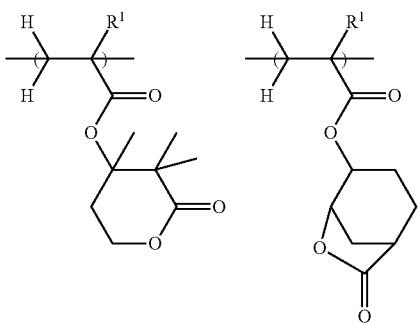
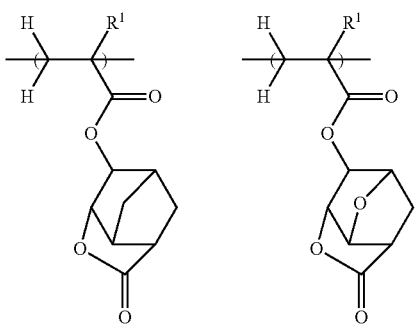
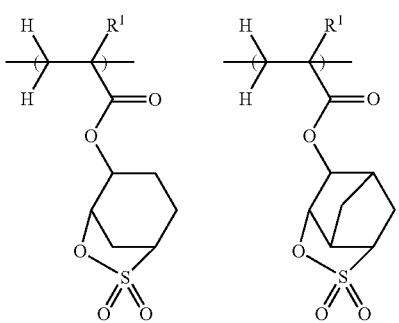
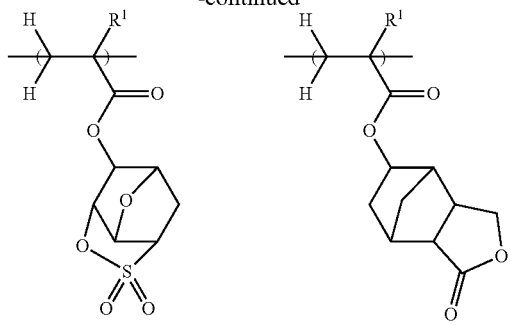
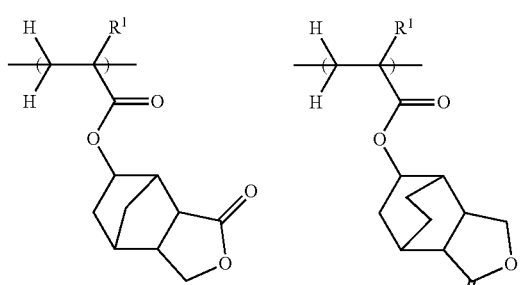
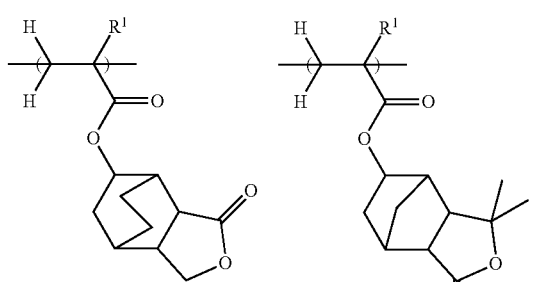
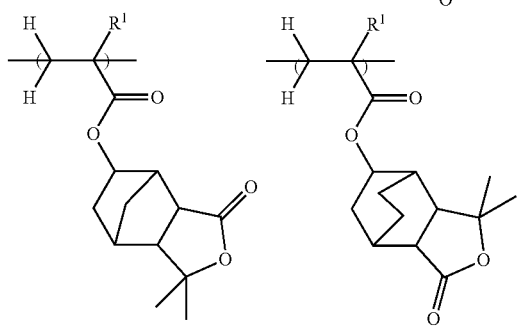
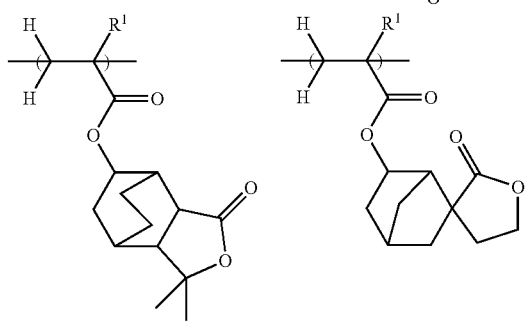

-continued
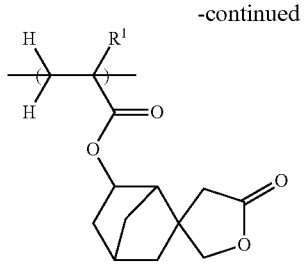
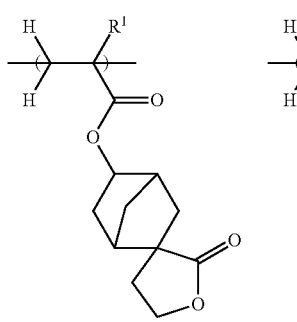
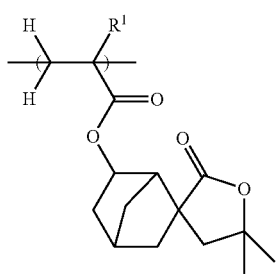
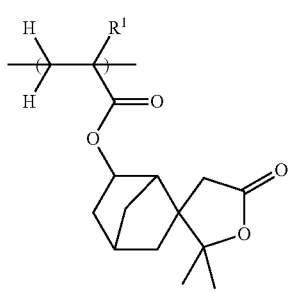
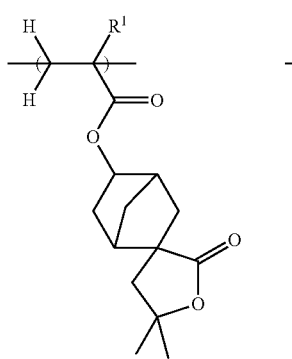
-continued
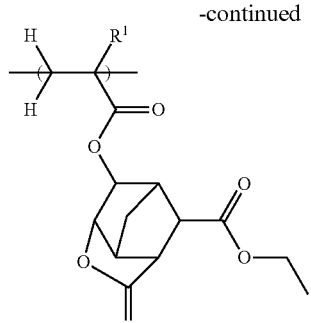
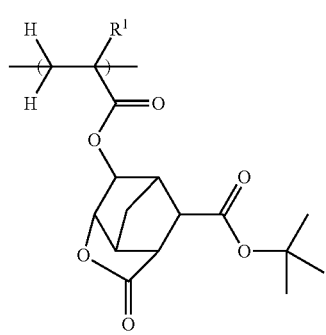
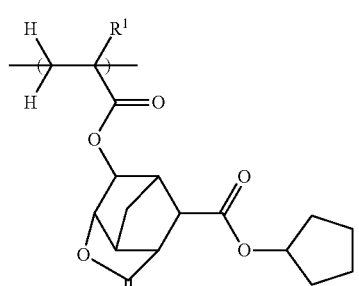
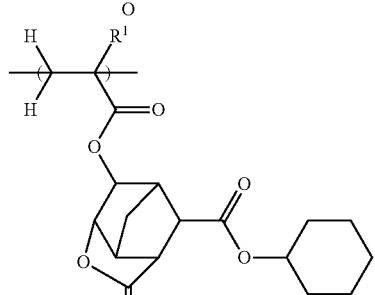
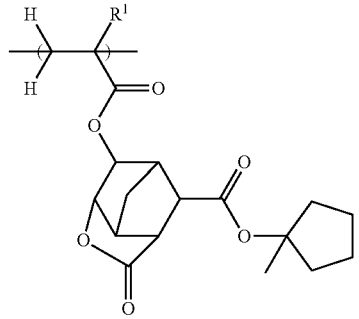

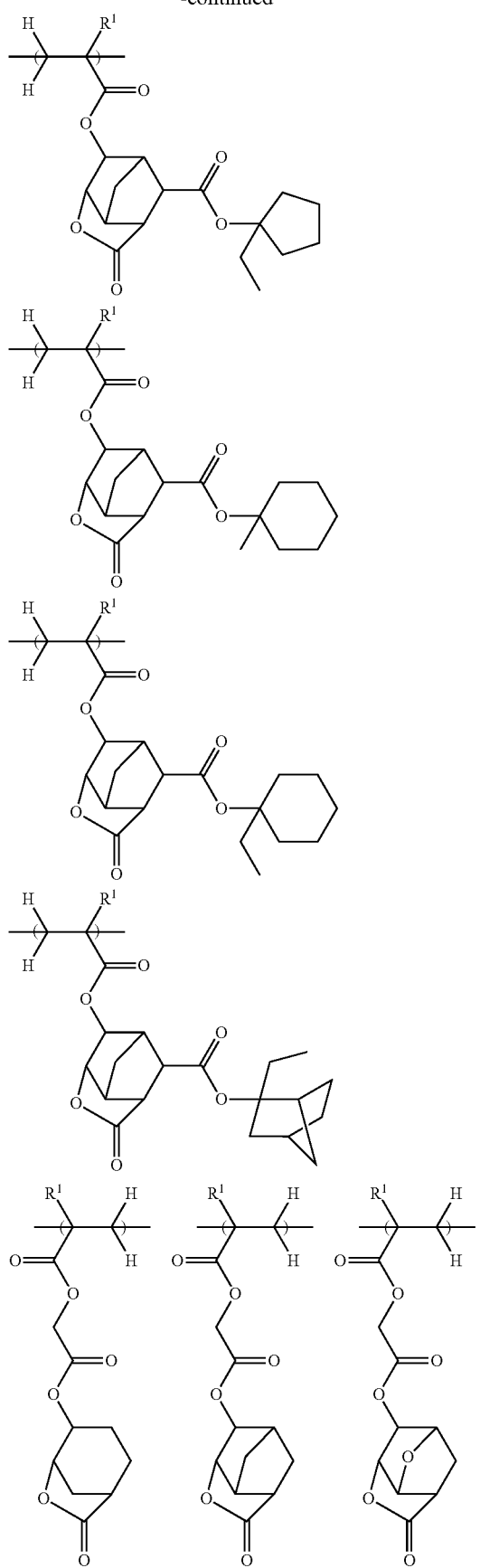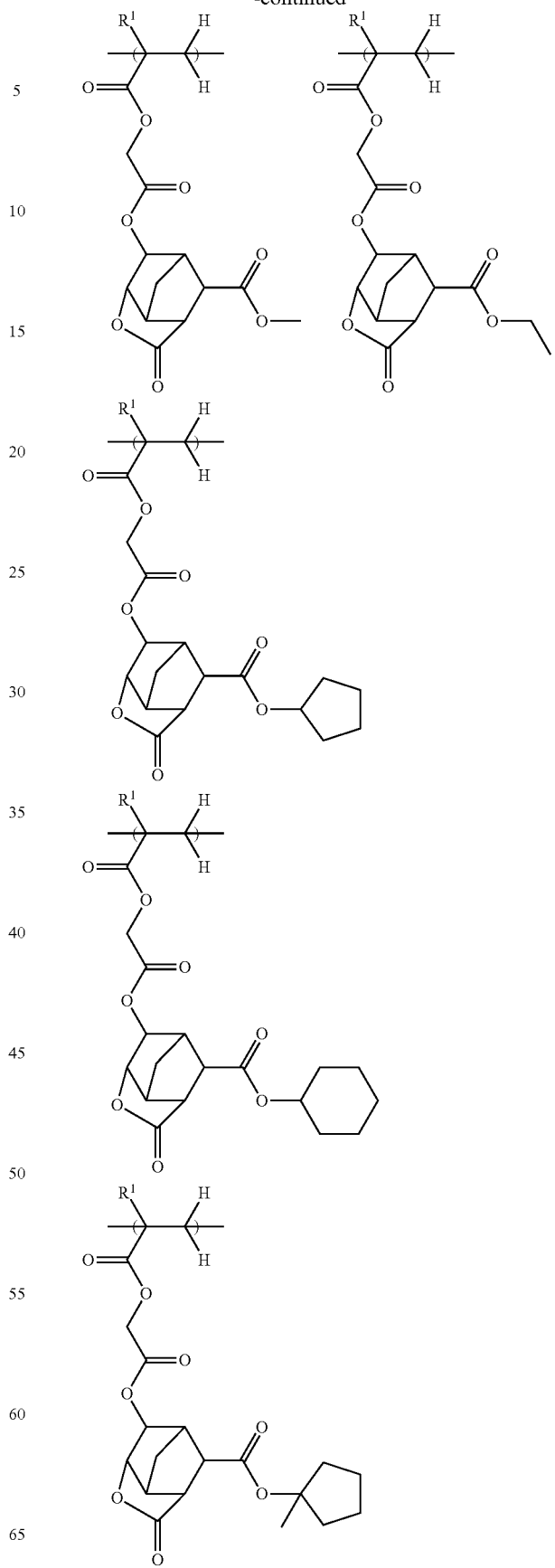

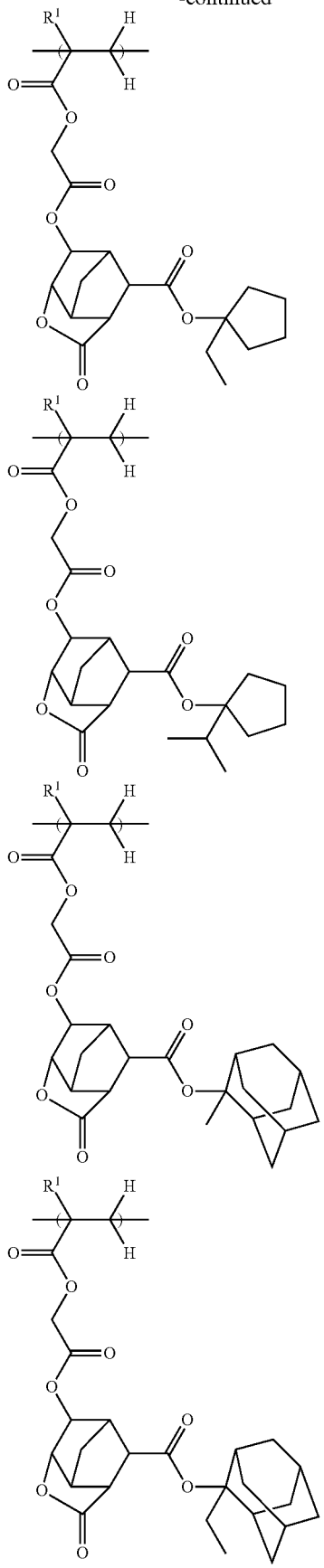
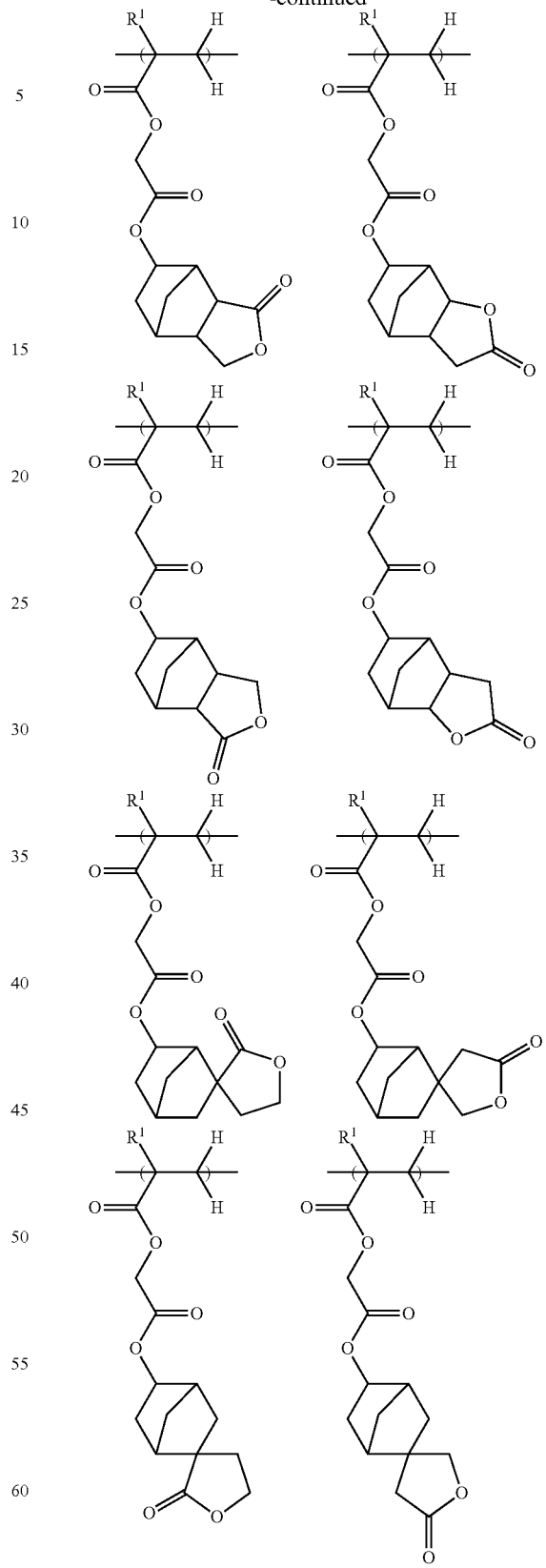
Illustrative examples of the recurring units having formula (7) are given below, but not limited thereto. Herein $R^1$ is as defined above.

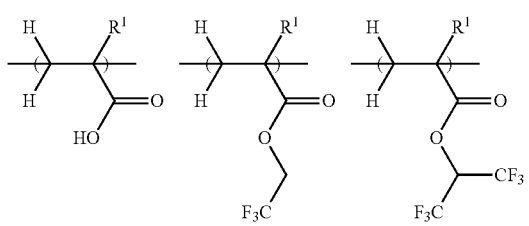
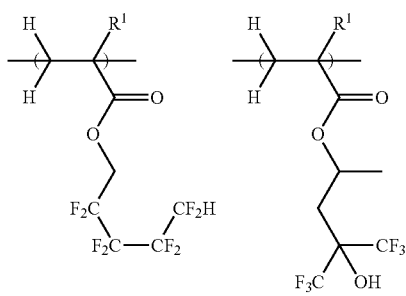
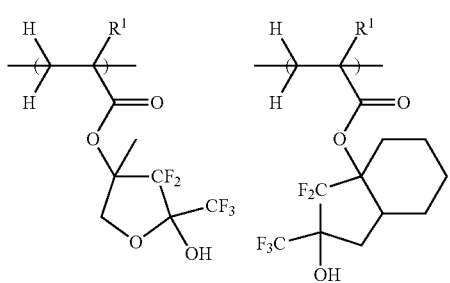
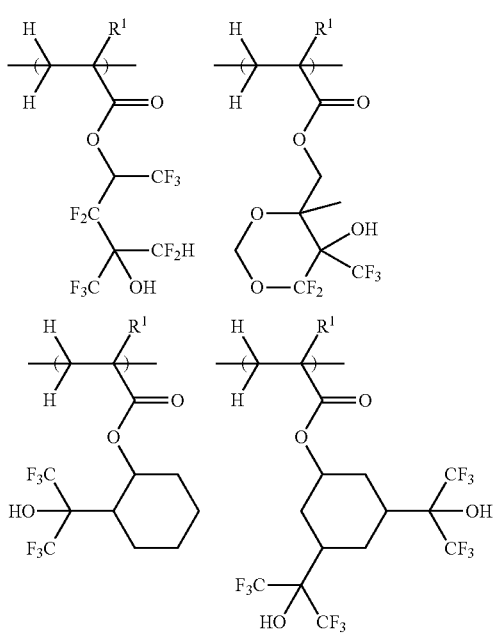
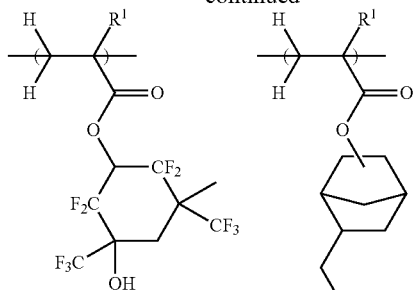
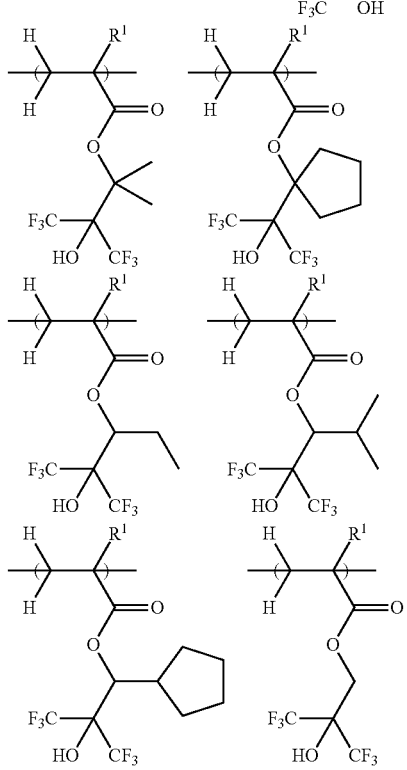

In addition to the foregoing units, the polymer may further comprise recurring units derived from carbon-to-carbon double bond-bearing monomers other than the above-described ones, for example, substituted acrylic acid esters such as methyl methacrylate, methyl crotonate, dimethyl maleate and dimethyl itaconate, unsaturated carboxylic acids such as maleic acid, fumaric acid, and itaconic acid, cyclic olefins such as norbornene, norbornene derivatives, and tetracyclo[$4.4.0.1^{2,5}.1^{7,10}$]dodecene derivatives, unsaturated acid anhydrides such as itaconic anhydride, and other monomers.

The polymer should preferably have a weight average molecular weight (Mw) in the range of 1,000 to 500,000, and more preferably 3,000 to 100,000, as measured versus polystyrene standards by GPC using tetrahydrofuran solvent. Outside the range, there may result a substantial loss of etch resistance, a failure to provide a contrast before and after exposure, and a lowering of resolution.

If a polymer has a wide molecular weight distribution or dispersity (Mw/Mn), which indicates the presence of lower and higher molecular weight polymer fractions, there is a possibility that foreign matter is left on the pattern or the pattern profile is degraded. The influences of molecular weight and dispersity become stronger as the pattern rule becomes finer. Therefore, the polymer should preferably have a narrow dispersity (Mw/Mn) of 1.0 to 2.0, especially 1.0 to 1.5, in order to provide a resist composition suitable for micropatterning to a small feature size.

The polymer may be synthesized by any desired methods, for example, by dissolving one or more unsaturated bond-bearing monomers corresponding to the recurring unit having formula (1) and optionally selected recurring units having formulae (4) to (7) in an organic solvent, adding a radical polymerization initiator thereto, and effecting heat polymerization. Examples of the organic solvent which can be used for polymerization include toluene, benzene, tetrahydrofuran, diethyl ether, dioxane, methyl ethyl ketone (MEK), propylene glycol monomethyl ether acetate (PG-MEA), and γ-butyrolactone (GBL). Examples of the polymerization initiator used herein include 2,2'-azobisisobutyronitrile (AIBN), 2,2'-azobis(2,4-dimethylvaleronitrile), dimethyl 2,2-azobis(2-methylpropionate), benzoyl peroxide, and lauroyl peroxide. Preferably the system is heated at 50 to 150° C., preferably 60 to 100° C. for polymerization to take place. The reaction time is preferably 2 to 24 hours. The acid labile group that has been incorporated in the monomer may be kept as such, or polymerization may be followed by protection or partial protection. During the polymer synthesis, any known chain transfer agent such as dodecyl mercaptan or 2-mercaptoethanol may be added for molecular weight control purpose. The amount of chain transfer agent added is preferably 0.01 to 10 mol % based on the total moles of monomers to be polymerized.

In the polymer, the recurring units derived from the inventive monomer and other monomers are preferably incorporated in the following molar fractions (mol %):
(I) more than 0 mol % to 99 mol %, preferably 5 to 70 mol %, and more preferably 10 to 60 mol % of recurring units of at least one type selected from formulae (1) to (3);
(II) 1 mol % to less than 100 mol %, preferably 1 to 95 mol %, and more preferably 20 to 90 mol % of recurring units of at least one type selected from formulae (4) to (7); and
(III) 0 to 80 mol %, preferably 0 to 70 mol %, and more preferably 0 to 50 mol % of other recurring units. The inventive polymer is not limited to the above range.

Resist Composition

A second embodiment of the invention is a resist composition comprising (A) a base resin comprising the inventive polymer, (B) a photoacid generator, and (C) a solvent.

The base resin (A) contains the inventive polymer defined above. The inventive polymer may be used alone or as a mixture of polymers which differ in compositional ratio, Mw and/or Mw/Mn. The base resin may further contain another polymer containing none of recurring units of formulae (1) to (3), for example, at least one polymer selected from polymers comprising recurring units having formulae (4) to (7).

In the base resin (A), the inventive polymer is preferably present in an amount of at least 40% by weight, more preferably at least 80% by weight, and most preferably 100% by weight.

The resist composition comprises the PAG as component (B), which is preferably selected from PAGs having the formulae (B-1), (B-2) and (B-3).

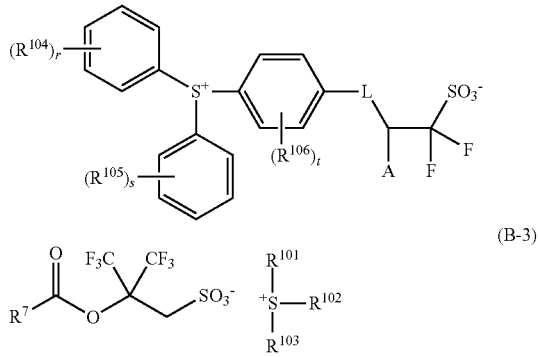

Herein A is hydrogen or trifluoromethyl. $R^7$ is a $C_3$-$C_{35}$ straight, branched or cyclic monovalent hydrocarbon group which may contain an oxygen atom, a nitrogen-containing heterocyclic group, or a group of the formula (i):

$$(R^8)(R^9)N-R^{10}- \quad (i)$$

wherein $R^8$ and $R^9$ are each independently hydrogen or a $C_3$-$C_{20}$ monovalent hydrocarbon group which may contain a heteroatam, $R^8$ and $R^9$ may bond together to form a ring with the nitrogen atom to which they are attached, $R^{30}$ is a $C_1$-$C_{20}$ divalent hydrocarbon group which may contain a heteroatom.

$R^{101}$, $R^{102}$ and $R^{103}$ are each independently an optionally substituted $C_1$-$C_{10}$ straight or branched alkyl, alkenyl or oxoalkyl group, or an optionally substituted $C_6$-$C_{18}$ aryl, aralkyl or aryloxoalkyl group, any two of $R^{101}$, $R^{102}$ and $R^{103}$ may bond together to form a ring with the sulfur atom to which they are attached. $R^{104}$, $R^{105}$ and $R^{106}$ are each independently hydrogen or a $C_1$-$C_{20}$ straight, branched or cyclic monovalent hydrocarbon group which may contain a heteroatom, r and s are each independently an integer of 0 to 5, t is an integer of 0 to 4. L is a single bond or a $C_1$-$C_{20}$ straight, branched or cyclic divalent hydrocarbon group which may contain a heteroatom.

Examples of the monovalent hydrocarbon group which may contain an oxygen atom, represented by $R^7$, include alkyl groups such as methyl, ethyl, propyl, isopropyl, n-butyl, sec-butyl, tert-butyl, pentyl, hexyl, heptyl, octyl, cyclopentyl, cyclohexyl, cycloheptyl, cyclopropylmethyl, 4-methylcyclohexyl, cyclohexylmethyl, norbornyl, 1-adamantyl, 1-adamantylmethyl, and steroid structure-containing alkyl groups; oxoalkyl groups such as 2-oxocyclopentyl, 2-oxocyclohexyl, 4-oxocyclohexyl, 2-oxopropyl, 2-oxoethyl, 2-cyclopentyl-2-oxoethyl, 2-cyclohexyl-2-oxoethyl, 2-(4-methylcyclohexyl)-2-oxoethyl, 4-oxatricyclo[4.2.1.0$^{3,7}$]nonan-5-on-9-yl, 4-oxo-1-adamantyl; aryl groups, for example, alkoxyphenyl groups such as phenyl, 1-naphthyl, 2-naphthyl, anthranyl, thienyl, 4-hydroxyphenyl, 4-methoxyphenyl, 3-methoxyphenyl, 2-methoxyphenyl, 4-ethoxyphenyl, 4-tert-butoxyphenyl, and 3-tert-butoxyphenyl; alkylphenyl groups such as 2-methylphenyl, 3-methylphenyl, 4-methylphenyl, 4-ethylphenyl, 4-tert-butylphenyl, 4-n-butylphenyl, and 2,4-dimethylphenyl, alkylnaphthyl groups such as methylnaphthyl and ethylnaphthyl; alkoxynaphthyl groups such as methoxynaphthyl and ethoxynaphthyl; dialkylnaphthyl groups such as dimethylnaphthyl and diethylnaphthyl; dialkoxynaphthyl groups such as dimethoxynaphthyl and diethoxynaphthyl; aralkyl groups such as benzyl, 1-phenylethyl and 2-phenylethyl; aryloxyalkyl groups such as 2-aryl-2-oxoethyl groups, e.g., 2-phenyl-2-oxoethyl, 2-(1-naphthyl)-2-oxoethyl, and 2-(2-naphthyl)-2-oxoethyl. Also included are vinyl and isopropenyl groups.

Examples of the nitrogen-containing heterocyclic group represented by $R^7$ include aziridine, pyrrolidine, piperidine, morpholine, pyrrole, pyridine, azetidine, oxazole, isooxazole, thiazole, isothiazole, imidazole, pyrazole, pyridazine, pyrimidine, pyrazine, pyrroline, 2-imidazoline, imidazolidine, 3-pyrazoline, pyrazolidine, piperazine, triazine, oxadiazine, dithiazine, indole, isoindole, quinoline, isoquinoline, cinnoline, phthalazine, quinazoline, quinoxaline, 1,8-naphthylidine, purine, pteridine, indolizine, carbazole, acridine, phenazine, phenanthridine, 1,10-phenanthroline, phenoxazine, indoline, isoindoline, quinuclidine, benzo[e]indole, and benzo[cd]indole.

Of the foregoing groups $R^7$, tert-butyl, cyclohexyl, 1-adamantyl, 1-adamantylmethyl, 4-oxa-tricyclo[4.2.1.0$^{37}$]nonan-5-on-9-yl, 4-oxo-1-adamantyl, and steroid structure-containing alkyl groups are especially preferred.

In formula (i), examples of the monovalent hydrocarbon group represented by $R^8$ and $R^9$ include alkyl groups such as methyl, ethyl, propyl, isopropyl, n-butyl, sec-butyl, tert-butyl, pentyl, hexyl, heptyl, octyl, cyclopentyl, cyclohexyl, cycloheptyl, cyclopropylmethyl, 4-methylcyclohexyl, cyclohexylmethyl, norbornyl, and adamantyl; alkenyl groups such as vinyl, allyl, propenyl, butenyl, hexenyl and cyclohexenyl, aryl groups such as phenyl, naphthyl and thienyl; and aralkyl groups such as benzyl, 1-phenylethyl and 2-phenylethyl. In the foregoing hydrocarbon groups, at least one hydrogen atom may be substituted by a hydrocarbon moiety as mentioned above or a moiety containing a heteroatom (such as oxygen, sulfur, nitrogen or halogen), or a moiety containing a heteroatom (such as oxygen, sulfur or nitrogen) may intervene between carbon atoms, so that the group may contain a hydroxyl, cyano, carbonyl, ether, ester, sulfonic acid ester, carbonate, lactone ring, sultone ring, carboxylic acid anhydride, or haloalkyl moiety.

When $R^8$ and $R^9$ bond together to form a ring with the nitrogen atom to which they are attached, suitable rings include aziridine, pyrrolidine, piperidine, morpholine, pyrrole, pyridine, azetidine, oxazole, isooxazole, thiazole, isothiazole, imidazole, pyrazole, pyridazine, pyrimidine, pyrazine, pyrroline, 2-imidazoline, imidazolidine, 3-pyrazoline, pyrazolidine, piperazine, triazine, oxadiazine, dithiazine, indole, isoindole, quinoline, isoquinoline, cinnoline, phthalazine, quinazoline, quinoxaline, 1,8-naphthylidine, purine, pteridine, indolizine, carbazole, acridine, phenazine, phenanthridine, 1,10-phenanthroline, phenoxazine, indoline, isoindoline, quinuclidine, benzo[e]indole, and benzo[cd]indole. In the foregoing rings, at least one hydrogen atom may be substituted by a hydrocarbon moiety as mentioned above or a moiety containing a heteroatom (such as oxygen, sulfur, nitrogen or halogen), or a moiety containing a heteroatom (such as oxygen, sulfur or nitrogen) may intervene between carbon atoms, so that the ring may contain a hydroxyl, cyano, carbonyl, ether, ester, sulfonic acid ester, carbonate, lactone ring, sultone ring, carboxylic acid anhydride, or haloalkyl moiety.

In formula (i), $R^{10}$ is a $C_1$-$C_{20}$ divalent hydrocarbon group which may contain a heteroatom. Suitable divalent hydrocarbon groups include straight alkanediyl groups such as methylene, ethylene, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, tridecane-1,13-diyl, tetradecane-1,14-diyl, pentadecane-1,15-diyl, hexadecane-1,16-diyl, and heptadecane-1,17-diyl; branched alkanediyl groups corresponding to the foregoing straight alkanediyl groups to which a pendant such as methyl, ethyl, propyl, isopropyl, butyl, sec-butyl or tert-butyl is attached; saturated cyclic hydrocarbon groups such as cyclopentanediyl, cyclohexanediyl, norbornanediyl and adamantanediyl; and unsaturated cyclic hydrocarbon groups such as phenylene and naphthylene. In the foregoing hydrocarbon groups, at least one hydrogen atom may be substituted by a moiety containing a heteroatom (such as oxygen, sulfur, nitrogen or halogen), or a moiety containing a heteroatom (such as oxygen, sulfur or nitrogen) may intervene between carbon atoms, so that the group may contain a hydroxyl, cyano, carbonyl, ether, ester, sulfonic acid ester, carbonate, lactone ring, sultone ring, carboxylic acid anhydride, or haloalkyl moiety.

In formulae (B-1) and (B-3), suitable groups represented by $R^{101}$, $R^{102}$ and $R^{103}$ include alkyl groups such as methyl, ethyl, propyl, isopropyl, n-butyl, sec-butyl, tert-butyl, pentyl, hexyl, heptyl, octyl, cyclopentyl, cyclohexyl, cycloheptyl, cyclopropylmethyl, 4-methylcyclohexyl, cyclohexylmethyl, norbornyl, and adamantyl; alkenyl groups such as vinyl, allyl, propenyl, butenyl, hexenyl and cyclohexenyl; oxoalkyl groups such as 2-oxocyclopentyl, 2-oxocyclohexyl, 2-oxopropyl, 2-oxoethyl, 2-cyclopentyl-2-oxoethyl, 2-cyclohexyl-2-oxoethyl, and 2-(4-methylcyclohexyl)-2-oxoethyl; aryl groups such as phenyl, naphthyl and thienyl; alkoxyphenyl groups such as 4-hydroxyphenyl, 4-methoxyphenyl, 3-methoxyphenyl, 2-methoxyphenyl, 4-ethoxyphenyl, 4-tert-butoxyphenyl, and 3-tert-butoxyphenyl; alkylphenyl groups such as 2-methylphenyl, 3-methylphenyl, 4-methylphenyl, 4-ethylphenyl, 4-tert-butylphenyl, 4-n-butylphenyl, and 2,4-dimethylphenyl, alkylnaphthyl groups such as methylnaphthyl and ethylnaphthyl; alkoxynaphthyl groups such as methoxynaphthyl and ethoxynaphthyl; dialkylnaphthyl groups such as dimethylnaphthyl and diethylnaphthyl, dialkoxynaphthyl groups such as dimethoxynaphthyl, and diethoxynaphthyl; aralkyl groups such as benzyl, 1-phenylethyl and 2-phenylethyl; aryloxoalkyl groups such as 2-aryl-2-oxoethyl groups, e.g., 2-phenyl-2-oxoethyl, 2-(1-naphthyl)-2-oxoethyl, and 2-(2-naphthyl)-2-oxoethyl. Also included are aryl groups substituted with a polymerizable substituent group such as acryloyloxy or methacryloyloxy, for example, 4-acryloyloxyphenyl, 4-methacryloyloxyphenyl, 4-acryloyloxy-3,5-dimethylphenyl, 4-methacryloyloxy-3,5-dimethylphenyl, 4-vinyloxyphenyl, and 4-vinylphenyl. When any two of $R^{101}$, $R^{102}$ and $R^{103}$ bond together to form a ring with the sulfur atom to which they are attached, a ring-forming combination is a divalent organic group such as 1,4-butylene or 3-oxa-1,5-pentylene.

Examples of the sulfonium cation in formulae (B-1) and (B-3) include, but are not limited to, triphenylsulfonium, 4-hydroxyphenyldiphenylsulfonium, bis(4-hydroxyphenyl)phenylsulfonium, tris(4-hydroxyphenyl) sulfonium, 4-tert-butoxyphenyldiphenylsulfonium, bis(4-tert-butoxyphenyl)phenylsulfonium, tris(4-tert-butoxyphenyl)sulfonium, 3-tert-butoxyphenyldiphenylsulfonium, bis(3-tert-butoxyphenyl)phenylsulfonium, tris(3-tert-butoxyphenyl)sulfonium, 3,4-di-tert-butoxyphenyldiphenylsulfonium, bis(3,4-di-tert-butoxyphenyl)phenylsulfonium, tris(3,4-di-tert-butoxyphenyl)sulfonium, diphenyl(4-thiophenoxyphenyl)sulfonium, 4-tert-butoxycarbonylmethyloxyphenyldiphenylsulfonium, tris(4-tert-butoxycarbonylmethyloxyphenyl)sulfonium, (4-tert-butoxyphenyl)bis(4-dimethylaminophenyl)sulfonium, tris(4-dimethylaminophenyl)sulfonium, 2-naphthyldiphenylsulfonium, (4-hydroxy-3,5-dimethylphenyl)diphenylsulfonium, (4-n-hexyloxy-3,5-dimethylphenyl)diphenylsulfonium, dimethyl(2-naphthyl)sulfonium, 4-hydroxyphenyldimethylsulfonium, 4-methoxyphenyldimethylsulfonium, trimethylsulfonium, 2-oxocyclohexylcyclohexylmethylsulfonium, trinaphthylsulfonium, tribenzylsulfonium, diphenylmethylsulfonium, dimethylphenylsulfonium, 2-oxo-2-phenylethylthiacyclopentanium, diphenyl-2-thienylsulfonium, 4-n-butoxynaphthyl-1-thiacyclopentanium, 2-n-butoxynaphthayl-1-thiacyclopentanium, 4-methoxynaphthyl-1-thiacyclopentanium, and 2-methoxynaphthyl-1-thiacyclopentanium. Of these, triphenylsulfonium, 4-tert-butylphenyldiphenylsulfonium, 4-tert-butoxyphenyldiphenylsulfonium, tris(4-tert-butylphenyl) sulfonium and 4-tert-butoxycarbonylmethyloxyphenyldiphenylsulfonium are more preferred.

In formula (B-2), $R^{104}$, $R^{105}$ and $R^{106}$ are each independently hydrogen or a $C_1$-$C_{20}$ straight, branched or cyclic monovalent hydrocarbon group which may contain a heteroatom. Suitable monovalent hydrocarbon groups include methyl, ethyl, propyl, isopropyl, n-butyl, sec-butyl, tert-butyl, tert-pentyl, n-pentyl, n-hexyl, n-octyl, n-nonyl, n-decyl, cyclopentyl, cyclohexyl, 2-ethylhexyl, cyclopentylmethyl, cyclopentylethyl, cyclopentylbutyl, cyclohexylmethyl, cyclohexylethyl, cyclohexylbutyl, norbornyl, oxanorbornyl, tricyclo[5.2.1.0$^{2,6}$]decanyl, and adamantyl. In the foregoing hydrocarbon groups, at least one hydrogen atom may be substituted by a moiety containing a heteroatom (such as oxygen, sulfur, nitrogen or halogen), or a moiety containing a heteroatom (such as oxygen, sulfur or nitrogen) may intervene between carbon atoms, so that the group may contain a hydroxyl, cyano, carbonyl, ether, ester, sulfonic acid ester, carbonate, lactone ring, sultone ring, carboxylic acid anhydride, or haloalkyl moiety. Of these, methyl, methoxy, tert-butyl and tert-butoxy are preferred as $R^{104}$, $R^{105}$ and $R^{106}$.

In formula (B-2), L is a single bond or a $C_1$-$C_{20}$ straight, branched or cyclic divalent hydrocarbon group which may contain a heteroatom. Suitable divalent hydrocarbon groups are as exemplified above for $R^{10}$, and a combination of two or more such groups is also acceptable. In these hydrocarbon groups, at least one hydrogen atom may be substituted by a moiety containing a heteroatom (such as oxygen, sulfur, nitrogen or halogen), or a moiety containing a heteroatom (such as oxygen, sulfur or nitrogen) may intervene between carbon atoms, so that the group may contain a hydroxyl, cyano, carbonyl, ether, ester, sulfonic acid ester, carbonate, lactone ring, sultone ring, carboxylic acid anhydride, or haloalkyl moiety.

Exemplary structures of the anion moiety in the PAGs having formulae (B-1) and (B-3) are shown below, but not limited thereto. Herein A is as defined above.

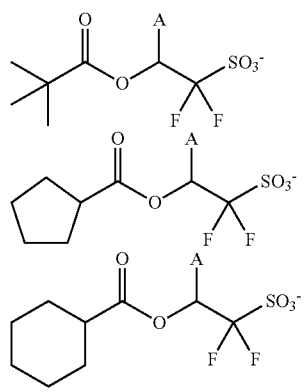

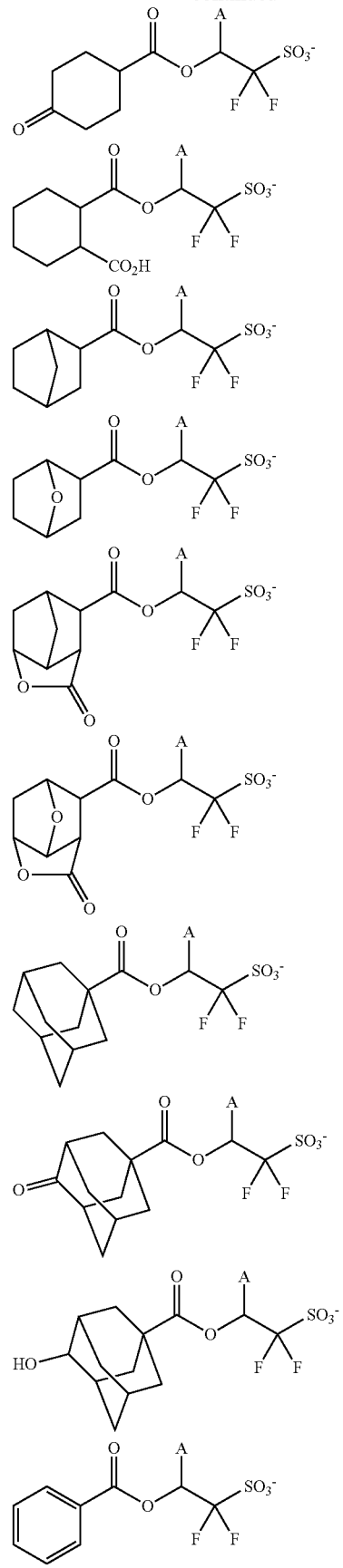

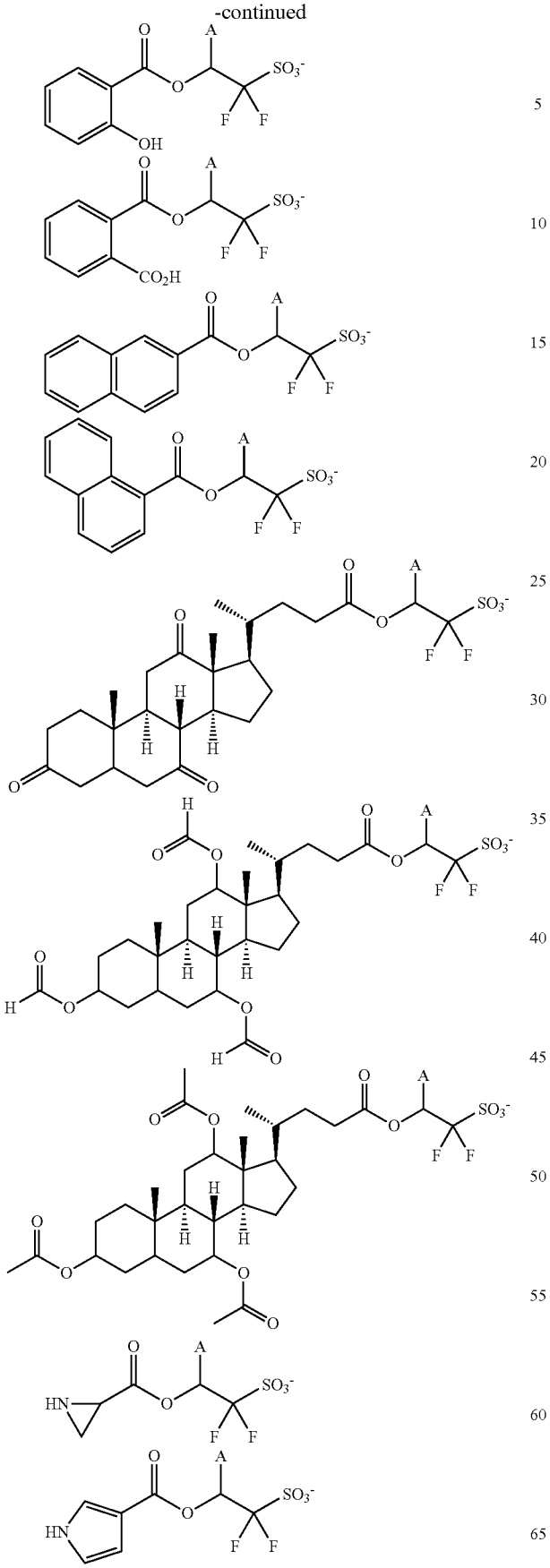
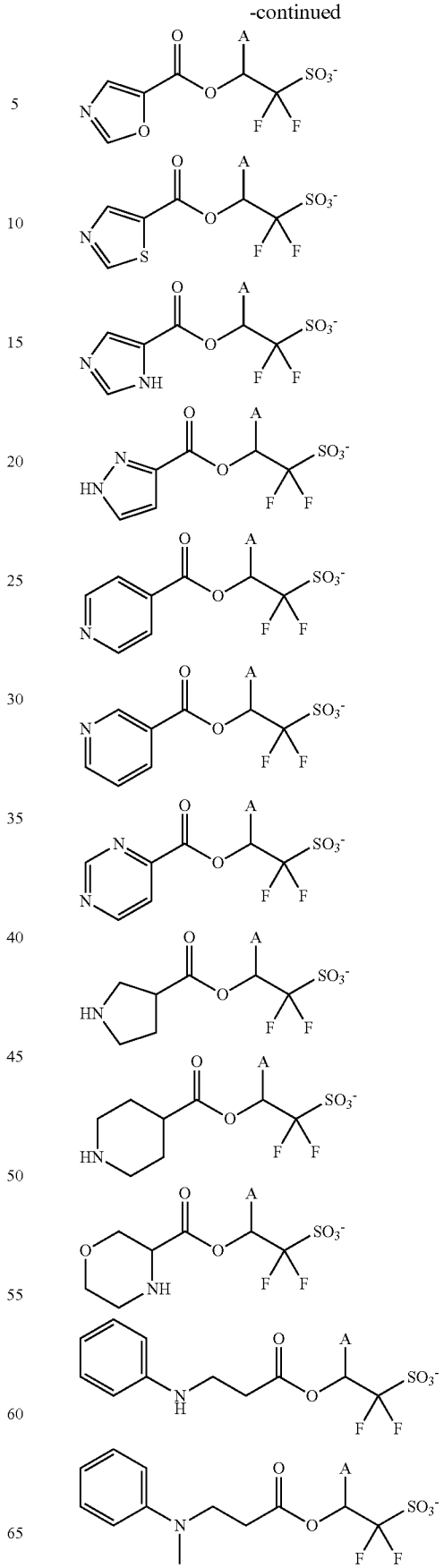

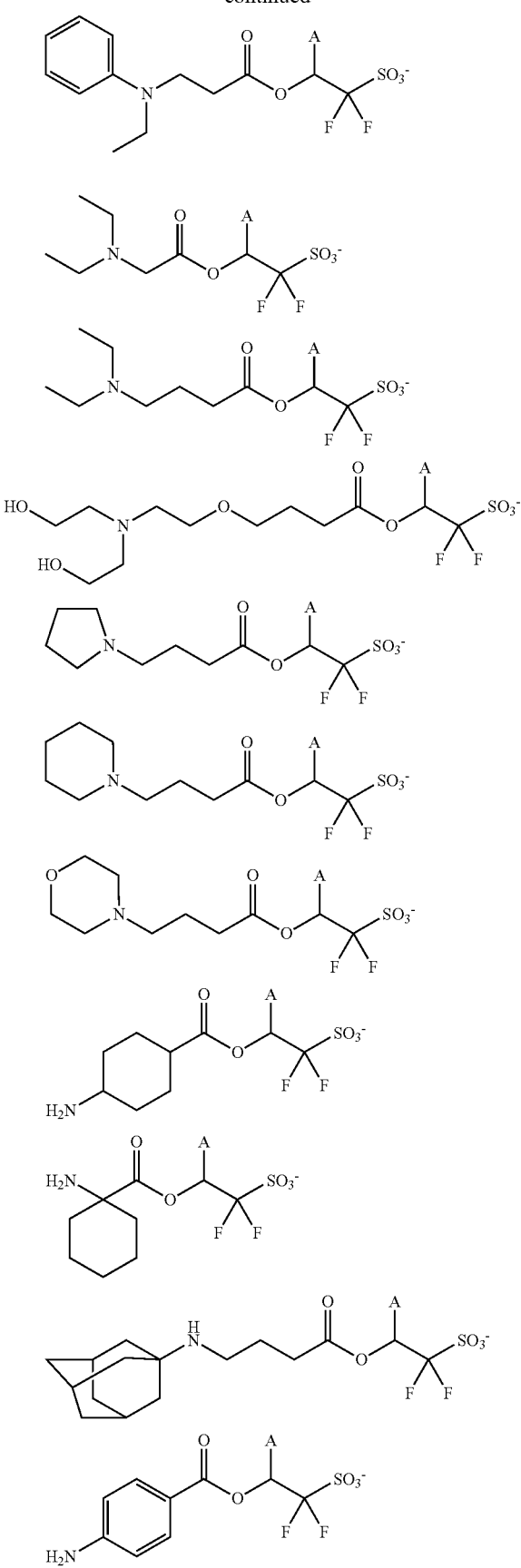
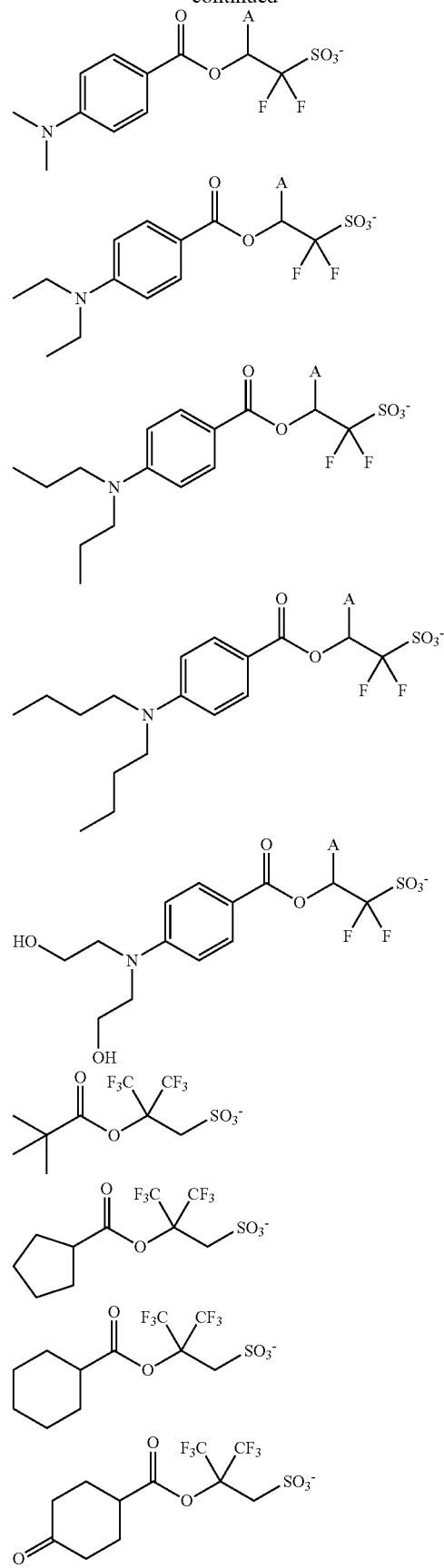

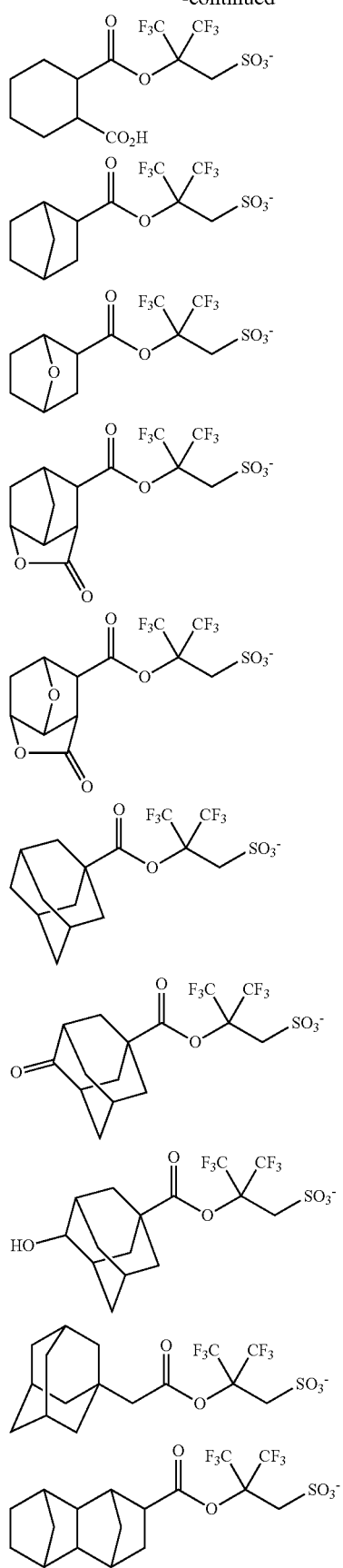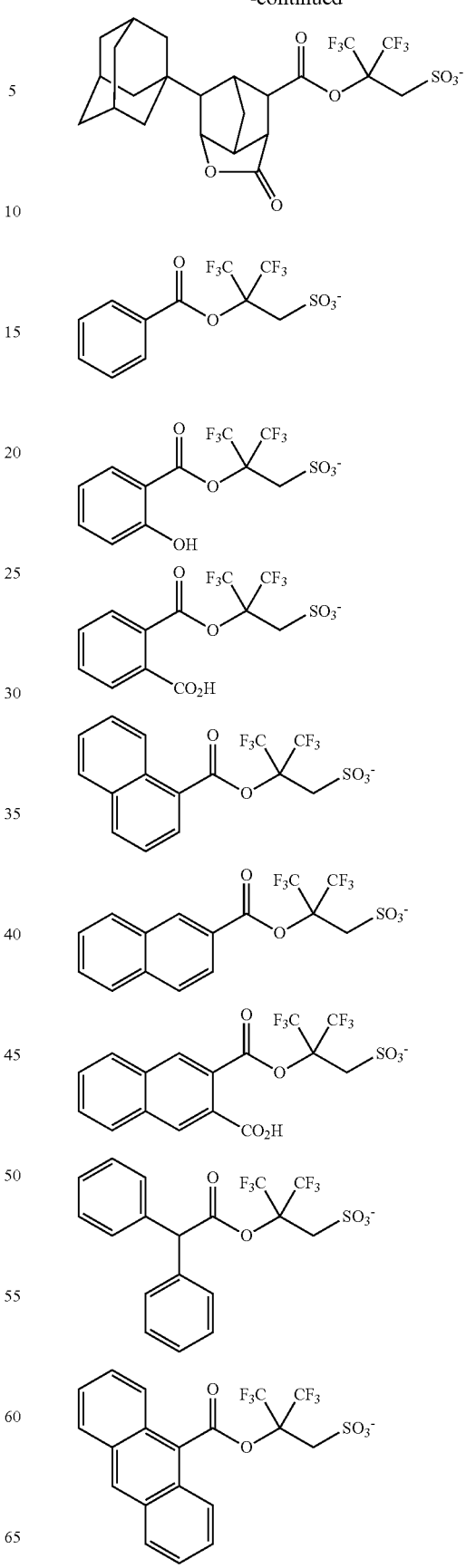

121
-continued
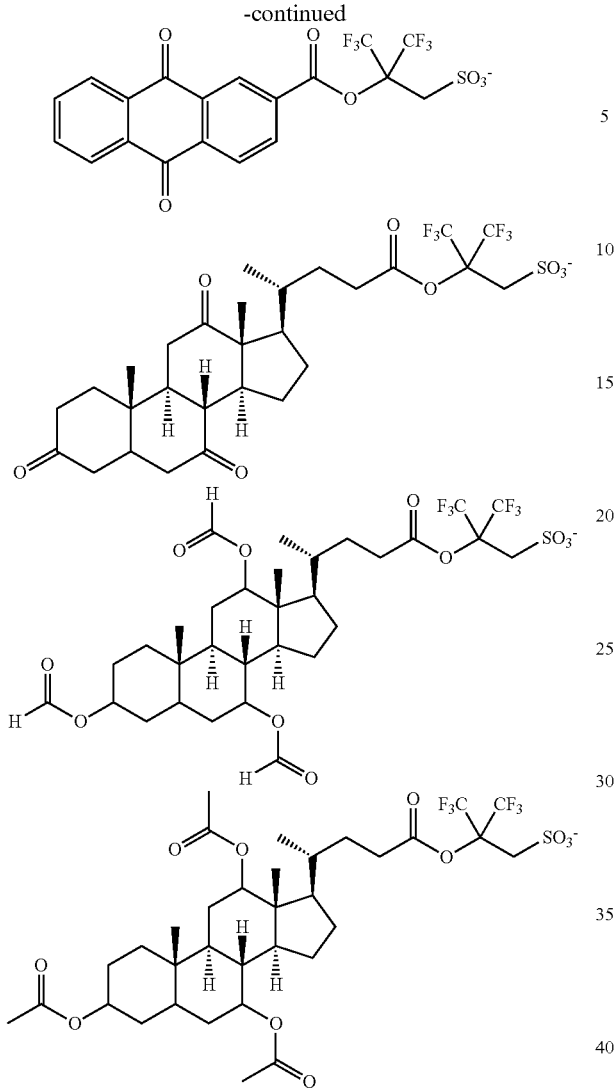
Exemplary structures of the cation moiety in the PAGs having formulae (B-1) and (B-3) are shown below, but not limited thereto.
122
-continued
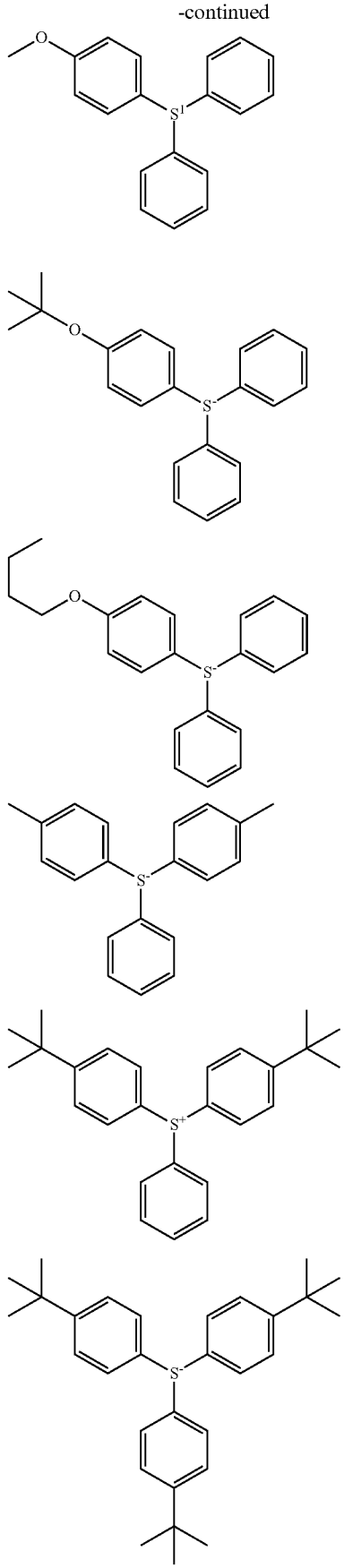

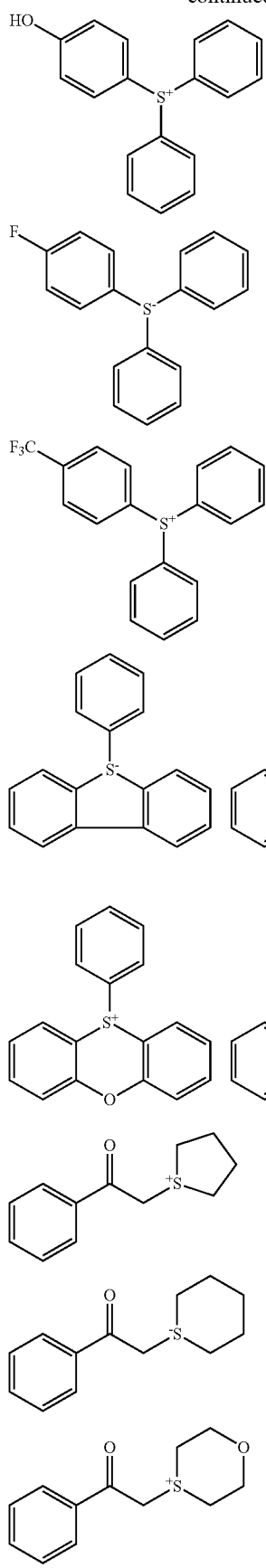
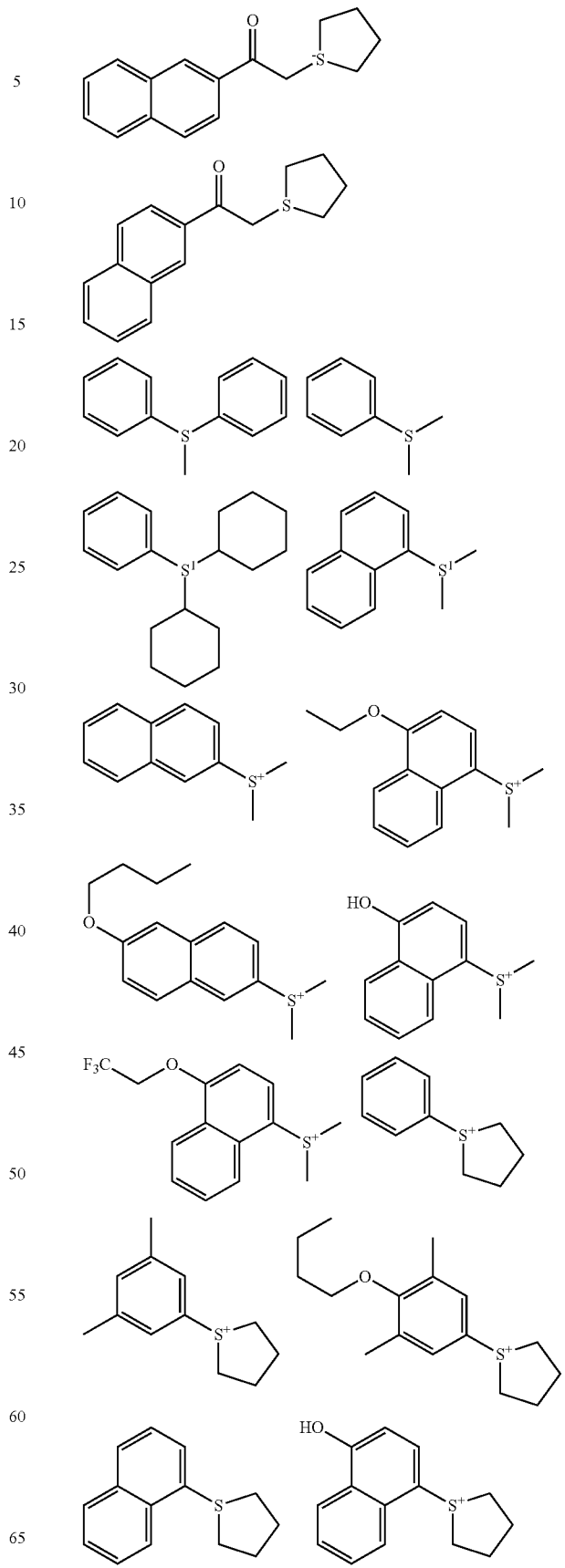

125
-continued
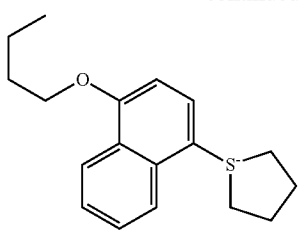
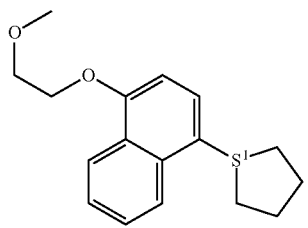
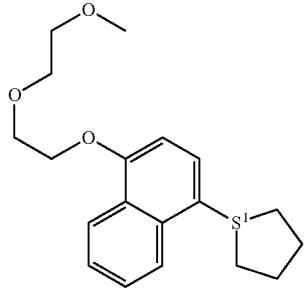
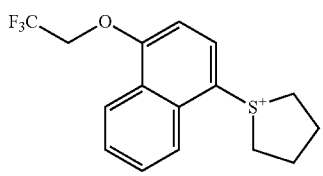
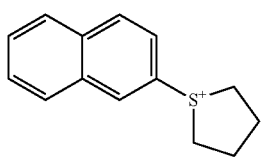
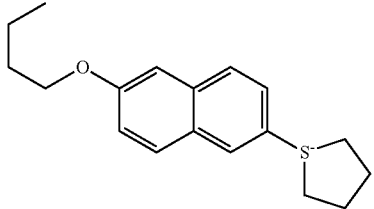
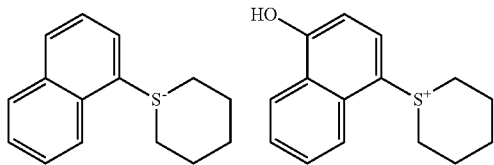
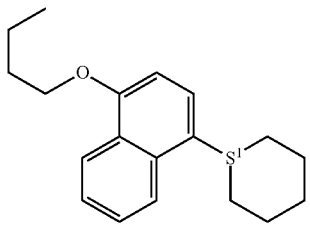
126
-continued
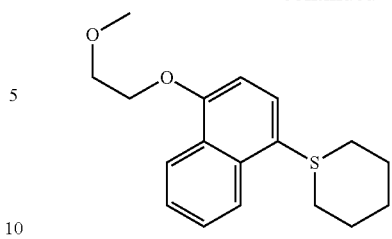
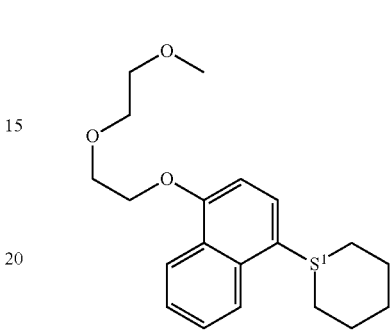
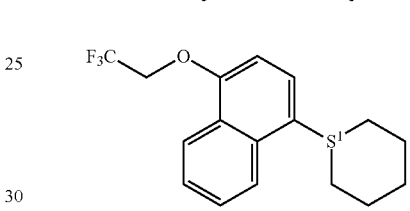
Examples of the PAG having formula (B-2) are shown below, but not limited thereto. Herein A is as defined above.
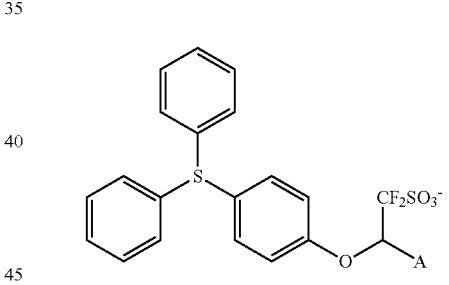
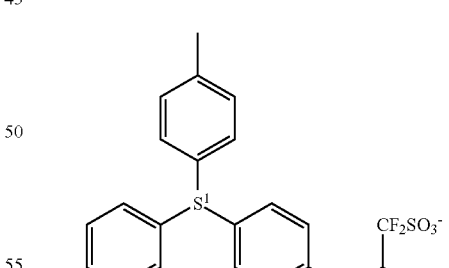
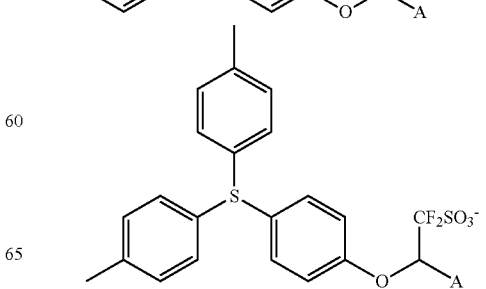

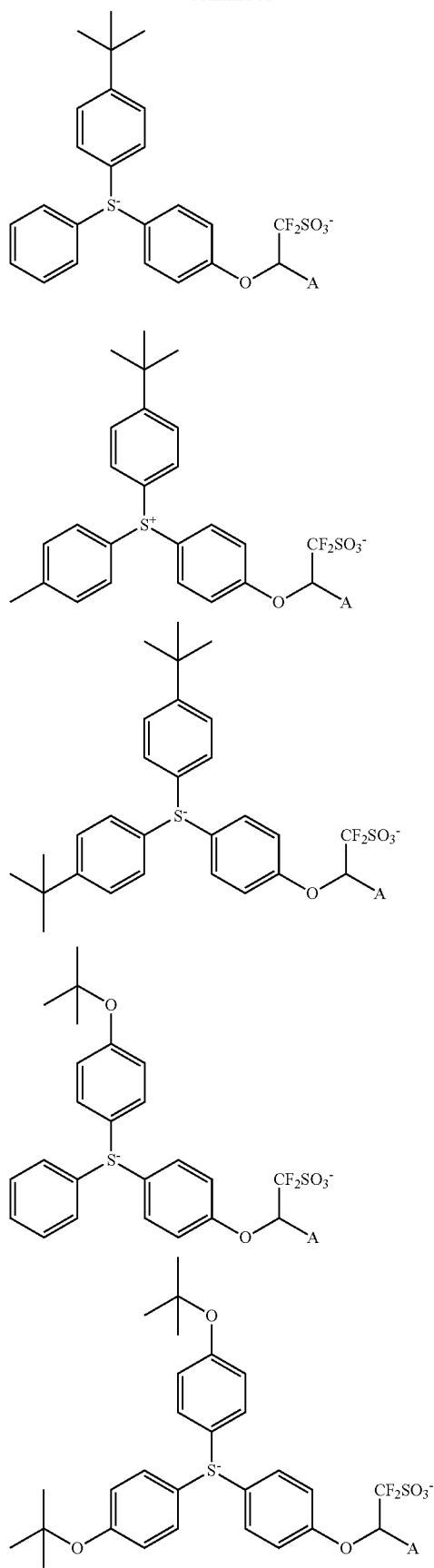
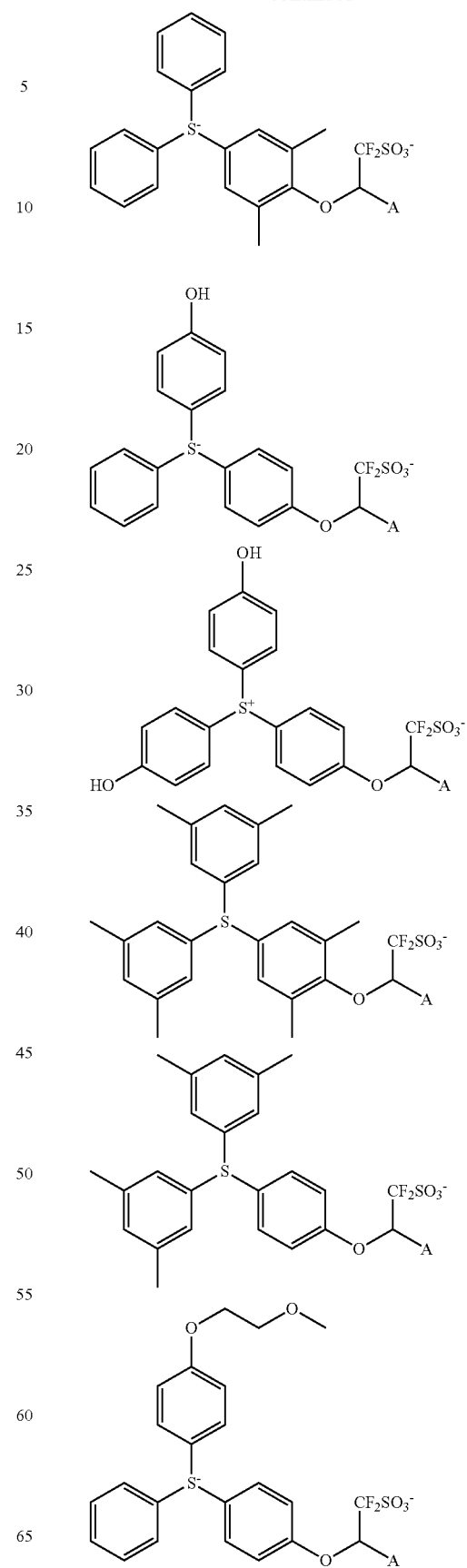

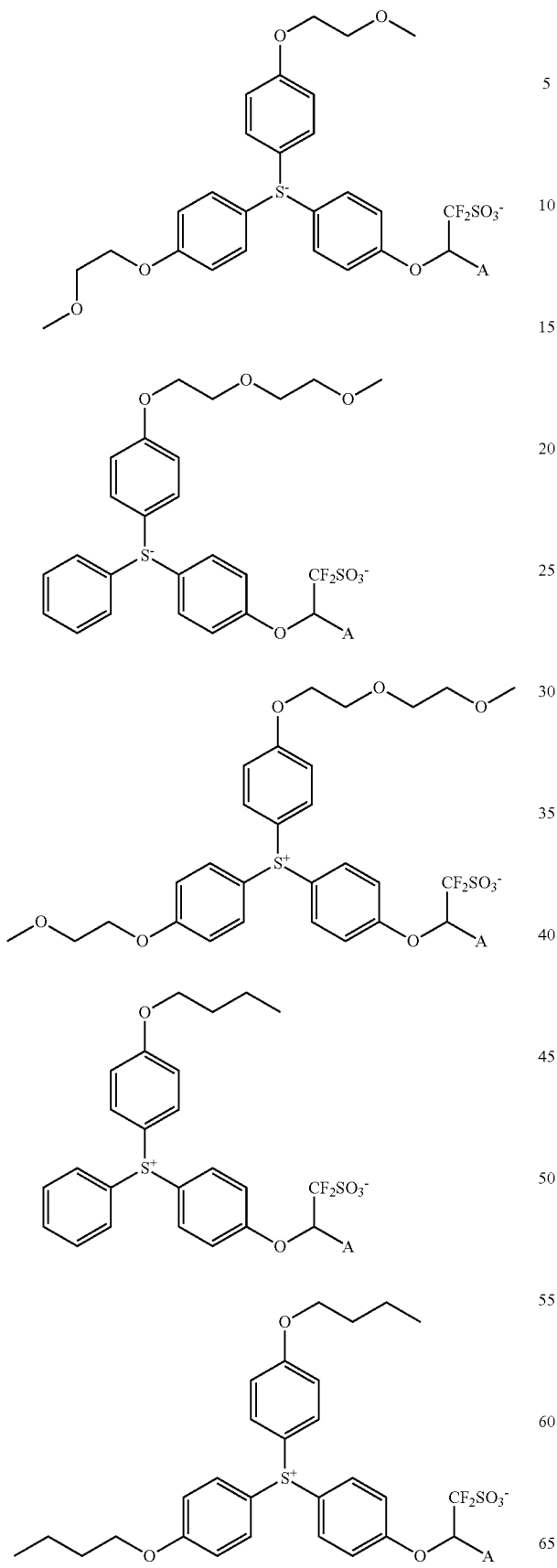
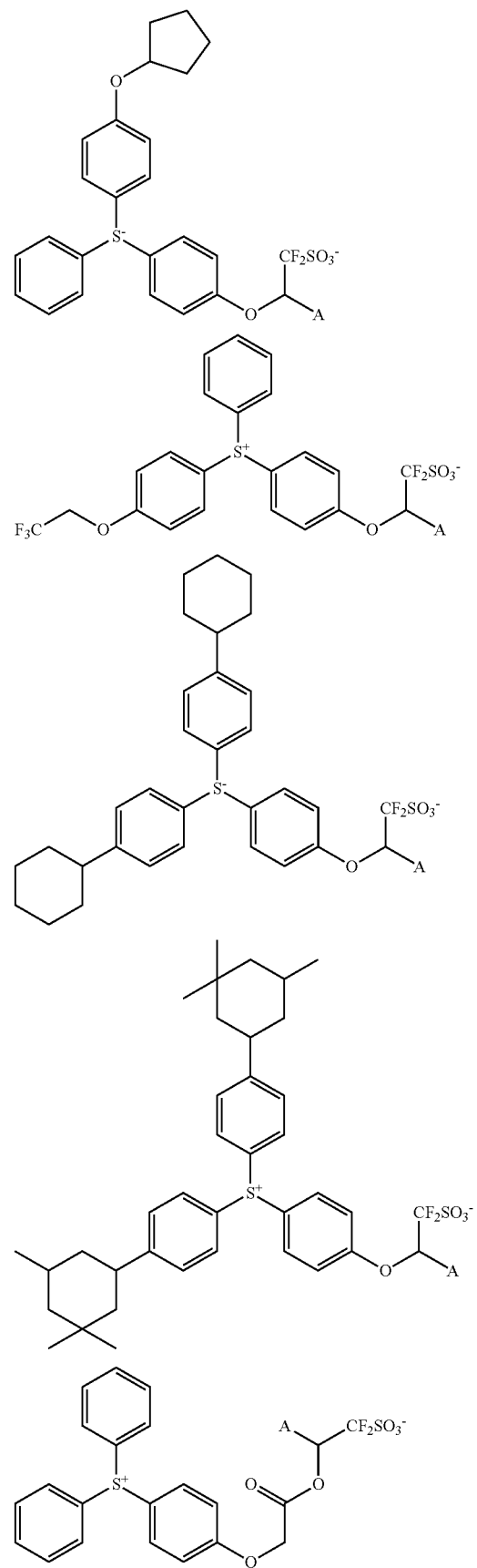

-continued

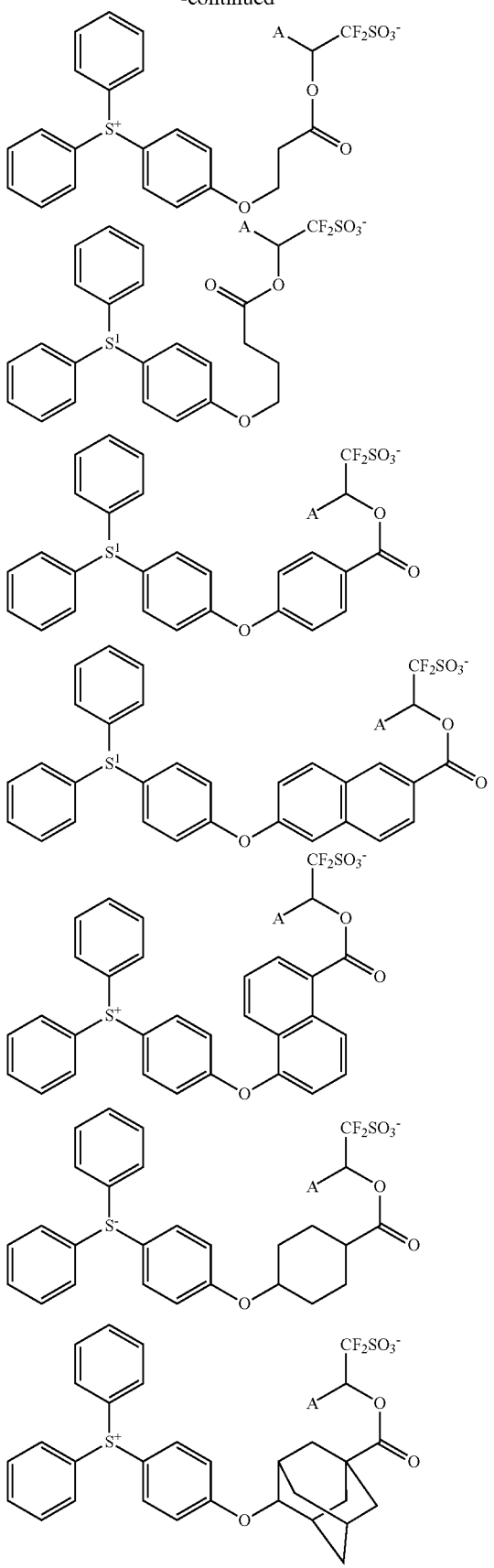

Preferably the PAG (B) is used in an amount of 0.1 to 40 parts, more preferably 0.1 to 20 parts, and even more preferably 0.1 to 15 parts by weight per 100 parts by weight of the base resin. Too much amounts of the PAG may give rise to problems including degraded resolution and foreign particles after resist development or during stripping.

In the resist composition, a PAG other than the PAGs of formulae (B-1) to (B-3) may be included for the purpose of fine adjustment of lithography performance. The other PAG may be any compound capable of generating an acid upon exposure to high-energy radiation. It may be any of well-known acid generators used in conventional resist compositions, especially chemically amplified resist compositions. Suitable PAGs include sulfonium salts, iodonium salts, sulfonyldiazomethane, N-sulfonyloxyimide, and oxime-O-sulfonate acid generators, which may be used alone or in admixture. Examples of the acid generated by the other PAG include strong acids such as sulfonic acids, bis(perfluoroalkanesulfonyl)imide and tris(perfluoromethanesulfonyl)methide, and weak acids such as carboxylic acids.

Examples of the other PAG include the compounds described in JP-A 2008-111103, paragraphs [0122]-[0142], especially the compounds described in JP-A 2014-001259, paragraphs [0088]-[0092], the compounds described in JP-A 2012-041320, paragraphs [0015]-[0017], and the compounds described in JP-A 2012-106986, paragraphs [0015]-[0029]. The PAGs capable of generating partially fluorinated sulfonic acids described in these patent documents are advantageously used in ArF lithography because the generated acid has an appropriate strength and diffusion length.

The resist composition contains a solvent as component (C). Suitable solvents include those described in JP-A 2008-111103, paragraphs [0144]-[0145], for example, ketones such as cyclohexanone and methyl-2-n-pentyl ketone; alcohols such as 3-methoxybutanol, 3-methyl-3-methoxybutanol, 1-methoxy-2-propanol, and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate (PGMEA), propylene glycol monoethyl ether acetate, methyl lactate, ethyl pyruvate, butyl acetate, methyl 3-methoxypropionate, ethyl 3-ethoxypropionate, t-butyl acetate, tert-butyl propionate, and propylene glycol mono-t-butyl ether acetate; lactones such as γ-butyrolactone; alcohols such as diacetone alcohol, which may be used alone or in admixture. Where an acid labile group of acetal form is used, a high-boiling alcohol solvent such as diethylene glycol, propylene glycol, glycerol, 1,4-butanediol or 1,3-butanediol may be added for accelerating deprotection reaction of acetal.

An appropriate amount of the solvent used is 100 to 10,000 parts, more preferably 300 to 8,000 parts by weight per 100 parts by weight of the base resin.

In the resist composition, (D) a second polymer different from the polymer (A) may be included, if desired. The second polymer is defined as comprising recurring units of at least one type selected from recurring units having the following formulae (D-1) to (D-5).

(D-1)

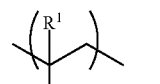

(D-2)

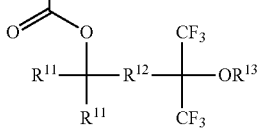

(D-3)

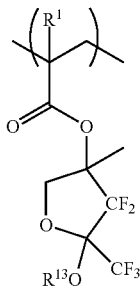

(D-4)

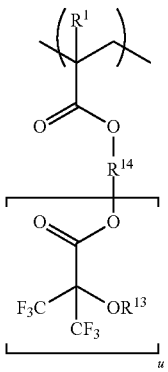

(D-5)

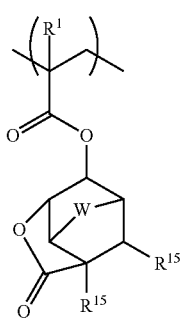

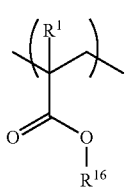

Herein $R^1$ and W are as defined above. $R^{11}$ is each independently hydrogen or a $C_1$-$C_{10}$ straight, branched or cyclic monovalent hydrocarbon group. $R^{12}$ is a single bond or a $C_1$-$C_5$ straight or branched divalent hydrocarbon group. $R^{13}$ is each independently hydrogen, a $C_1$-$C_{15}$ straight, branched or cyclic monovalent hydrocarbon or monovalent fluorinated hydrocarbon group, or an acid labile group, the monovalent hydrocarbon or fluorinated hydrocarbon group represented by $R^{13}$ may have an ether bond (—O—) or carbonyl moiety (—C(=O)—) intervening in a carbon-carbon bond. $R^{14}$ is a $C_1$-$C_{20}$ straight, branched or cyclic (u+1)-valent hydrocarbon or fluorinated hydrocarbon group, and u is an integer of 1 to 3. $R^{15}$ is each independently hydrogen or a group of the formula (ii):

$$—C(=O)—O—R^{17} \quad \text{(ii)}$$

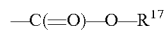

wherein $R^{17}$ is a $C_1$-$C_{20}$ straight, branched or cyclic monovalent fluorinated hydrocarbon group. $R^{16}$ is a $C_1$-$C_{15}$ straight, branched or cyclic monovalent hydrocarbon or monovalent fluorinated hydrocarbon group which may have an ether bond (—O—) or carbonyl moiety (—C(=O)—) intervening in a carbon-carbon bond.

Examples of the monovalent hydrocarbon group $R^{11}$ include methyl, ethyl, n-propyl, isopropyl, cyclopropyl, n-butyl, isobutyl, sec-butyl, t-butyl, cyclobutyl, n-pentyl, cyclopentyl, n-hexyl, cyclohexyl, n-heptyl, n-octyl, n-nonyl, n-decyl, adamantyl and norbornyl. Inter alia, $C_1$-$C_6$ straight, branched or cyclic hydrocarbon groups are preferred.

Examples of the divalent organic group $R^{12}$ include methylene, ethylene, propylene, butylene and pentylene.

Suitable monovalent hydrocarbon groups $R^{13}$ or $R^{16}$ include alkyl, alkenyl, and alkynyl groups. Inter alia, alkyl groups are preferred, examples of which include those exemplified above for $R^{11}$ and n-undecyl, n-dodecyl, tridecyl, tetradecyl, and pentadecyl. Suitable monovalent fluorinated hydrocarbon groups $R^{13}$ or $R^{16}$ are the foregoing monovalent hydrocarbon groups in which at least one hydrogen atom (one or more or even all hydrogen atoms) is substituted by fluorine. These monovalent hydrocarbon or fluorinated hydrocarbon groups may have an ether bond (—O—) or carbonyl moiety (—C(=O)—) intervening in a carbon-carbon bond.

Examples of the acid labile group $R^{13}$ include groups of the above formulae (L1) to (L9), $C_4$-$C_{20}$, preferably $C_4$-$C_{15}$ tertiary alkyl groups, trialkylsilyl groups in which each alkyl moiety has 1 to 6 carbon atoms, and $C_4$-$C_{20}$ oxoalkyl groups, as defined and illustrated above.

Suitable (u+1)-valent hydrocarbon or fluorinated hydrocarbon groups represented by $R^{14}$ include the above-mentioned hydrocarbon or fluorinated hydrocarbon groups, with the number "u" of hydrogen atoms being eliminated.

Suitable fluorinated hydrocarbon groups $R^{17}$ are the foregoing monovalent hydrocarbon groups in which at least one hydrogen atom (one or more or even all hydrogen atoms) is substituted by fluorine. Suitable examples include trifluoromethyl, 2,2,2-trifluoroethyl, 3,3,3-trifluoro-1-propyl, 3,3,3-trifluoro-2-propyl, 2,2,3,3-tetrafluoropropyl, 1,1,1,3,3,3-hexafluoroisopropyl, 2,2,3,3,4,4,4-heptafluorobutyl, 2,2,3,3,4,4,5,5-octafluoropentyl, 2,2,3,3,4,4,5,5,6,6,7,7-dodecafluoroheptyl, 2-(perfluorobutyl)ethyl, 2-(perfluorohexyl)ethyl, and 2-(perfluorodecyl)ethyl.

Examples of the recurring units having formulae (D-1) to (D-5) are shown below, but not limited thereto. Herein $R^1$ is as defined above.

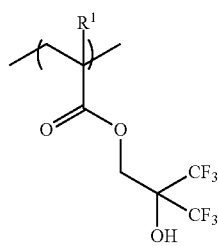 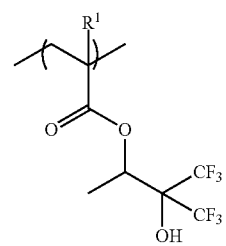

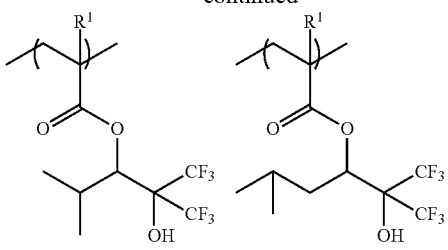
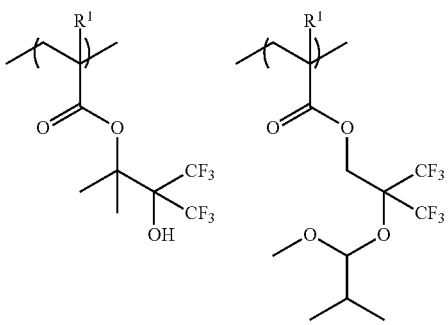
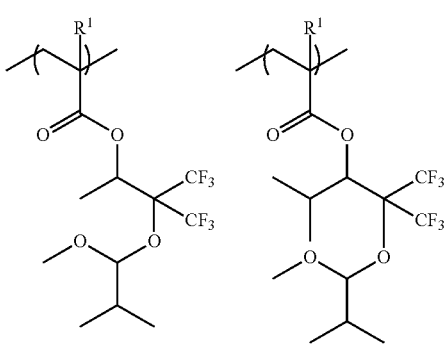
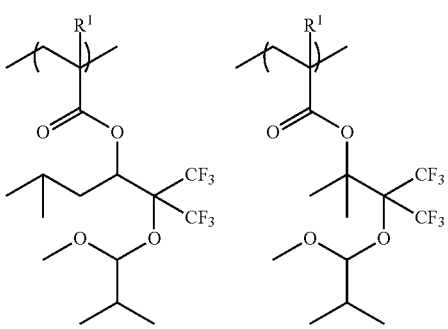
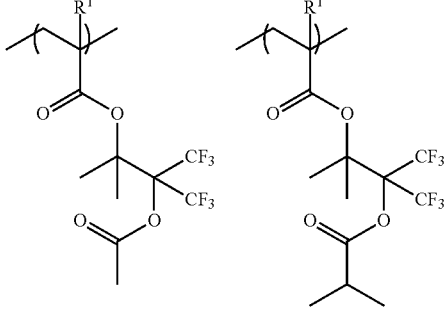
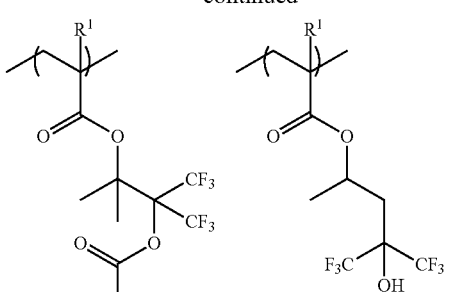
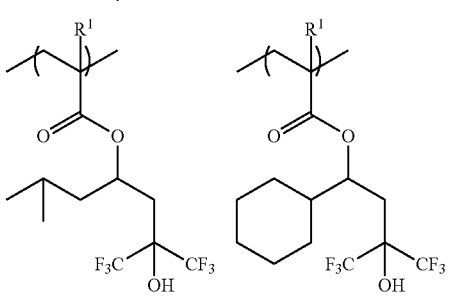
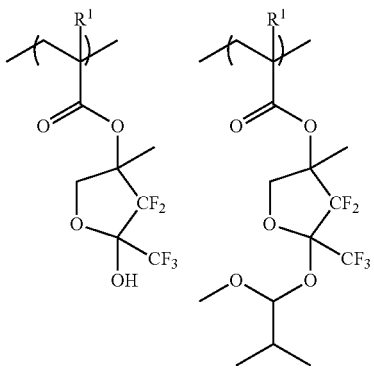
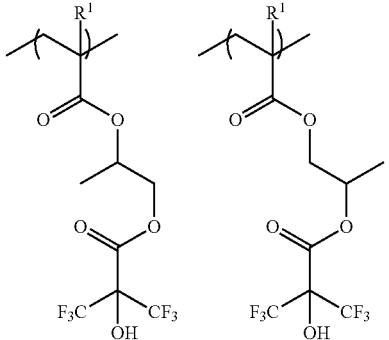
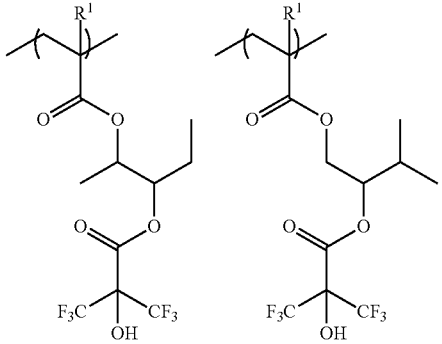

137
-continued
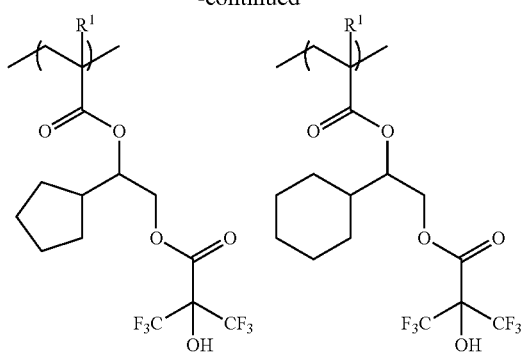
138
-continued
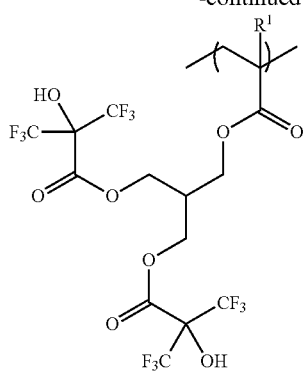
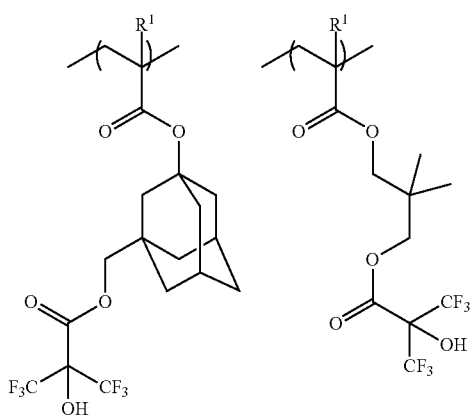
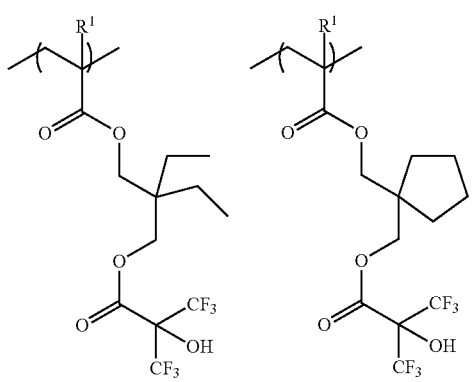
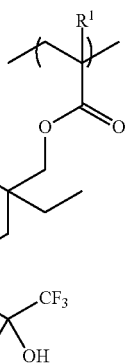
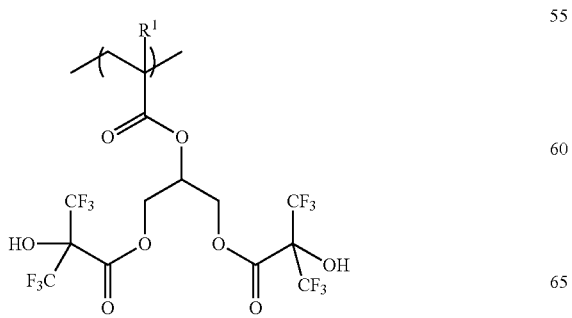
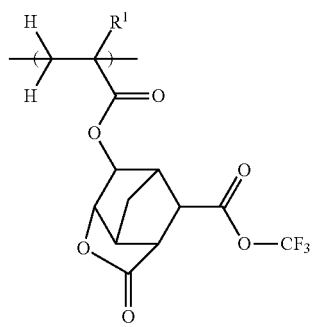

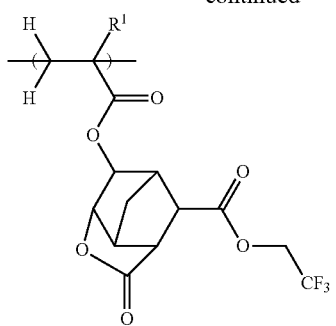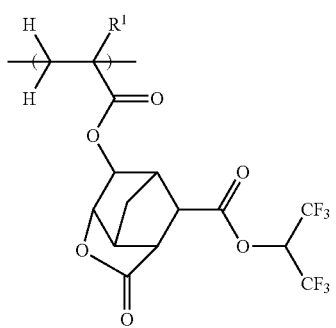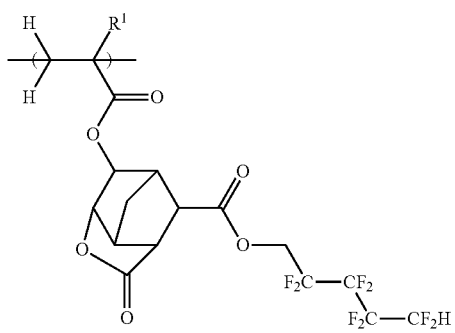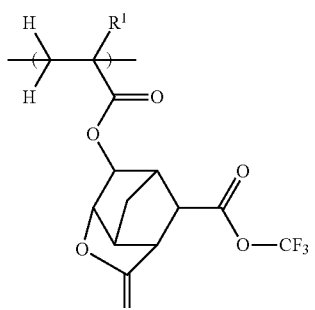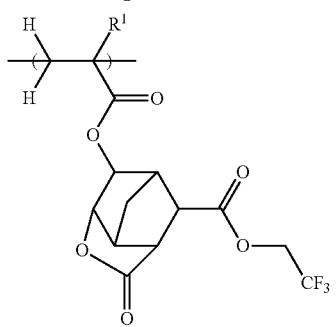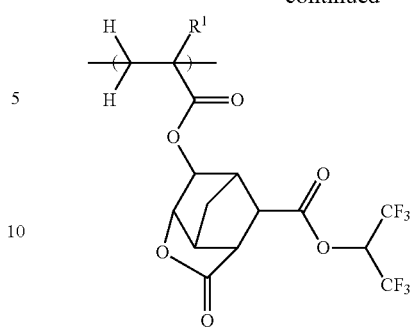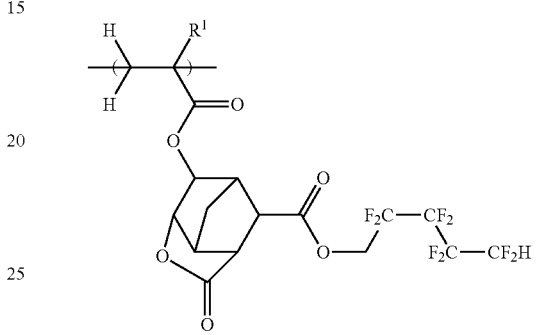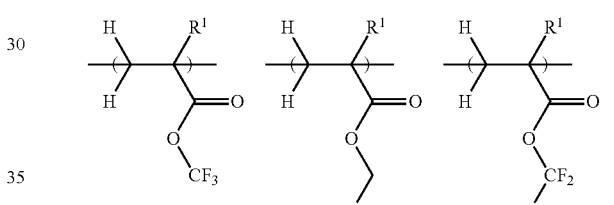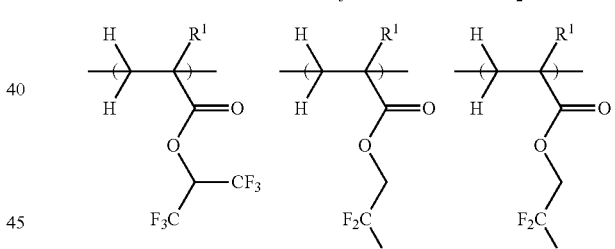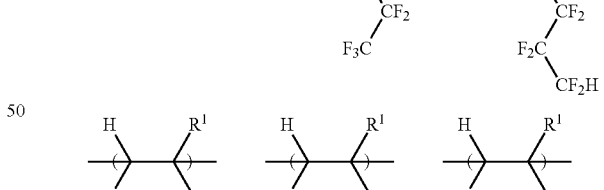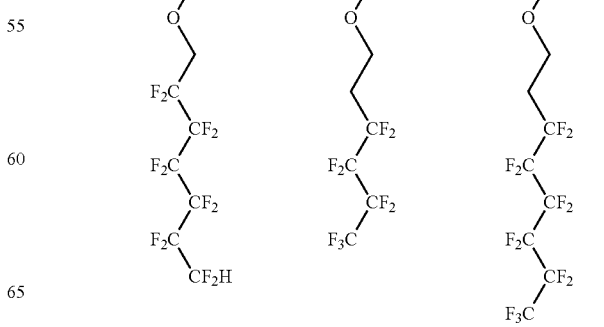

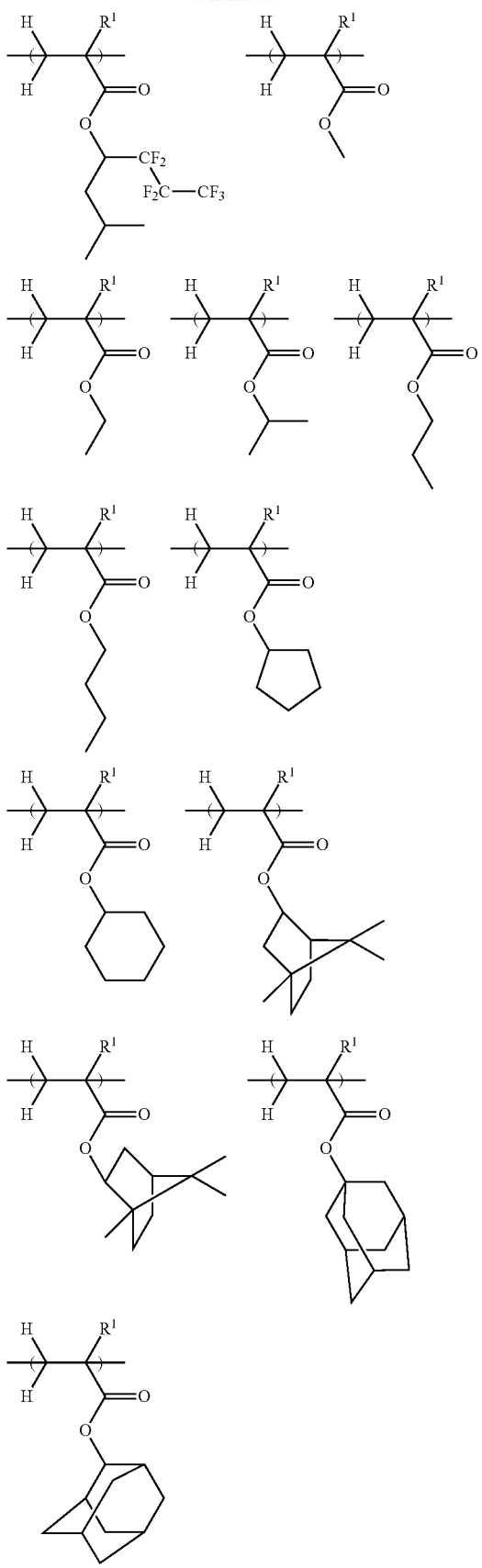

The second polymer (D) preferably has a Mw of 1,000 to 500,000, more preferably 3,000 to 100,000 and a dispersity Mw/Mn of 1.0 to 2.0, more preferably 1.0 to 1.6.

In addition to the recurring units having formulae (D-1) to (D-5), the second polymer (D) may further comprise additional recurring units. Such additional recurring units include those derived from methacrylic acid and α-trifluoromethylacrylic acid derivatives. In the second polymer (D), the recurring units having formulae (D-1) to (D-5) preferably account for at least 20 mol %, more preferably at least 60 mol %, and most preferably 100 mol % of overall recurring units.

The second polymer (D) may be synthesized by any desired methods, for example, by dissolving one or more unsaturated bond-bearing monomers corresponding to the recurring unit having formula (D-1) to (D-5) and optionally additional recurring units in an organic solvent, adding a radical initiator thereto, and effecting heat polymerization. Examples of the organic solvent which can be used for polymerization include toluene, benzene, tetrahydrofuran, diethyl ether, and dioxane. Examples of the polymerization initiator used herein include 2,2'-azobisisobutyronitrile (AIBN), 2,2'-azobis(2,4-dimethylvaleronitrile), dimethyl 2,2-azobis(2-methylpropionate), benzoyl peroxide, and lauroyl peroxide. Preferably the reaction temperature is in a range of 50 to 100° C. and the reaction time is 4 to 24 hours. The acid labile group that has been incorporated in the monomer may be kept as such, or polymerization may be followed by protection or partial protection.

During the polymer synthesis, any known chain transfer agent such as dodecyl mercaptan or 2-mercaptoethanol may be added for molecular weight control purpose. The amount of chain transfer agent added is preferably 0.01 to 10 mol % based on the total moles of monomers.

When the second polymer (D) is added to the resist composition, a (total) amount of the second polymer is preferably 0.1 to 50 parts, more preferably 0.5 to 10 parts by weight per 100 parts by weight of the base resin. At least 0.1 part by weight of the second polymer is effective for improving the receding contact angle of resist film surface with water whereas up to 50 parts by weight of the second polymer is effective for keeping low the dissolution rate of resist film surface in the developer and fully maintaining the height of a fine size pattern formed therefrom.

The resist composition may further comprise an amine compound as a quencher if necessary. As used herein, the quencher is a compound capable of suppressing the diffusion rate when the acid generated by the PAG diffuses through the resist film. Examples of the quencher include primary, secondary, and tertiary amine compounds as described in JP-A 2008-111103 (U.S. Pat. No. 7,537,880), paragraphs [0146]-[0164], specifically amine compounds having a hydroxyl, ether, ester, lactone, cyano or sulfonic ester group, and primary or secondary amine compounds protected in carbamate form as described in JP 3790649. The protected amine compounds are effective particularly when the resist composition contains a base labile component.

The quencher may be used alone or in admixture. An appropriate amount of the quencher is 0.001 to 12 parts, more preferably 0.01 to 8 parts by weight per 100 parts by weight of the base resin. The inclusion of quencher in this range facilitates adjustment of resist sensitivity and holds down the rate of acid diffusion within the resist film, resulting in better resolution. In addition, it suppresses changes in sensitivity following exposure and reduces substrate and environment dependence, as well as improving the exposure latitude and the pattern profile. The inclusion of quencher is also effective for improving adhesion to the substrate.

The resist composition may further comprise a surfactant which is insoluble or substantially insoluble in water and soluble in alkaline developer, and/or a surfactant which is insoluble or substantially insoluble in water and alkaline developer (hydrophobic resin). For the surfactant which can be added to the resist composition, reference should be made to those compounds defined as component (S) in JP-A 2010-215608 and JP-A 2011-016746.

While many examples of the surfactant which is insoluble or substantially insoluble in water and alkaline developer are described in these patent documents, preferred examples are FC-4430 (3M), Surflon® S-381 (AGC Seimi Chemical Co., Ltd.), Surfynol® E1004 (Air Products and Chemicals, Inc.), KH-20 and KH-30 (Asahi Glass Co., Ltd.), which may be used alone or in admixture. Partially fluorinated oxetane ring-opened polymers having the structural formula (surf-1) are also useful.

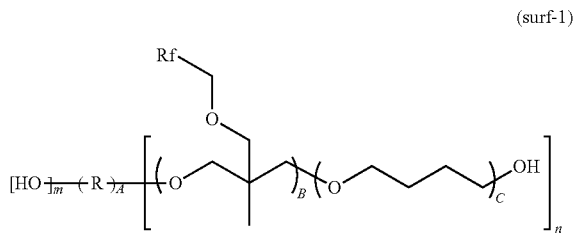

(surf-1)

It is provided herein that R, Rf, A, B, C, m, and n are applied to only formula (surf-1), independent of their descriptions other than for the surfactant. R is a di- to tetra-valent $C_2$-$C_5$ aliphatic group. Exemplary divalent groups include ethylene, 1,4-butylene, 1,2-propylene, 2,2-dimethyl-1,3-propylene and 1,5-pentylene. Exemplary tri- and tetra-valent groups are shown below.

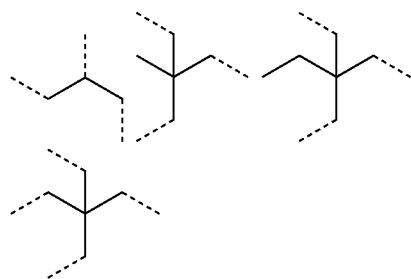

Herein the broken line denotes a valence bond. These formulae are partial structures derived from glycerol, trimethylol ethane, trimethylol propane, and pentaerythritol, respectively. Of these, 1,4-butylene and 2,2-dimethyl-1,3-propylene are preferably used.

Rf is trifluoromethyl or pentafluoroethyl, and preferably trifluoromethyl. The letter m is an integer of 0 to 3, n is an integer of 1 to 4, and the sum of m and n, which represents the valence of R, is an integer of 2 to 4. A is equal to 1, B is an integer of 2 to 25, and C is an integer of 0 to 10. Preferably, B is an integer of 4 to 20, and C is 0 or 1. Note that the above structural formula does not prescribe the arrangement of respective constituent units while they may be arranged either blockwise or randomly. For the preparation of surfactants in the form of partially fluorinated oxetane ring-opened polymers, reference should be made to U.S. Pat. No. 5,650,483, for example.

Process

A further embodiment of the invention is a pattern forming process using the resist composition defined above. Pattern formation using the resist composition may be performed by well-known lithography processes. The process generally involves coating, prebaking, exposure, PEB, and development. If necessary, any additional steps may be added.

First the resist composition is applied onto a substrate for integrated circuitry fabrication (e.g., Si, $SiO_2$, SiN, SiON, TiN, WSi, BPSG, SOG, organic antireflective film, etc.) or a substrate for mask circuitry fabrication (e.g., Cr, CrO, CrON, MoSi, etc.) by a suitable coating technique such as spin coating. The coating is prebaked on a hot plate at a temperature of 60 to 150° C. for 1 to 10 minutes, preferably 80 to 140° C. for 1 to 5 minutes. The resulting resist film is generally 0.05 to 2 μm thick.

Through a photomask having a desired pattern disposed over the substrate, the resist film is then exposed to high-energy radiation such as KrF excimer laser, ArF excimer laser or EUV in an exposure dose preferably in the range of 1 to 200 mJ/cm², more preferably 10 to 100 mJ/cm². Alternatively, pattern formation may be performed by writing with EB directly in a dose of 0.1 to 100 μC/cm², more preferably 0.5 to 50 μC/cm². Light exposure may be done by a conventional lithography process or in some cases, by an immersion lithography process of providing liquid impregnation, typically water, between the projection lens and the resist film. In the case of immersion lithography, a protective film which is insoluble in water may be used. The resist film is then baked (PEB) on a hot plate at 60 to 150° C. for 1 to 5 minutes, and preferably at 80 to 140° C. for 1 to 3 minutes. Finally, development is carried out using as the developer an aqueous alkaline solution, such as a 0.1 to 5 wt %, preferably 2 to 3 wt %, aqueous solution of tetramethylammonium hydroxide (TMAH) or an organic solvent such as butyl acetate. This may be done by a conventional method such as dip, puddle, or spray development for a period of preferably 0.1 to 3 minutes, more preferably 0.5 to 2 minutes. In this way the desired pattern is formed on the substrate.

While the water-insoluble protective film which is used in the immersion lithography serves to prevent any components from being leached out of the resist film and to improve water slippage at the film surface, it is generally divided into two types. The first type is an organic solvent-strippable protective film which must be stripped, prior to alkaline development, with an organic solvent in which the resist film is not dissolvable. The second type is an alkali-soluble protective film which is soluble in an alkaline developer so that it can be removed simultaneously with the removal of solubilized regions of the resist film. The protective film of the second type is preferably of a material comprising a polymer having a 1,1,1,3,3,3-hexafluoro-2-propanol residue (which is insoluble in water and soluble in an alkaline developer) as a base in an alcohol solvent of at least 4 carbon atoms, an ether solvent of 8 to 12 carbon atoms or a mixture thereof. Alternatively, the aforementioned surfactant which is insoluble in water and soluble in an alkaline developer may be dissolved in an alcohol solvent of at least 4 carbon atoms, an ether solvent of 8 to 12 carbon atoms or a mixture thereof to form a material from which the protective film of the second type is formed.

Any desired step may be added to the pattern forming process. For example, after a photoresist film is formed, a step of rinsing with pure water (post-soaking) may be introduced to extract the acid generator or the like from the film surface or wash away particles. After exposure, a step of rinsing (post-soaking) may be introduced to remove any water remaining on the film after exposure.

In the pattern forming process, an alkaline aqueous solution, typically an aqueous solution of 0.1 to 5 wt %, more typically 2 to 3 wt % of tetramethylammonium hydroxide (TMAH) is often used as the developer. An organic solvent may also be used. In the negative tone development technique, the unexposed region of resist film is developed and dissolved in the organic solvent.

In the organic solvent development, the organic solvent used as the developer is preferably selected from 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, pentyl acetate, isopentyl acetate, butenyl acetate, phenyl acetate, propyl formate, butyl formate, isobutyl formate, pentyl formate, isopentyl formate, methyl valerate, methyl pentenoate, methyl crotonate, ethyl crotonate, methyl lactate, ethyl lactate, propyl lactate, butyl lactate, isobutyl lactate, pentyl lactate, isopentyl lactate, methyl 2-hydroxyisobutyrate, ethyl 2-hydroxyisobutyrate, methyl benzoate, ethyl benzoate, benzyl acetate, methyl phenylacetate, benzyl formate, phenylethyl formate, methyl 3-phenylpropionate, benzyl propionate, ethyl phenylacetate, and 2-phenylethyl acetate. These organic solvents may be used alone or in admixture of two or more.

EXAMPLE

Examples and Comparative Examples are given below by way of illustration and not by way of limitation. The abbreviation "pbw" is parts by weight, THF stands for tetrahydrofuran, and DMF for dimethylformamide. For all polymers, Mw and Mn are determined versus polystyrene standards by GPC using THF solvent, and dispersity Mw/Mn is computed therefrom.

Example 1

Synthesis of Monomers

Example 1-1

Synthesis of Monomer 1

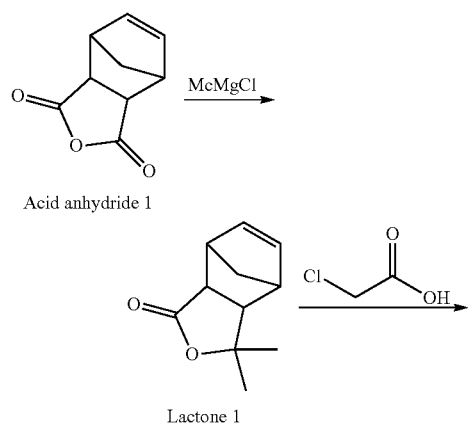

Acid anhydride 1

Lactone 1

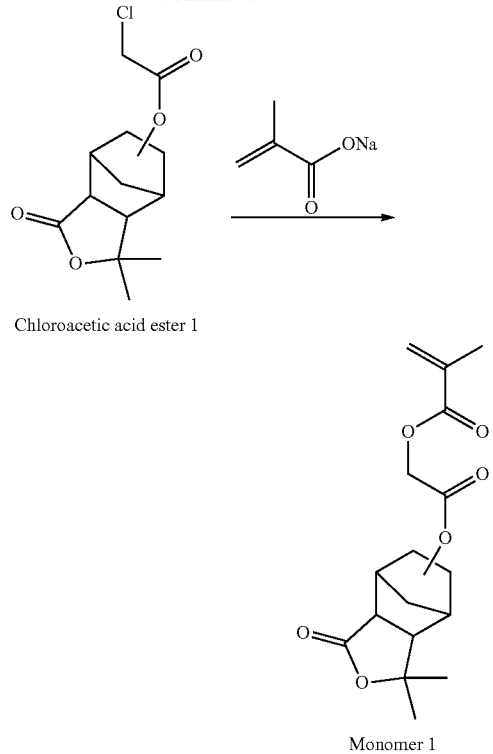

Chloroacetic acid ester 1

Monomer 1

Example 1-1-1

Synthesis of Lactone 1

In nitrogen atmosphere, a solution of 164 g of Acid anhydride 1 in 500 g of THF was added dropwise to 1,500 mL of a THF solution of 1.0 mol/L methylmagnesium chloride below 30° C. The contents were stirred at the temperature for 5 hours, after which 980 g of 10 wt % hydrochloric acid was added dropwise to quench the reaction. This was followed by ordinary aqueous workup. The organic layer was concentrated, yielding 175 g of crude Lactone 1.

Example 1-1-2

Synthesis of Chloroacetic Acid Ester 1

A solution of 175 g of crude Lactone 1 (Example 1-1-1) and 132 g of chloroacetic acid was heated at 100° C., to which 15.0 g of trifluoromethanesulfonic acid was added dropwise over 1 hour. The solution was stirred at the temperature for 30 minutes, after which 200 g of toluene and 1,000 g of 10 wt % sodium hydrogencarbonate aqueous solution were added dropwise to quench the reaction. This was followed by ordinary aqueous workup, purification by silica gel chromatography, and recrystallization from ethyl acetate and n-hexane. There was obtained Chloroacetic acid ester 1 (122 g, two-step yield 45%). The product was analyzed by infrared (IR) spectroscopy and nuclear magnetic resonance ($^1$H-NMR) spectroscopy, with the results shown below.

IR (D-ATR): ν=2985, 2966, 2888, 1749, 1406, 1397, 1384, 1371, 1311, 1276, 1201, 1183, 1160, 1149, 1127, 1046, 990, 968 cm$^{-1}$ $^1$H-NMR (600 MHz in DMSO-$d_6$, for only main isomer): δ=4.61 (1H, d), 4.33 (2H, s), 2.87 (1H, d), 2.47-2.52 (1H, m), 2.45 (1H, s), 2.05 (1H, d), 1.83-1.88 (1H, m), 1.41-1.48 (2H, m), 1.31 (6H, d), 1.15 (1H, d) ppm

Example 1-1-3

Synthesis of Monomer 1

A mixture of 100 g of Chloroacetic acid ester 1 (Example 1-1-2) and 150 g of DMF was added dropwise to a mixture of 45.6 g of sodium methacrylate, 3.3 g of sodium iodide, and 200 g of DMF below 30° C. The contents were stirred at the temperature for 8 hours. To the reaction solution, 400 mL of water below 30° C. was added, followed by ordinary aqueous workup. On recrystallization from ethyl acetate and n-hexane, there was obtained Monomer 1 (98.1 g, yield 83%).

IR (D-ATR): ν=2977, 2884, 1751, 1731, 1635, 1424, 1388, 1362, 1299, 1276, 1261, 1227, 1185, 1149, 1126, 1066, 1053, 985, 970 cm$^{-1}$ $^1$H-NMR (600 MHz in DMSO-d$_6$, for only main isomer): δ=6.10 (1H, s), 5.78 (1H, m), 4.69 (2H, s), 4.61 (1H, d), 2.86 (1H, d), 2.47-2.51 (1H, m), 2.42 (1H, s), 2.04 (1H, d), 1.89 (3H, s), 1.82-1.87 (1H, m), 1.36-1.44 (2H, m), 1.31 (6H, d), 1.14 (1H, d) ppm

Example 1-2

Synthesis of Chloroacetic Acid Ester 1 by Another Route

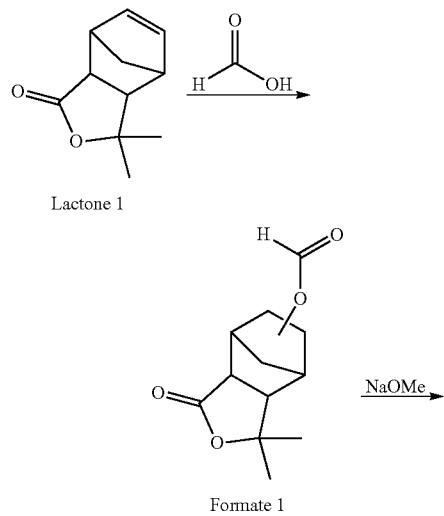

Example 1-2-1

Synthesis of Formate 1

A solution of 108 g of crude Lactone 1 (Example 1-1-1) and 168 g of formic acid was heated at 90° C., to which 2.9 g of methanesulfonic acid was added dropwise. The contents were stirred at the temperature for 20 hours. The reaction solution was concentrated by distilling off the excess formic acid. The crude product was combined with 500 g of ethyl acetate and 100 g of water, followed by ordinary aqueous workup. The organic layer was concentrated. The concentrate was purified by vacuum distillation, obtaining Formate 1 (71 g, two-step yield 51%).

boiling point: 116-120° C./35 Pa

Example 1-2-2

Synthesis of Hydroxy-Lactone 1

A reactor equipped with a distillation head was charged with 53 g of Formate 1 (Example 1-2-1), 53 g of methanol, and 1.3 g of sodium methoxide. With stirring, the mixture was heated at 70° C. Methyl formate which formed in the course of reaction was removed by distillation. Stirring and heating under reflux was continued for 3 hours, after which the excess of methanol was distilled off. To the reaction solution, 30 g of 5 wt % hydrochloric acid was added to quench the reaction. This was followed by ordinary aqueous workup and recrystallization from ethyl acetate and n-hexane, obtaining Hydroxy-lactone 1 (38 g, yield 82%).

IR (D-ATR): ν=3471, 2976, 2941, 2892, 1726, 1373, 1337, 1292, 1271, 1256, 1184, 1141, 1125, 1073, 989, 972 cm$^{-1}$ $^1$H-NMR (600 MHz in DMSO-d$_6$, for only main isomer): δ=4.64 (1H, d), 3.53 (1H, m), 2.72 (1H, d), 2.38 (1H, d), 2.17 (1H, s), 1.82 (1H, d), 1.59-1.65 (1H, m), 1.53 (1H, d), 1.30 (6H, d), 1.17-1.22 (1H, m), 1.00 (1H, d) ppm

Example 1-2-3

Synthesis of Chloroacetic Acid Ester 1

In 25 g of THF, 6.3 g of Hydroxy-lactone 1 (Example 1-2-2) and 4.3 g of 2-chloroacetic acid chloride were dissolved. To the solution below 20° C., 3.0 g of pyridine was added dropwise. The solution was stirred at room temperature for 1 hour, after which 6.9 g of 7 wt % sodium hydrogencarbonate aqueous solution were added. This was followed by ordinary aqueous workup and purification from ethyl acetate and n-hexane. There was obtained Chloroacetic acid ester 1 (7.5 g, yield 86%). The physical data of this product were fully identical with those of Example 1-1-2.

Example 1-3

Synthesis of Monomer 1 by Another Route

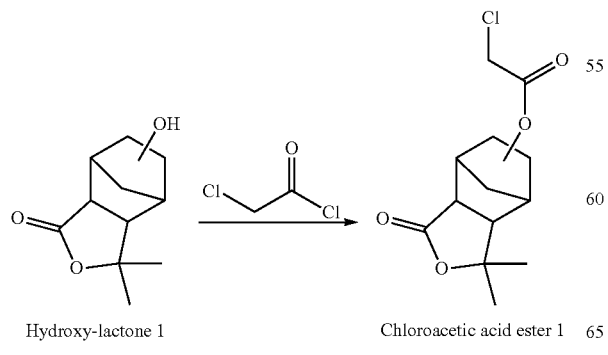

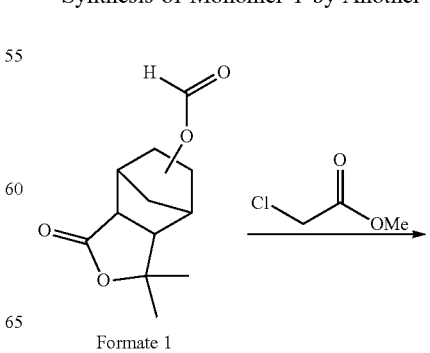

149
-continued

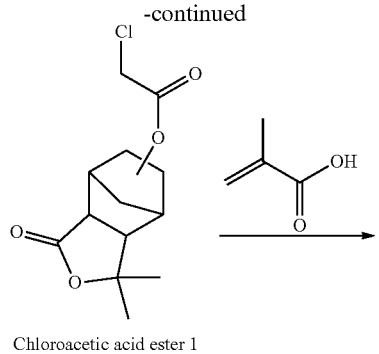

Chloroacetic acid ester 1

Monomer 1

Example 1-3-1

Synthesis of Chloroacetic Acid Ester 1 by Third Route

A reactor equipped with a distillation head was charged with 22 g of Formate 1 (Example 1-2-1), 22 g of methyl chloroacetate, and 0.5 g of titanium(IV) methoxide. With stirring, the mixture was heated at 100° C. Methyl formate which formed in the course of reaction was removed by distillation. Stirring and heating under reflux was continued for 20 hours. To the reaction solution, 20 g of 5 wt % sodium hydrogencarbonate aqueous solution was added to quench the reaction. This was followed by ordinary aqueous workup and recrystallization from ethyl acetate and n-hexane, obtaining Chloroacetic acid ester 1 (20 g, yield 72%). The physical data of this product were fully identical with those of Example 1-1-2.

Example 1-3-2

Synthesis of Monomer 1

To a mixture of 27 g of Chloroacetic acid ester 1 (Example 1-3-1), 1.5 g of sodium iodide, 12 g of methacrylic acid and 100 g of DMF below 30° C., 11 g of triethylamine was added dropwise. The contents were stirred at the temperature for 8 hours. To the reaction solution, 150 mL of water below 30° C. was added, followed by ordinary aqueous workup. On recrystallization from ethyl acetate and n-hexane, there was obtained Monomer 1 (26.4 g, yield 82%). The physical data of this product were fully identical with those of Example 1-1-3.

150

Example 1-4

Synthesis of Monomer 2

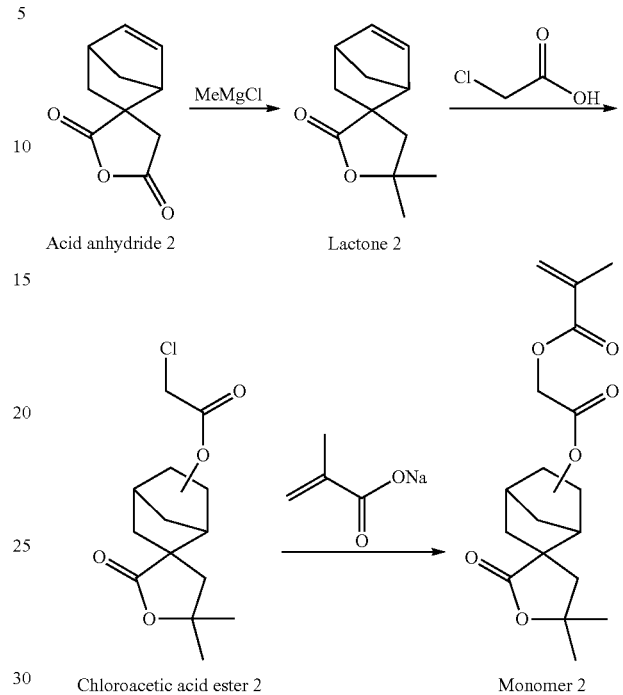

Acid anhydride 2    Lactone 2

Chloroacetic acid ester 2    Monomer 2

Example 1-4-1

Synthesis of Lactone 2

In nitrogen atmosphere, a solution of 114 g of Acid anhydride 2 in 300 g of THF was added dropwise to 1,410 mL of a THF solution of 1.0 mol/L methylmagnesium chloride below 30° C. The contents were stirred at the temperature for 5 hours, after which 566 g of 10 wt % hydrochloric acid was added dropwise to quench the reaction. This was followed by ordinary aqueous workup. The organic layer was concentrated and purified by vacuum distillation, obtaining Lactone 2 (102 g, yield 83%).
boiling point: 76-78° C./12 Pa

Example 1-4-2

Synthesis of Chloroacetic Acid Ester 2

By repeating the same procedure as in Example 1-1-2 aside from using Lactone 2 instead of Lactone 1, there was obtained Chloroacetic acid ester 2 (yield 54%).

$^1$H-NMR (600 MHz in DMSO-$d_6$, for only main isomer): δ=4.69 (1H, d), 4.33 (2H, s), 2.32 (2H, m), 2.16 (1H, d), 2.08 (1H, s), 1.93-2.03 (2H, m), 1.59 (1H, d), 1.46 (1H, d), 1.32-1.39 (6H, m), 1.30 (2H, s) ppm

Example 1-4-3

Synthesis of Monomer 2

By repeating the same procedure as in Example 1-1-3 aside from using Chloroacetic acid ester 2 instead of Chloroacetic acid ester 1, there was obtained Monomer 2 (yield 91%).

IR (D-ATR): ν=2973, 2872, 1749, 1723, 1636, 1447, 1421, 1389, 1376, 1298, 1274, 1216, 1156, 1110, 1061, 1044, 977, 937 cm$^{-1}$ $^1$H-NMR (600 MHz in DMSO-$d_6$, for only main isomer): δ=6.09 (1H, s), 5.77 (1H, m), 2.26-2.33 (2H, m), 2.15 (1H, d), 2.08 (1H, d), 1.93-2.02 (2H, m), 1.89 (3H, s), 1.59 (1H, d), 1.42 (1H, d), 1.32-1.38 (6H, m), 1.30 (2H, s) ppm Example 1-5

Synthesis of Monomer 3

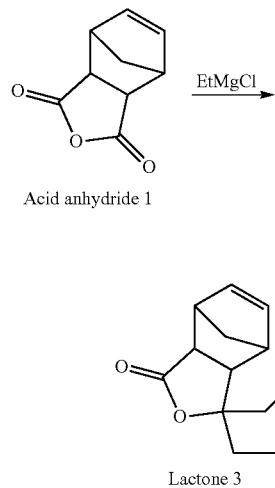

Example 1-6

Synthesis of Monomer 4

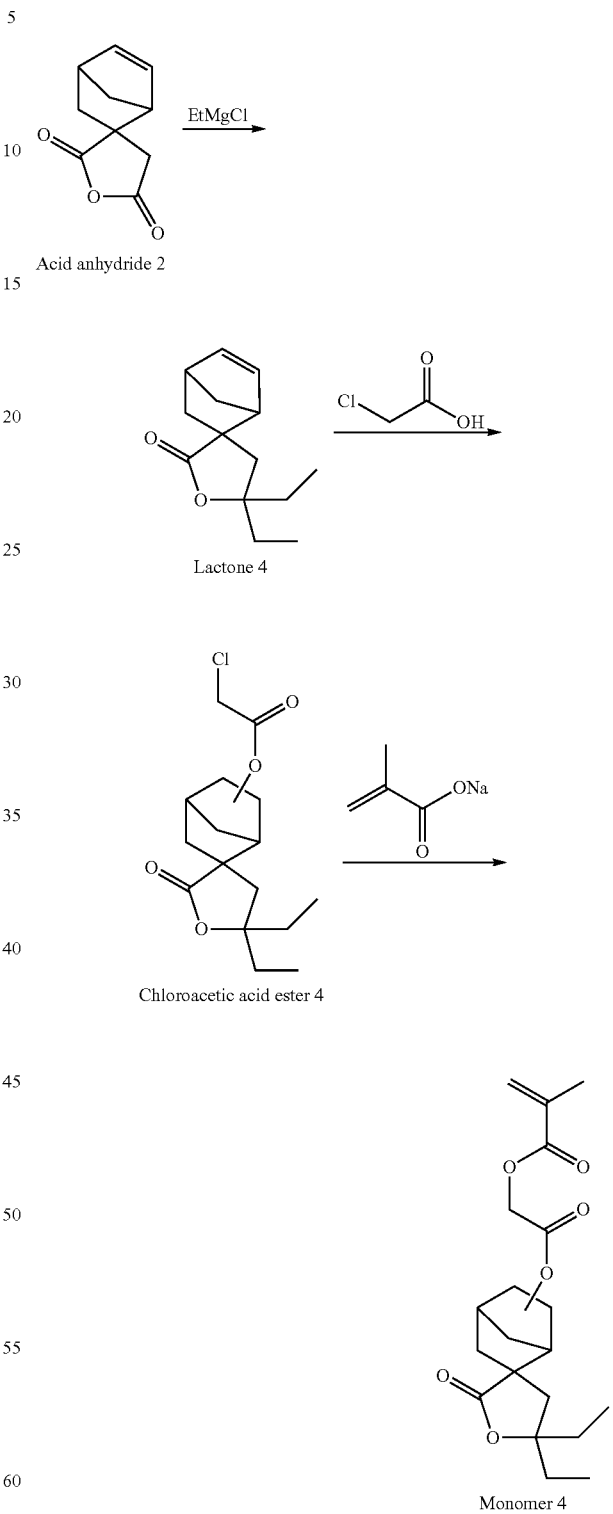

By repeating the same procedures as in Examples 1-1-1 to 1-1-3 aside from using ethylmagnesium chloride instead of methylmagnesium chloride, there was obtained Monomer 3 (overall yield 35%).

By repeating the same procedures as in Examples 1-4-1 to 1-4-3 aside from using ethylmagnesium chloride instead of methylmagnesium chloride, there was obtained Monomer 4 (overall yield 30%).

Example 1-7

Synthesis of Monomer 5

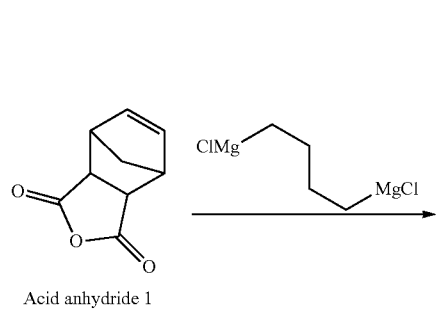

Acid anhydride 1

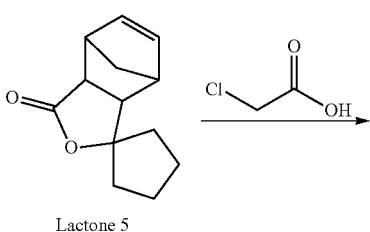

Lactone 5

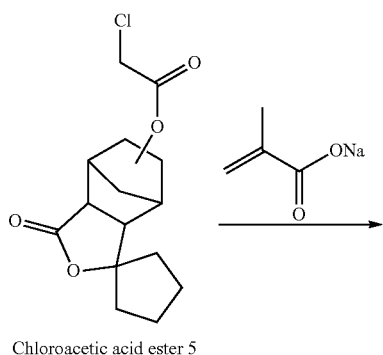

Chloroacetic acid ester 5

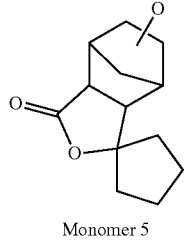

Monomer 5

By repeating the same procedures as in Examples 1-1-1 to 1-1-3 aside from using 1,4-dichlorobutane magnesium instead of methylmagnesium chloride, there was obtained Monomer 5 (overall yield 29%).

Example 1-8

Synthesis of Monomer 6

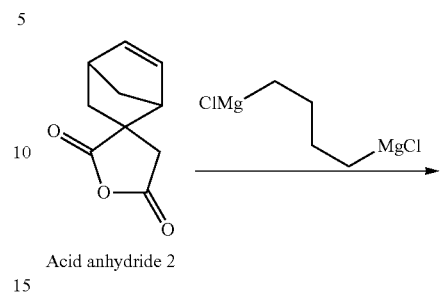

Acid anhydride 2

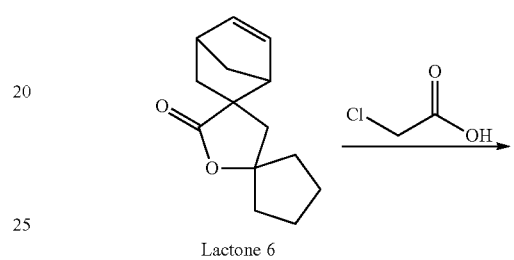

Lactone 6

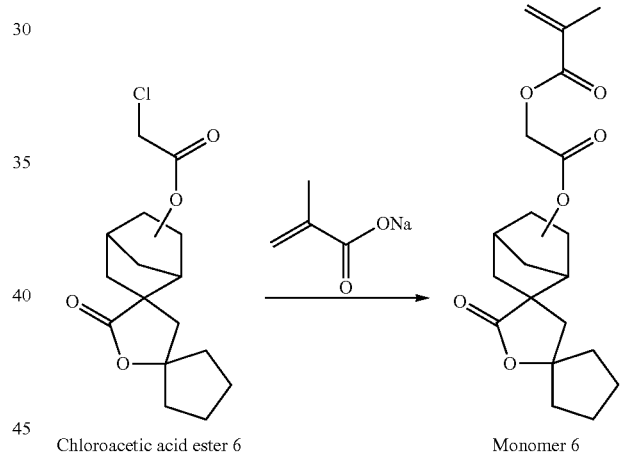

Chloroacetic acid ester 6    Monomer 6

By repeating the same procedures as in Examples 1-4-1 to 1-4-3 aside from using 1,4-dichlorobutane magnesium instead of methylmagnesium chloride, there was obtained Monomer 6 (overall yield 25%).

Example 1-9

Synthesis of Monomer 7

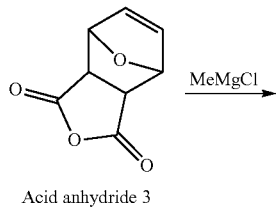

Acid anhydride 3

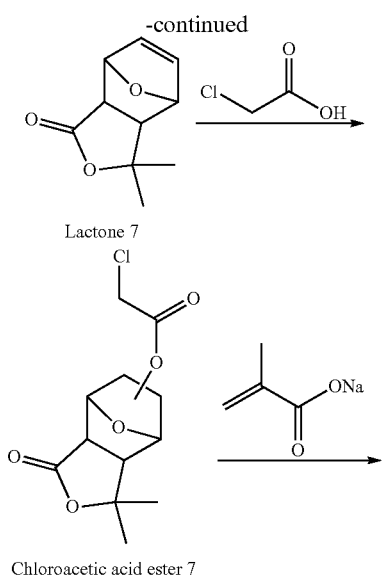

Lactone 7

Chloroacetic acid ester 7

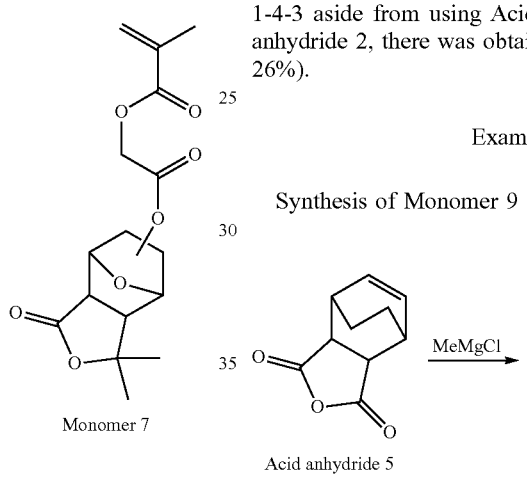

Monomer 7

By repeating the same procedures as in Examples 1-1-1 to 1-1-3 aside from using Acid anhydride 3 instead of Acid anhydride 1, there was obtained Monomer 7 (overall yield 34%).

Example 1-10

Synthesis of Monomer 8

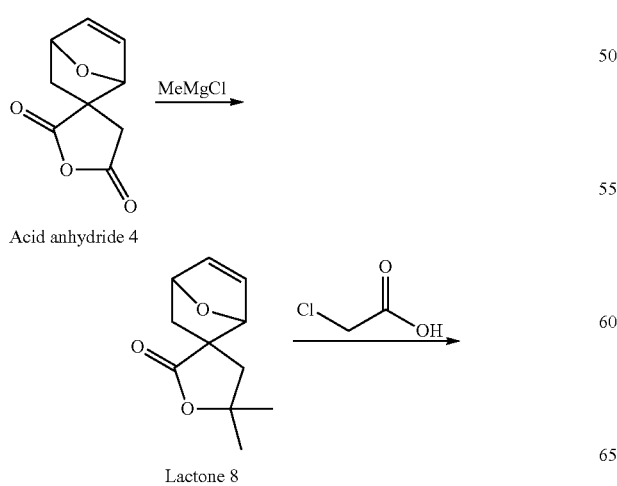

Acid anhydride 4

Lactone 8

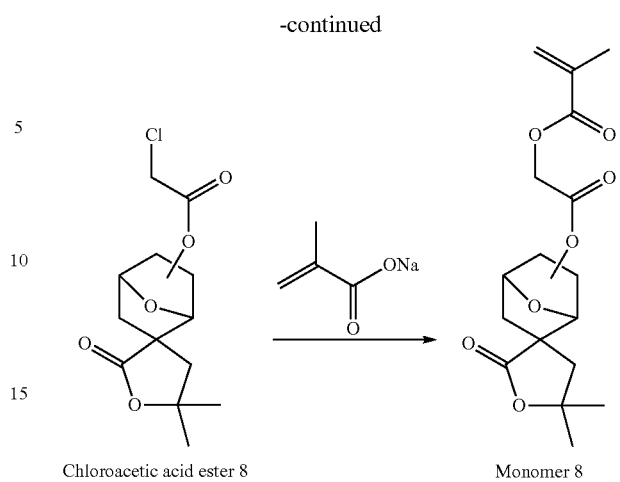

Chloroacetic acid ester 8

Monomer 8

By repeating the same procedures as in Examples 1-4-1 to 1-4-3 aside from using Acid anhydride 4 instead of Acid anhydride 2, there was obtained Monomer 8 (overall yield 26%).

Example 1-11

Synthesis of Monomer 9

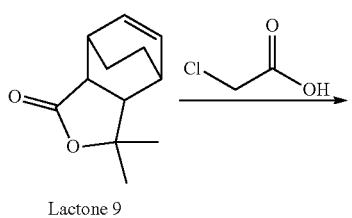

Acid anhydride 5

Lactone 9

Chloroacetic acid ester 9

-continued

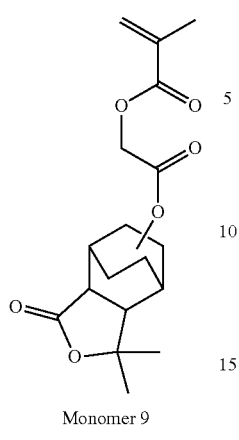

Monomer 9

By repeating the same procedures as in Examples 1-1-1 to 1-1-3 aside from using Acid anhydride 5 instead of Acid anhydride 1, there was obtained Monomer 9 (overall yield 27%).

Example 1-12

Synthesis of Monomer 10

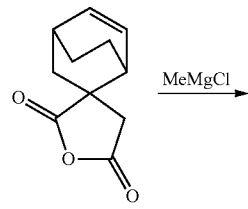

Acid anhydride 6

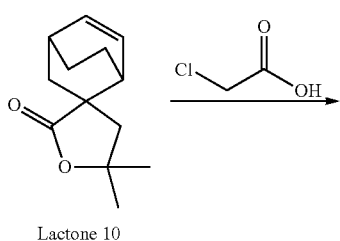

Lactone 10

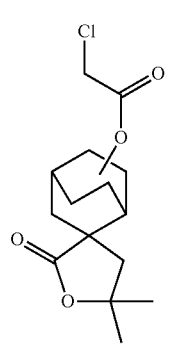

Chloroacetic acid ester 10

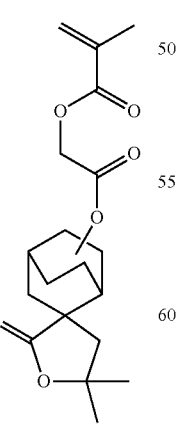

Monomer 10

By repeating the same procedures as in Examples 1-4-1 to 1-4-3 aside from using Acid anhydride 6 instead of Acid anhydride 2, there was obtained Monomer 10 (overall yield 26%).

Example 1-13

Synthesis of Monomer 11

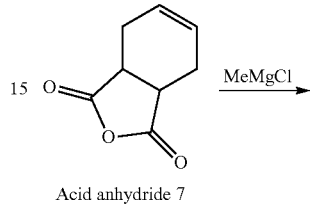

Acid anhydride 7

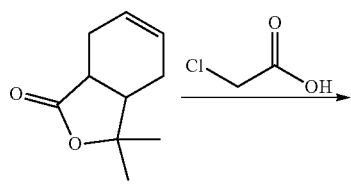

Lactone 11

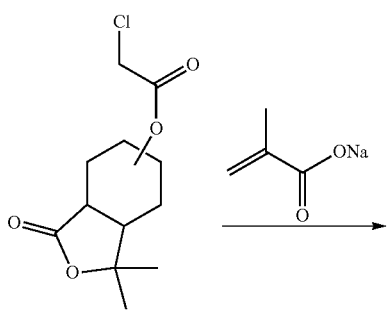

Chloroacetic acid ester 11

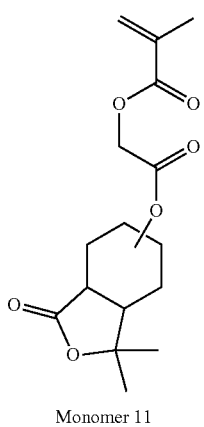

Monomer 11

By repeating the same procedures as in Examples 1-1-1 to 1-1-3 aside from using Acid anhydride 7 instead of Acid anhydride 1, there was obtained Monomer 11 (overall yield 35%).

Example 1-14

Synthesis of Monomer 12

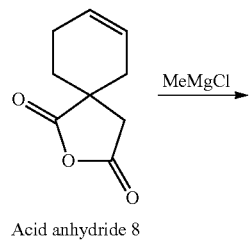

Acid anhydride 8

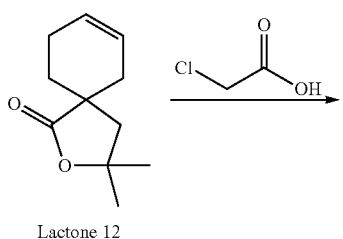

Lactone 12

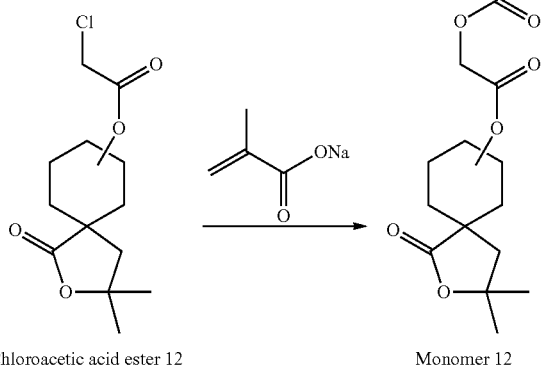

Chloroacetic acid ester 12 → Monomer 12

By repeating the same procedures as in Examples 1-4-1 to 1-4-3 aside from using Acid anhydride 8 instead of Acid anhydride 1, there was obtained Monomer 12 (overall yield 31%).

Example 2

Synthesis of Polymers

Example 2-1

Synthesis of Resist Polymer 1

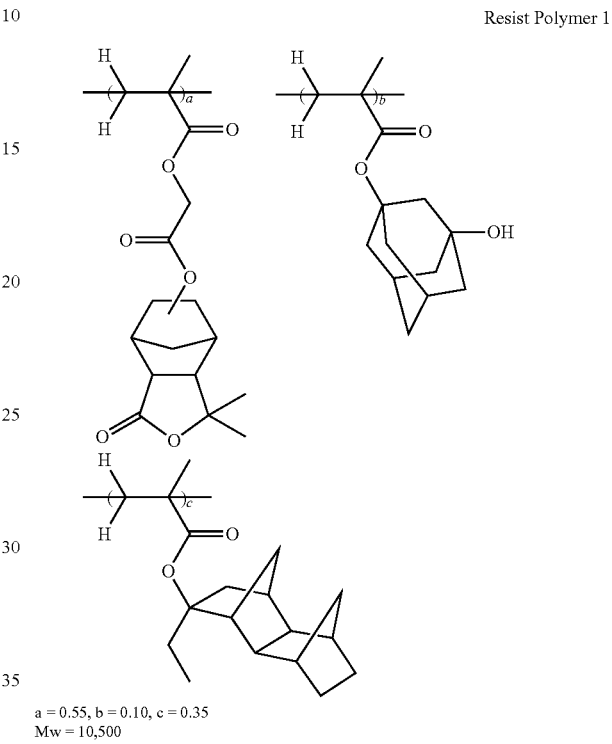

Resist Polymer 1 a = 0.55, b = 0.10, c = 0.35
Mw = 10,500

In nitrogen atmosphere, 29.9 g of Monomer 1, 3.98 g of 3-hydroxyadamantyl methacrylate, 16.2 g of 2-ethyldecahydro-1,4:5,8-dimethanonaphthalen-2-yl methacrylate, and 1.94 g of dimethyl 2,2'-azobisisobutyrate were dissolved in 93 g of propylene glycol monomethyl ether acetate (PGMEA). With stirring in nitrogen atmosphere, 23 g of PGMEA was added dropwise to the solution at 80° C. over 4 hours. At the end of dropwise addition, the solution was kept at 80° C. and stirred for 2 hours. The polymerization solution was cooled to room temperature, and then added dropwise to 800 g of methanol whereupon a solid matter precipitated. The solid precipitate was collected by filtration and vacuum dried at 50° C. for 20 hours. Resist Polymer 1 as represented by the above formula was obtained in white powder solid form. Amount 41.2 g, yield 84%. Notably, a, b and c in the formula are indicative of molar fractions of corresponding recurring units incorporated (the same below).

Examples 2-2 to 2-11 and Comparative Examples 1-1 to 1-5

Synthesis of Resist Polymers 2 to 11 and Comparative Resist Polymers 1 to 5

Resist Polymers 2 to 11 and Comparative Resist Polymers 1 to 5 were prepared by the same procedure as in Example 2-1 except that the type and amount of monomers were changed.

Resist Polymer 2
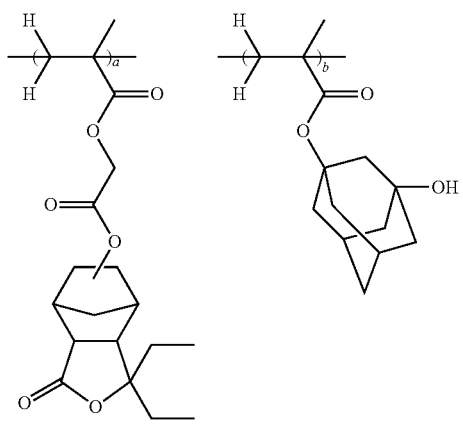
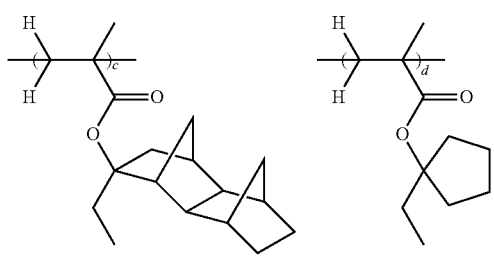
a = 0.50, b = 0.10,
c = 0.20, d = 0.20
Mw = 9,450
Resist Polymer 3
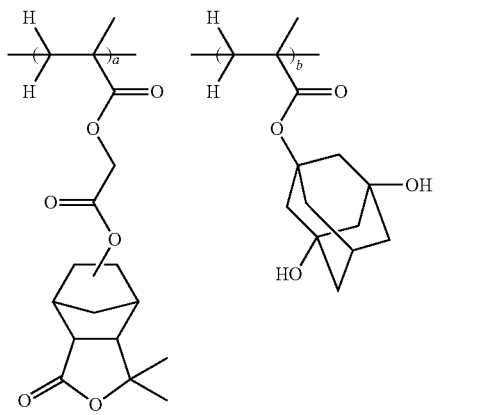
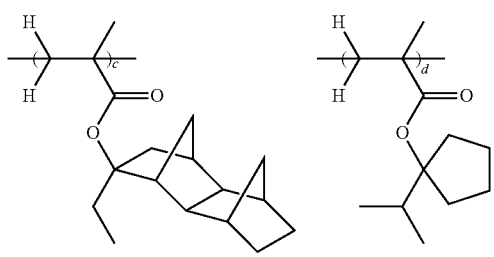
a = 0.50, b = 0.10,
c = 0.20, d = 0.20
Mw = 9,800
Resist Polymer 4
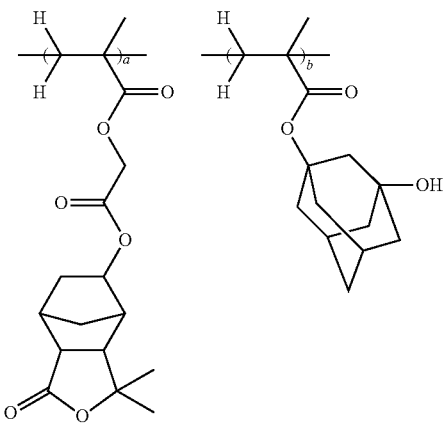
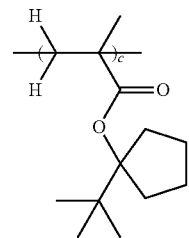
a = 0.40, b = 0.10, c = 0.50
Mw = 9,000
Resist Polymer 5
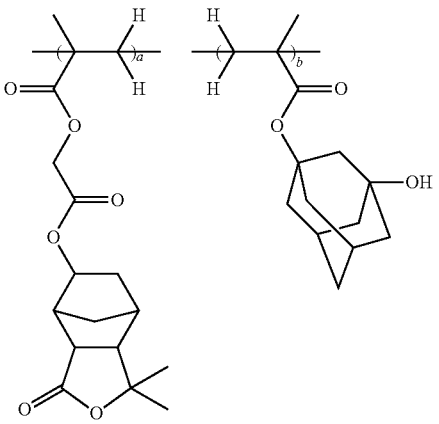
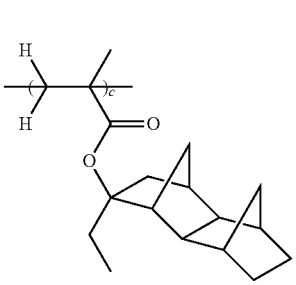
a = 0.55, b = 0.10, c = 0.35
Mw = 10,200

Resist Polymer 6
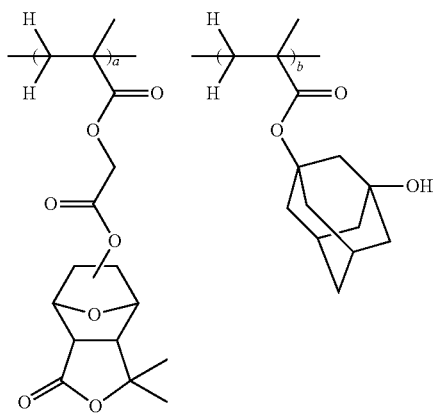
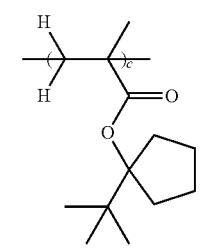
a = 0.45, b = 0.05, c = 0.50
Mw = 8,700
Resist Polymer 7
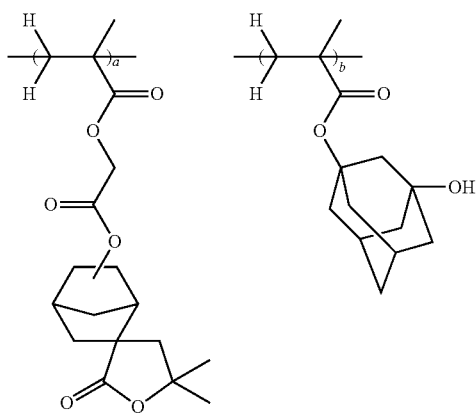
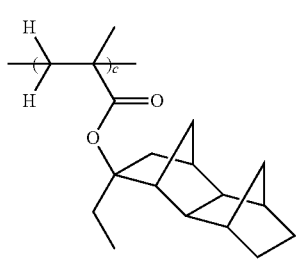
a = 0.55, b = 0.10, c = 0.35
Mw = 11,200
Resist Polymer 8
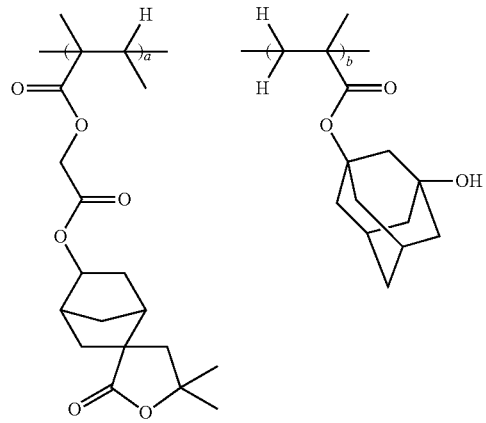
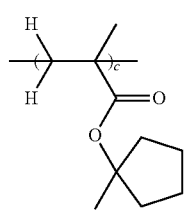
a = 0.40, b = 0.05, c = 0.55
Mw = 7,200
Resist Polymer 9
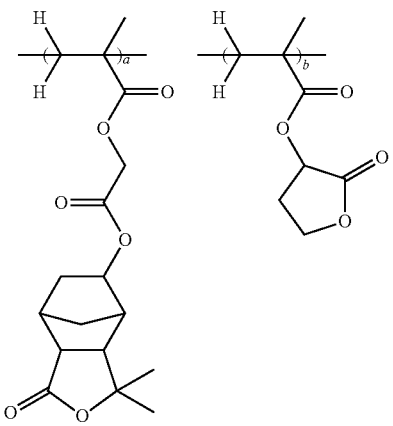
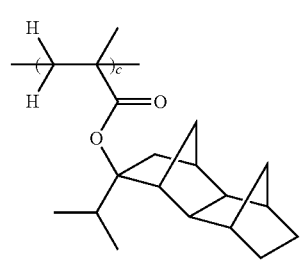
a = 0.35, b = 0.20, c = 0.45
Mw = 7,900

-continued
Resist Polymer 10
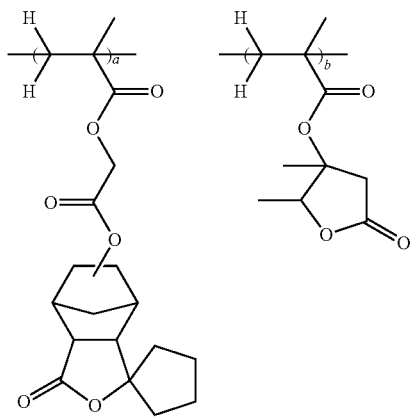
a = 0.42, b = 0.17,
c = 0.26, d = 0.15
Mw = 7,200
Resist Polymer 11
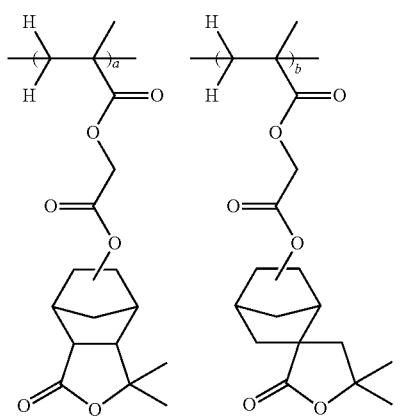
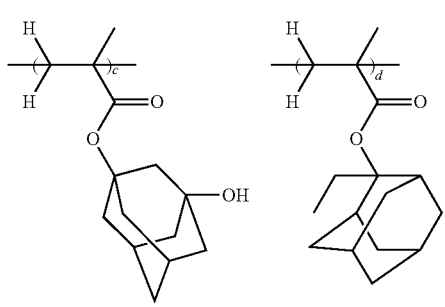
-continued
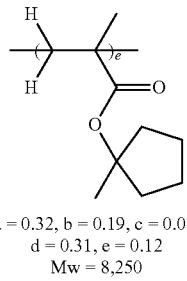
a = 0.32, b = 0.19, c = 0.06,
d = 0.31, e = 0.12
Mw = 8,250
Comparative Resist Polymer 1
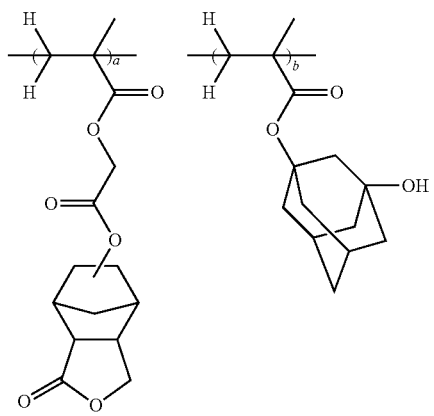
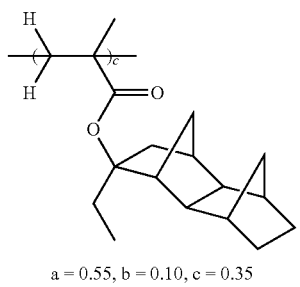
a = 0.55, b = 0.10, c = 0.35
Mw = 10,100
Comparative Resist Polymer 2
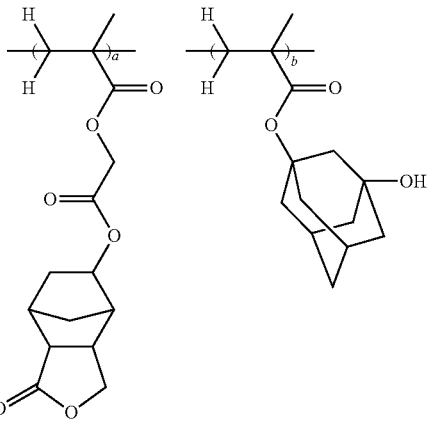

-continued

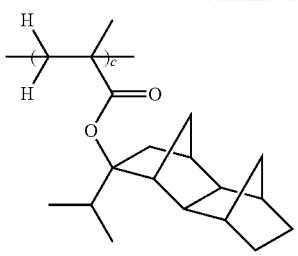

a = 0.56, b = 0.10, c = 0.34
Mw = 9,800

Comparative Resist Polymer 3

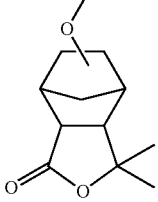

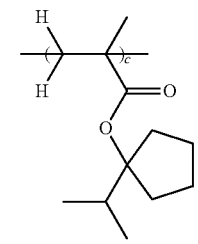

a = 0.50, b = 0.05, c = 0.45
Mw = 10,200

Comparative Resist Polymer 4

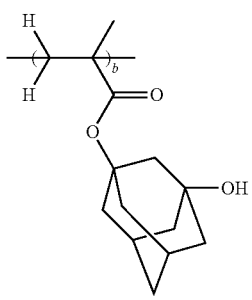

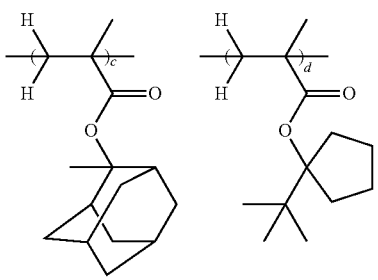

a = 0.55, b = 0.05,
c = 0.30, d = 0.10
Mw = 9,200

Comparative Resist Polymer 5

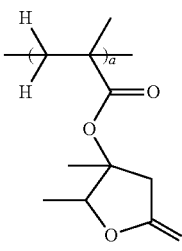 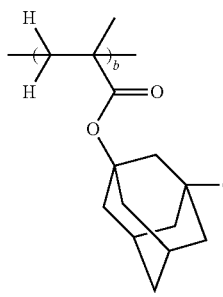

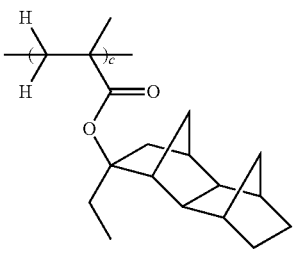

a = 0.50, b = 0.15, c = 0.35
Mw = 10,600

Examples 3-1 to 3-24 and Comparative Examples 2-1 to 2-7

Preparation of Resist Compositions

Resist compositions R-1 to R-24 and Comparative Resist compositions R-25 to R-31 were prepared by using Resist Polymers 1 to 11 or Comparative Resist Polymers 1 to 5 as the base resin, dissolving the polymer and other components in a solvent in accordance with the recipe shown in Tables 1 to 3, and filtering through a Teflon® filter having a pore size of 0.2 μm.

In Tables 1 to 3, acid generator (PAG-1 to PAG-7), quencher (Q-1, Q-2), fluoro-polymer (F-1, F-2), and solvent are as identified below. Notably, the solvent contained 0.01 wt % of surfactant KH-20 (Asahi Glass Co., Ltd.).

Acid generator: PAG-1 to PAG-7

PAG-1

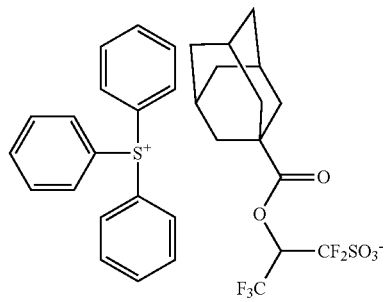

PAG-2
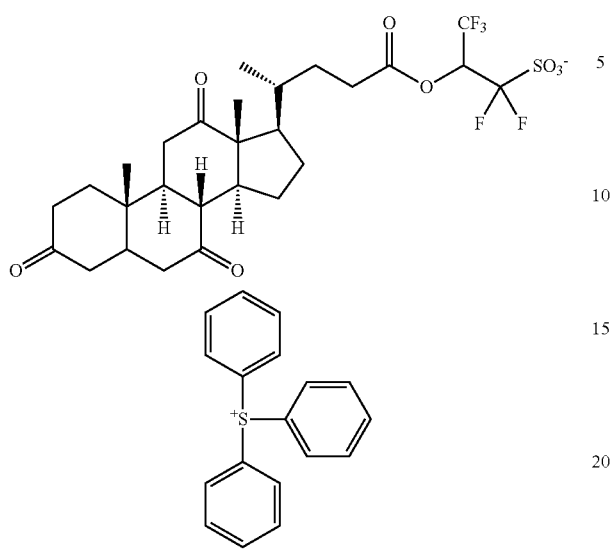
PAG-3
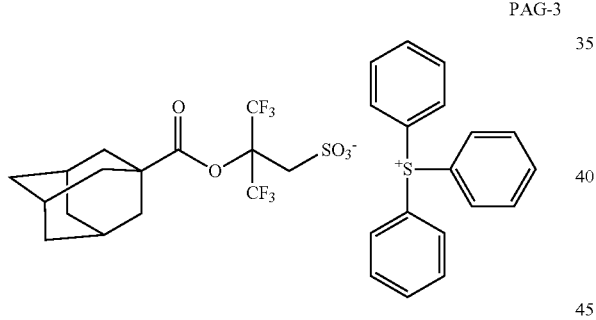
PAG-4
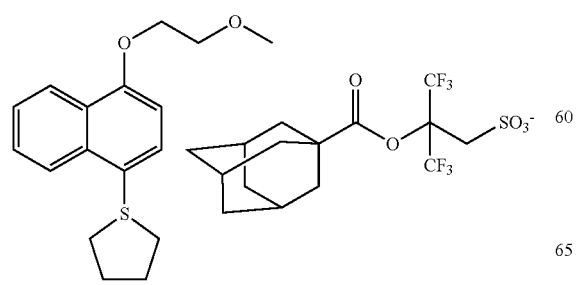
PAG-5
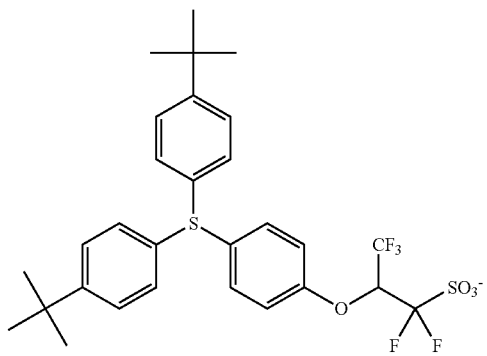
PAG-6
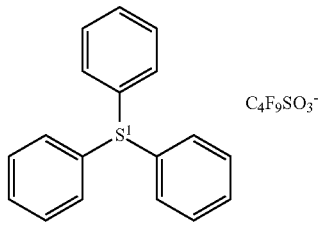
C$_4$F$_9$SO$_3^-$
PAG-7
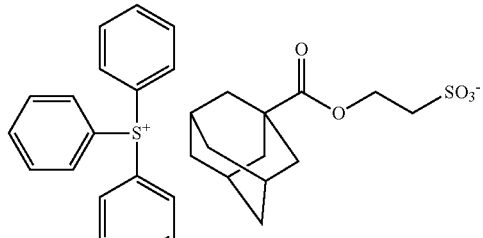
Quencher: Q-1, Q-2
Q-1
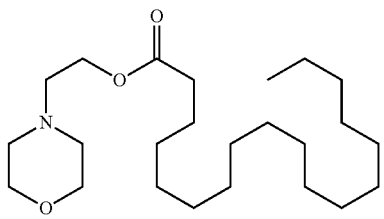
Q-2
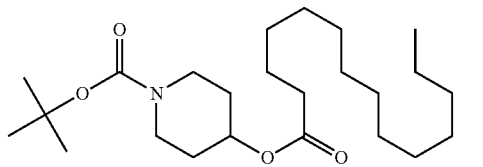

-continued

Fluoro-polymer: F-1, F-2

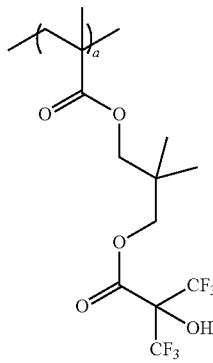

F-1

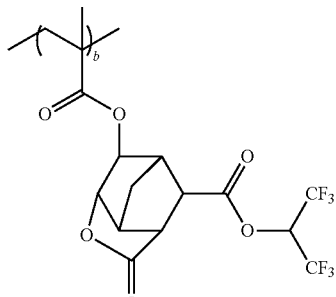

(a = 0.40, b = 0.60, Mw = 11,000)

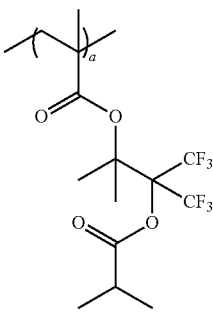

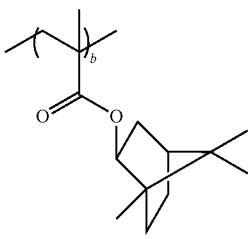

F-2

(a = 0.60, b = 0.40, Mw = 9,000)

Solvent:

S-1: PGMEA (propylene glycol monomethyl ether acetate)

S-2: GBL (γ-butyrolactone)

S-3: diacetone alcohol

TABLE 1

|  |  | Resist composition | Base resin I (pbw) | Base resin II (pbw) | Acid generator I (pbw) | Acid generator II (pbw) | Acid generator III (pbw) | Quencher (pbw) | Fluoro-polymer (pbw) | Solvent I (pbw) | Solvent II (pbw) |
|---|---|---|---|---|---|---|---|---|---|---|---|
| Example | 3-1 | R-1 | Resist Polymer 1 (80) | — | PAG-1 (5) | PAG-7 (2) | — | Q-1 (3) | F-1 (5) | S-1 (1,380) | S-2 (220) |
|  | 3-2 | R-2 | Resist Polymer 1 (80) | — | PAG-1 (3) | PAG-3 (3) | — | Q-2 (3) | F-2 (3) | S-1 (1,600) | — |
|  | 3-3 | R-3 | Resist Polymer 1 (80) | — | PAG-6 (3) | PAG-7 (2) | — | Q-1 (2) | F-2 (3) | S-1 (1,380) | S-2 (220) |
|  | 3-4 | R-4 | Resist Polymer 1 (80) | — | PAG-3 (3) | PAG-5 (5) | — | Q-2 (2.5) | F-2 (3) | S-1 (1,300) | S-2 (330) |
|  | 3-5 | R-5 | Resist Polymer 2 (80) | — | PAG-3 (3) | PAG-5 (5) | — | Q-2 (2.5) | F-2 (3) | S-1 (1,300) | S-2 (330) |
|  | 3-6 | R-6 | Resist Polymer 2 (80) | — | PAG-2 (5) | PAG-4 (3) | PAG-7 (2) | Q-1 (2) | F-1 (5) | S-1 (1,380) | S-2 (220) |
|  | 3-7 | R-7 | Resist Polymer 3 (80) | — | PAG-3 (3) | PAG-5 (5) | — | Q-2 (2.5) | F-2 (3) | S-1 (1,300) | S-2 (330) |
|  | 3-8 | R-8 | Resist Polymer 3 (80) | — | PAG-2 (5) | PAG-4 (3) | PAG-7 (2) | Q-1 (2) | F-1 (5) | S-1 (1,380) | S-2 (220) |
|  | 3-9 | R-9 | Resist Polymer 4 (80) | — | PAG-3 (3) | PAG-5 (5) | — | Q-2 (2.5) | F-2 (3) | S-1 (1,300) | S-3 (330) |
|  | 3-10 | R-10 | Resist Polymer 4 (40) | Resist Polymer 5 (40) | PAG-3 (3) | PAG-5 (5) | — | Q-2 (2.5) | F-2 (3) | S-1 (1,300) | S-2 (330) |
|  | 3-11 | R-11 | Resist Polymer 5 (80) | — | PAG-1 (6) | PAG-7 (2) | — | Q-1 (3) | F-1 (5) | S-1 (1,380) | S-2 (220) |

TABLE 1-continued

|  | Resist compo-sition | Base resin I (pbw) | Base resin II (pbw) | Acid generator I (pbw) | Acid generator II (pbw) | Acid generator III (pbw) | Quencher (pbw) | Fluoro-polymer (pbw) | Solvent I (pbw) | Solvent II (pbw) |
|---|---|---|---|---|---|---|---|---|---|---|
| 3-12 | R-12 | Resist Polymer 5 (80) | — | PAG-3 (3) | PAG-5 (5) | — | Q-2 (2.5) | F-2 (3) | S-1 (1,300) | S-2 (330) |

TABLE 2

|  |  | Resist compo-sition | Base resin I (pbw) | Base resin II (pbw) | Acid generator I (pbw) | Acid generator II (pbw) | Acid generator III (pbw) | Quencher (pbw) | Fluoro-polymer (pbw) | Solvent I (pbw) | Solvent II (pbw) |
|---|---|---|---|---|---|---|---|---|---|---|---|
| Example | 3-13 | R-13 | Resist Polymer 6 (80) | — | PAG-5 (8) | — | — | Q-2 (2.5) | F-2 (3) | S-1 (1,300) | S-2 (330) |
|  | 3-14 | R-14 | Resist Polymer 7 (80) | — | PAG-1 (6) | PAG-7 (2) | — | Q-1 (3) | F-1 (5) | S-1 (1,380) | S-2 (220) |
|  | 3-15 | R-15 | Resist Polymer 7 (80) | — | PAG-3 (3) | PAG-5 (5) | — | Q-2 (2.5) | F-2 (3) | S-1 (1,300) | S-2 (330) |
|  | 3-16 | R-16 | Resist Polymer 7 (80) | — | PAG-6 (3) | PAG-7 (2) | — | Q-1 (2) | F-2 (3) | S-1 (1,380) | S-2 (220) |
|  | 3-17 | R-17 | Resist Polymer 8 (80) | — | PAG-5 (8) | — | — | Q-1 (3) | F-1 (5) | S-1 (1,380) | S-2 (220) |
|  | 3-18 | R-18 | Resist Polymer 8 (80) | — | PAG-3 (3) | PAG-5 (5) | — | Q-2 (2.5) | F-2 (3) | S-1 (1,300) | S-2 (330) |
|  | 3-19 | R-19 | Resist Polymer 9 (80) | — | PAG-6 (3) | PAG-7 (2) | — | Q-1 (4) | F-2 (3) | S-1 (1,380) | S-2 (220) |
|  | 3-20 | R-20 | Resist Polymer 9 (80) | — | PAG-2 (2) | PAG-3 (3) | PAG-5 (5) | Q-2 (2.5) | F-2 (3) | S-1 (1,300) | S-3 (330) |
|  | 3-21 | R-21 | Resist Polymer 10 (80) | — | PAG-2 (5) | PAG-4 (3) | PAG-7 (2) | Q-1 (2) | F-1 (5) | S-1 (1,380) | S-2 (220) |
|  | 3-22 | R-22 | Resist Polymer 10 (80) | — | PAG-3 (3) | PAG-5 (5) | — | Q-2 (2.5) | F-2 (3) | S-1 (1,300) | S-2 (330) |
|  | 3-23 | R-23 | Resist Polymer 11 (80) | — | PAG-2 (5) | PAG-4 (3) | PAG-7 (2) | Q-1 (2) | F-1 (5) | S-1 (1,380) | S-2 (220) |
|  | 3-24 | R-24 | Resist Polymer 11 (80) | — | PAG-3 (3) | PAG-5 (5) | — | Q-2 (2.5) | F-2 (3) | S-1 (1,300) | S-2 (330) |

TABLE 3

|  |  | Resist compo-sition | Base resin I (pbw) | Base resin II (pbw) | Acid generator I (pbw) | Acid generator II (pbw) | Acid generator III (pbw) | Quencher (pbw) | Fluoro-polymer (pbw) | Solvent I (pbw) | Solvent II (pbw) |
|---|---|---|---|---|---|---|---|---|---|---|---|
| Comparative Example | 2-1 | R-25 | Comparative Resist Polymer 1 (80) | — | PAG-6 (3) | PAG-7 (2) | — | Q-1 (2) | F-2 (3) | S-1 (1,380) | S-2 (220) |
|  | 2-2 | R-26 | Comparative Resist Polymer 1 (80) | — | PAG-3 (3) | PAG-5 (5) | — | Q-2 (2.5) | F-2 (3) | S-1 (1,380) | S-2 (220) |

TABLE 3-continued

| | Resist compo-sition | Base resin I (pbw) | Base resin II (pbw) | Acid generator I (pbw) | Acid generator II (pbw) | Acid generator III (pbw) | Quencher (pbw) | Fluoro-polymer (pbw) | Solvent I (pbw) | Solvent II (pbw) |
|---|---|---|---|---|---|---|---|---|---|---|
| 2-3 | R-27 | Comparative Resist Polymer 2 (80) | — | PAG-5 (8) | — | — | Q-2 (2.5) | F-2 (3) | S-1 (1,380) | S-2 (220) |
| 2-4 | R-28 | Comparative Resist Polymer 3 (80) | — | PAG-4 (3) | PAG-5 (5) | — | Q-2 (2.5) | F-1 (5) | S-1 (1,380) | S-2 (220) |
| 2-5 | R-29 | Comparative Resist Polymer 3 (80) | — | PAG-6 (3) | PAG-7 (2) | — | Q-1 (4) | F-2 (3) | S-1 (1,380) | S-2 (220) |
| 2-6 | R-30 | Comparative Resist Polymer 4 (80) | — | PAG-1 (6) | PAG-7 (2) | — | Q-1 (3) | F-1 (5) | S-1 (1,380) | S-2 (220) |
| 2-7 | R-31 | Comparative Resist Polymer 5 (80) | — | PAG-3 (3) | PAG-5 (7) | PAG-7 (2) | Q-1 (1.5) | F-2 (3) | S-1 (1,380) | S-2 (220) |

Examples 4-1 to 4-24 and Comparative Examples 3-1 to 3-7

ArF Lithography Patterning Test (Hole Pattern Evaluation)

On a substrate (silicon wafer), a spin-on carbon film ODL-70 (Shin-Etsu Chemical Co., Ltd.) having a carbon content of 65 wt % was deposited to a thickness of 200 nm and a silicon-containing spin-on hard mask SHB-A940 having a silicon content of 43 wt % was deposited thereon to a thickness of 35 nm. On this substrate for trilayer process, the resist composition (in Tables 1 to 3) was spin coated, then baked on a hot plate at 200° C. for 60 seconds to form a resist film of 100 nm thick.

Using an ArF excimer laser immersion lithography scanner NSR-S610C (Nikon Corp., NA 1.30, σ 0.90/0.72, cross-pole opening 35 deg., azimuthally polarized illumination), exposure was performed through a 6% halftone phase shift mask bearing a desired pattern while varying the dose. After the exposure, the wafer was baked (PEB) at the temperature shown in Table 4 for 60 seconds and developed in an organic solvent. Specifically, the developer shown in Table 4 was injected from a development nozzle while the wafer was spun at 30 rpm for 3 seconds, which was followed by stationary puddle development for 27 seconds, obtaining a hole pattern with a pitch of 100 nm.

Sensitivity

The resist pattern was observed under a top-down electron microscope (TDSEM CG-4000 by Hitachi High-Technologies, Ltd.). The optimum exposure dose (Eop) was defined as an exposure dose (mJ/cm$^2$) which provided a hole diameter of 50 nm at a pitch of 100 nm.

DOF Margin

The hole pattern printed at the optimum dose was measured for hole diameter under TDSEM CG-4000. The depth over which focus was changed that could form a resist pattern with a hole diameter of (50±5) nm was determined and reported as DOF. A larger value indicates a smaller change of pattern size with a change of DOF and hence, better DOF margin.

MEF

The hole pattern was observed under TDSEM CG-4000 and the diameter of holes was measured. A straight line was drawn by plotting the hole pattern size (nm) after reduction projection on the abscissa and the diameter of holes in the resist film via each mask pattern on the ordinate, before the slope of the straight line was determined and reported as MEF. A value of MEF closer to unity (1) indicates better mask reproduction.

The test results are shown in Table 4.

TABLE 4

| | | Resist composition | PEB (° C.) | Developer | Eop (mJ/cm$^2$) | DOF (nm) | MEF |
|---|---|---|---|---|---|---|---|
| Example | 4-1 | R-1 | 90 | n-butyl acetate | 32.0 | 85 | 3.4 |
| | 4-2 | R-2 | 95 | n-butyl acetate | 33.4 | 90 | 3.2 |
| | 4-3 | R-3 | 90 | n-butyl acetate | 29.9 | 95 | 3.2 |
| | 4-4 | R-4 | 90 | n-butyl acetate | 32.5 | 100 | 3.3 |
| | 4-5 | R-5 | 90 | n-butyl acetate | 34.0 | 90 | 3.3 |
| | 4-6 | R-6 | 90 | n-butyl acetate | 33.2 | 85 | 3.1 |
| | 4-7 | R-7 | 90 | n-butyl acetate | 32.8 | 90 | 3.2 |
| | 4-8 | R-8 | 90 | 2-heptanone | 34.5 | 80 | 3.3 |
| | 4-9 | R-9 | 95 | n-butyl acetate | 31.9 | 80 | 3.2 |
| | 4-10 | R-10 | 100 | n-butyl acetate | 28.6 | 85 | 3.4 |
| | 4-11 | R-11 | 95 | n-butyl acetate | 33.1 | 95 | 3.5 |
| | 4-12 | R-12 | 90 | n-butyl acetate | 32.5 | 90 | 3.3 |
| | 4-13 | R-13 | 95 | n-butyl acetate | 34..0 | 80 | 3.4 |

TABLE 4-continued

|  |  | Resist composition | PEB (° C.) | Developer | Eop (mJ/cm$^2$) | DOF (nm) | MEF |
|---|---|---|---|---|---|---|---|
|  | 4-14 | R-14 | 90 | n-butyl acetate | 33.9 | 95 | 3.6 |
|  | 4-15 | R-15 | 85 | n-butyl acetate | 35.0 | 95 | 3.4 |
|  | 4-16 | R-16 | 90 | n-butyl acetate | 34.2 | 100 | 3.6 |
|  | 4-17 | R-17 | 95 | n-butyl acetate | 34.7 | 80 | 3.3 |
|  | 4-18 | R-18 | 90 | methyl benzoate | 31.2 | 80 | 3.4 |
|  | 4-19 | R-19 | 95 | n-butyl acetate | 30.2 | 90 | 3.5 |
|  | 4-20 | R-20 | 90 | n-butyl acetate | 34.1 | 90 | 3.3 |
|  | 4-21 | R-21 | 95 | n-butyl acetate | 33.9 | 85 | 3.4 |
|  | 4-22 | R-22 | 90 | n-butyl acetate | 34.5 | 80 | 3.1 |
|  | 4-23 | R-23 | 95 | n-butyl acetate | 33.1 | 90 | 3.3 |
|  | 4-24 | R-24 | 90 | n-butyl acetate | 34.0 | 85 | 3.2 |
| Comparative | 3-1 | R-25 | 95 | n-butyl acetate | 31.1 | 75 | 3.9 |
| Example | 3-2 | R-26 | 90 | n-butyl acetate | 30.7 | 55 | 3.4 |
|  | 3-3 | R-27 | 90 | n-butyl acetate | 30.5 | 80 | 4.1 |
|  | 3-4 | R-28 | 95 | n-butyl acetate | 30.2 | 65 | 3.6 |
|  | 3-5 | R-29 | 90 | n-butyl acetate | 31.2 | 75 | 3.8 |
|  | 3-6 | R-30 | 90 | 2-heptanone | 34.5 | 65 | 4.2 |
|  | 3-7 | R-31 | 95 | n-butyl acetate | 30.7 | 80 | 3.9 |

As seen from Table 4, the resist compositions within the scope of the invention are improved in DOF and MEF over the resist compositions using known lactone compounds.

While the invention has been illustrated and described in typical embodiments, it is not intended to be limited to the details shown, since various modifications and substitutions can be made without departing in any way from the spirit of the present invention. As such, further modifications and equivalents of the invention herein disclosed may occur to persons skilled in the art using no more than routine experimentation, and all such modifications and equivalents are believed to be within the spirit and scope of the invention as defined by the following claims.

Japanese Patent Application No. 2015-253067 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A polymer comprising recurring units having the formula (1):

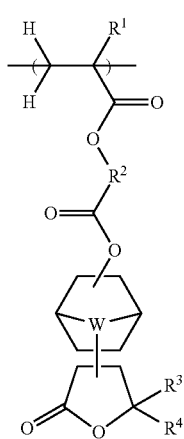

(1)

wherein $R^1$ is hydrogen or methyl, $R^2$ is a $C_1$-$C_{20}$ straight, branched or cyclic divalent hydrocarbon group in which any constituent —$CH_2$— moiety may be replaced by —O— or —C(=O)—, $R^3$ and $R^4$ are each independently a $C_1$-$C_{15}$ straight, branched or cyclic alkyl group, $R^3$ and $R^4$ may bond together to form a ring with the carbon atom to which they are attached, a ring-forming combination of $R^3$ and $R^4$ is a $C_2$-$C_{15}$ straight, branched or cyclic alkylene group, W is —$CH_2$—, —$CH_2CH_2$— or —O—, or two separate —H, the broken line designates a single bond or divalent organic group bonding the norbornane, bicyclo[2.2.2]octane, 7-oxanorbornane or cyclohexane ring structure to the γ-butyrolactone ring structure, or a structure sharing one or two constituent carbon atoms between these ring structures.

2. The polymer of claim 1 wherein the recurring units having the formula (1) are recurring units having the formula (2) or (3):

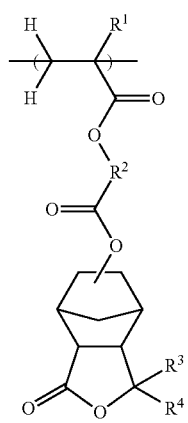

(2)

(3)

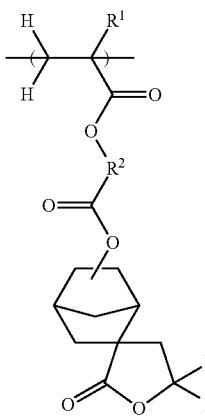

wherein $R^1$ to $R^4$ are as defined above.

3. The polymer of claim 1, further comprising recurring units having the formula (4):

(4)

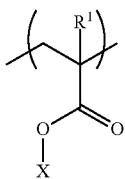

wherein $R^1$ is as defined above, and X is an acid labile group.

4. The polymer of claim 1, further comprising recurring units of at least one type selected from recurring units having the formulae (5) to (7):

(5)

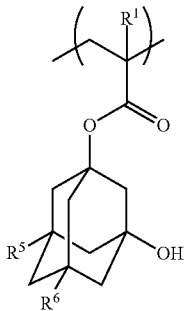

(6)

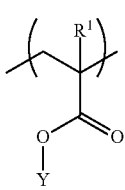

(7)

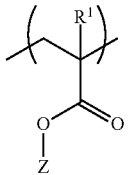

wherein $R^1$ is as defined above, $R^5$ and $R^6$ are each independently hydrogen or hydroxyl, Y is a substituent group containing a lactone structure different from formula (1) or a substituent group containing a sultone structure, Z is hydrogen, a $C_1$-$C_{15}$ fluorinated hydrocarbon group, or a $C_1$-$C_{15}$ fluoroalcohol-containing substituent group.

5. A resist composition comprising (A) a base resin comprising the polymer of claim 1, (B) a photoacid generator, and (C) a solvent.

6. The resist composition of claim 5 wherein the photoacid generator (B) comprises a photoacid generator having the formula (B-1):

(B-1)

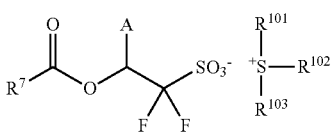

wherein $R^7$ is a $C_1$-$C_{35}$ straight, branched or cyclic monovalent hydrocarbon group which may contain an oxygen atom, a nitrogen-containing heterocyclic group, or a group of the formula (i):

$$(R^8)(R^9)N-R^{10}-$$ (i)

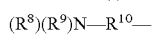

wherein $R^8$ and $R^9$ are each independently hydrogen or a $C_1$-$C_{20}$ monovalent hydrocarbon group which may contain a heteroatom, $R^8$ and $R^9$ may bond together to form a ring with the nitrogen atom to which they are attached, $R^{10}$ is a $C_1$-$C_{20}$ divalent hydrocarbon group which may contain a heteroatom, A is hydrogen or trifluoromethyl, $R^{101}$, $R^{102}$ and $R^{103}$ each independently an optionally substituted $C_1$-$C_{10}$ straight or branched alkyl, alkenyl or oxoalkyl group, or an optionally substituted $C_6$-$C_{18}$ aryl, aralkyl or aryloxoalkyl group, any two of $R^{101}$, $R^{102}$ and $R^{103}$ may bond together to form a ring with the sulfur atom to which they are attached.

7. The resist composition of claim 5 wherein the photoacid generator (B) comprises a photoacid generator having the formula (B-2):

(B-2)

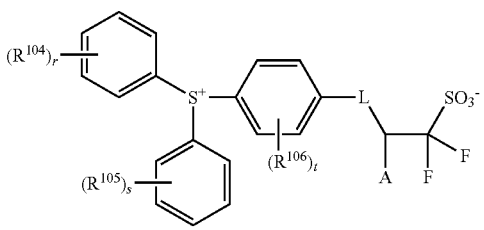

wherein A is hydrogen or trifluoromethyl, $R^{104}$, $R^{105}$ and $R^{106}$ are each independently hydrogen or a $C_1$-$C_{20}$ straight, branched or cyclic monovalent hydrocarbon group which may contain a heteroatom, r and s are each independently an integer of 0 to 5, t is an integer of 0 to 4, and L is a single bond or a $C_1$-$C_{20}$ straight, branched or cyclic divalent hydrocarbon group which may contain a heteroatom.

8. The resist composition of claim 5 wherein the photoacid generator (B) comprises a photoacid generator having the formula (B-3):

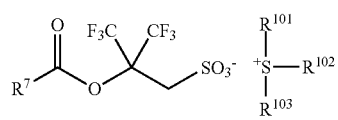

(B-3)

wherein $R^7$ is a $C_1$-$C_{35}$ straight, branched or cyclic monovalent hydrocarbon group which may contain an oxygen atom, a nitrogen-containing heterocyclic group, or a group of the formula (i):

$(R^8)(R^9)N-R^{10}-$  (i)

wherein $R^8$ and $R^9$ are each independently hydrogen or a $C_1$-$C_{20}$ monovalent hydrocarbon group which may contain a heteroatom, $R^8$ and $R^9$ may bond together to form a ring with the nitrogen atom to which they are attached, $R^{10}$ is a $C_1$-$C_{20}$ divalent hydrocarbon group which may contain a heteroatom, $R^{101}$, $R^{102}$ and $R^{103}$ are each independently an optionally substituted $C_1$-$C_{10}$ straight or branched alkyl, alkenyl or oxoalkyl group, or an optionally substituted $C_6$-$C_{18}$ aryl, aralkyl or aryloxoalkyl group, any two of $R^{101}$, $R^{102}$ and $R^{103}$ may bond together to form a ring with the sulfur atom to which they are attached.

9. The resist composition of claim 5, further comprising (D) a second polymer different from the polymer (A), the second polymer comprising recurring units of at least one type selected from recurring units having the formulae (D-1) to (D-5):

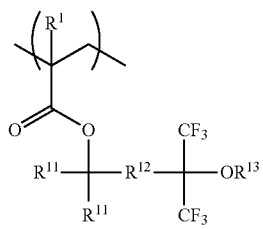

(D-1)

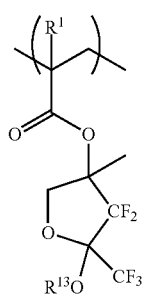

(D-2)

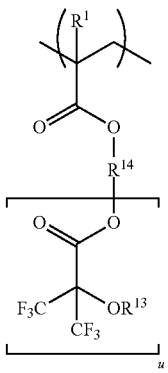

(D-3)

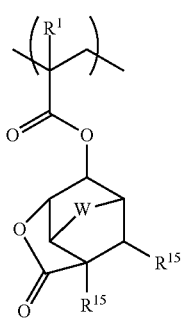

(D-4)

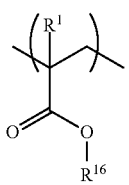

(D-5)

wherein $R^1$ and W are as defined above, $R^{11}$ is each independently hydrogen or a $C_1$-$C_{10}$ straight, branched or cyclic monovalent hydrocarbon group, $R^{12}$ is a single bond or a $C_1$-$C_5$ straight or branched divalent hydrocarbon group, $R^{13}$ is each independently hydrogen, a $C_1$-$C_{15}$ straight, branched or cyclic monovalent hydrocarbon or monovalent fluorinated hydrocarbon group, or an acid labile group, the monovalent hydrocarbon or fluorinated hydrocarbon group represented by $R^{13}$ may have an ether bond (—O—) or carbonyl moiety (—C(=O)—) intervening in a carbon-carbon bond, $R^{14}$ is a $C_1$-$C_{20}$ straight, branched or cyclic (u+1)-valent hydrocarbon or fluorinated hydrocarbon group, u is an integer of 1 to 3, $R^{15}$ is each independently hydrogen or a group of the formula (ii):

—C(=O)—O—$R^{17}$  (ii)

wherein $R^{17}$ is a $C_1$-$C_{20}$ straight, branched or cyclic monovalent fluorinated hydrocarbon group, $R^{16}$ is a $C_1$-$C_{15}$ straight, branched or cyclic monovalent hydrocarbon or monovalent fluorinated hydrocarbon group which may have an ether bond (—O—) or carbonyl moiety (—C(=O)—) intervening in a carbon-carbon bond.

10. A pattern forming process comprising the steps of applying the resist composition of claim 5 onto a substrate, prebaking to form a resist film, exposing the resist film to KrF excimer laser, ArF excimer laser, EB or EUV, baking, and developing the exposed resist film in a developer.

11. The process of claim 10 wherein the exposure step is carried out by immersion lithography using a liquid having a refractive index of at least 1.0 between the resist film and a projection lens.

12. The process of claim 11, further comprising the step of forming a protective film on the resist film prior to the exposure step, wherein immersion lithography is carried out while the liquid is held between the protective film and the projection lens.

13. The process of claim 10 wherein the developing step uses the developer comprising an organic solvent to form a negative pattern.

* * * * *